(12) United States Patent
Van Bilsen et al.

(10) Patent No.: US 9,133,517 B2
(45) Date of Patent: Sep. 15, 2015

(54) METHODS AND SEQUENCES TO PREFERENTIALLY SUPPRESS EXPRESSION OF MUTATED HUNTINGTIN

(75) Inventors: Paul H. J. Van Bilsen, Maastricht (NL); Leonie Jaspers, Maastricht (NL)

(73) Assignee: Medtronics, Inc., Minneapolis, MN (US)

( * ) Notice: Subject to any disclaimer, the term of this patent is extended or adjusted under 35 U.S.C. 154(b) by 626 days.

(21) Appl. No.: 12/560,178

(22) Filed: Sep. 15, 2009

(65) Prior Publication Data

US 2010/0120900 A1    May 13, 2010

Related U.S. Application Data

(63) Continuation of application No. PCT/US2008/064532, filed on May 22, 2008, which is a continuation-in-part of application No. PCT/US2007/012259, filed on May 23, 2007, which is a continuation-in-part of application No. 11/439,858, filed on May 24, 2006, said application No. PCT/US2008/064532 is a continuation-in-part of application No. 11/478,110, filed on Jun. 28, 2006, now abandoned.

(60) Provisional application No. 60/695,078, filed on Jun. 28, 2005.

(51) Int. Cl.
  *C12Q 1/68* (2006.01)
  *C07H 21/04* (2006.01)
  *C12P 19/34* (2006.01)

(52) U.S. Cl.
  CPC ........ *C12Q 1/6883* (2013.01); *C12Q 2600/106* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis | |
| 4,888,829 A | 12/1989 | Kleinerman et al. | |
| 4,965,188 A | 10/1990 | Mullis et al. | |
| 5,236,908 A | 8/1993 | Gruber et al. | |
| 5,354,326 A | 10/1994 | Comben et al. | |
| 5,534,350 A | 7/1996 | Liou | |
| 5,624,803 A | 4/1997 | Noonberg et al. | |
| 5,639,275 A | 6/1997 | Baetge et al. | |
| 5,702,716 A | 12/1997 | Dunn et al. | |
| 5,720,720 A | 2/1998 | Laske et al. | |
| 5,735,814 A | 4/1998 | Elsberry et al. | |
| 5,782,892 A | 7/1998 | Castle et al. | |
| 5,800,390 A | 9/1998 | Hayakawa et al. | |
| 5,814,014 A | 9/1998 | Elsberry et al. | |
| 5,840,059 A | 11/1998 | March et al. | |
| 5,882,561 A | 3/1999 | Barsoum et al. | |
| 5,925,310 A | 7/1999 | Nakayama et al. | |
| 5,942,455 A | 8/1999 | Barsoum et al. | |
| 5,968,059 A | 10/1999 | Ellis et al. | |
| 5,985,561 A | 11/1999 | Kimberly et al. | |
| 5,997,525 A | 12/1999 | March et al. | |
| 6,042,579 A | 3/2000 | Elsberry et al. | |
| 6,093,180 A | 7/2000 | Elsberry | |
| 6,110,459 A | 8/2000 | Mickle et al. | |
| 6,151,525 A | 11/2000 | Soykan et al. | |
| 6,180,613 B1 | 1/2001 | Kaplitt et al. | |
| 6,187,906 B1 | 2/2001 | Gluckman et al. | |
| 6,231,969 B1 | 5/2001 | Knight et al. | |
| 6,245,884 B1 | 6/2001 | Hook | |
| 6,251,589 B1 | 6/2001 | Tsuji et al. | |
| 6,281,009 B1 | 8/2001 | Boyce | |
| 6,291,243 B1 | 9/2001 | Fogarty et al. | |
| 6,294,202 B1 | 9/2001 | Burns et al. | |
| 6,300,539 B1 | 10/2001 | Morris | |
| 6,309,634 B1 | 10/2001 | Bankiewicz et al. | |
| 6,310,048 B1 | 10/2001 | Kumar | |
| 6,313,268 B1 | 11/2001 | Hook | |
| 6,319,905 B1 | 11/2001 | Mandel et al. | |
| 6,343,233 B1 | 1/2002 | Werner et al. | |
| 6,372,250 B1 | 4/2002 | Pardridge | |

(Continued)

FOREIGN PATENT DOCUMENTS

| | | |
|---|---|---|
| DE | 19938960 | 2/2001 |
| JP | 2004232811 | 8/2004 |

(Continued)

OTHER PUBLICATIONS

Andersen et al (J. Agric. Food Chem., vol. 54, No. 26, 2006).*
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).

(Continued)

*Primary Examiner* — Richard Schnizer
(74) *Attorney, Agent, or Firm* — Fox Rothschild LLP; Gerard P. Norton; Jianming J. Hao

(57) ABSTRACT

Disclosed herein are methods and sequences to preferentially suppress the expression of the mutated huntingtin ("htt") protein over expression of the normal htt protein. Also disclosed are methods comprising screening an individual for the heterozygous presence of one or more single nucleotide polymorphisms within the individual's Huntington's genes; administering nucleic acid molecules comprising nucleotide sequences that preferentially suppress the expression of amino acid sequences encoding for mutated huntingtin ("htt") over suppressing the expression of amino acid sequences encoding for normal htt by targeting an area of a Huntington's disease gene that is heterozygous for the presence of one or more single nucleotide polymorphisms.

10 Claims, 5 Drawing Sheets

(56) References Cited

U.S. PATENT DOCUMENTS

| | | |
|---|---|---|
| 6,372,721 B1 | 4/2002 | Neuman et al. |
| 6,376,471 B1 | 4/2002 | Lawrence, III et al. |
| 6,436,392 B1 | 8/2002 | Engelhardt et al. |
| 6,436,708 B1 | 8/2002 | Leone et al. |
| 6,461,989 B1 | 10/2002 | El-Raghy et al. |
| 6,468,524 B1 | 10/2002 | Chiorini et al. |
| 6,551,290 B1 | 4/2003 | Elsberry et al. |
| 6,594,880 B2 | 7/2003 | Elsberry |
| 6,609,020 B2 | 8/2003 | Gill |
| 6,632,671 B2 | 10/2003 | Unger |
| 6,659,995 B1 | 12/2003 | Taheri |
| 6,870,030 B2 | 3/2005 | Powell et al. |
| 6,945,969 B1 | 9/2005 | Morris et al. |
| 7,320,965 B2 | 1/2008 | Sah et al. |
| 7,645,576 B2 | 1/2010 | Lo et al. |
| 2001/0027309 A1 | 10/2001 | Elsberry |
| 2001/0031947 A1 | 10/2001 | Heruth |
| 2002/0004038 A1 | 1/2002 | Baugh et al. |
| 2002/0068093 A1 | 6/2002 | Trogolo et al. |
| 2002/0114780 A1 | 8/2002 | Bankiewicz |
| 2002/0141980 A1 | 10/2002 | Bankiewicz |
| 2002/0187127 A1 | 12/2002 | Bankiewicz |
| 2003/0078229 A1 | 4/2003 | Cooper et al. |
| 2003/0088236 A1 | 5/2003 | Johnson et al. |
| 2003/0092003 A1 | 5/2003 | Blatt et al. |
| 2003/0095958 A1 | 5/2003 | Bhisetti et al. |
| 2003/0109476 A1 | 6/2003 | Kmiec et al. |
| 2003/0120282 A1 | 6/2003 | Scouten et al. |
| 2003/0143732 A1 | 7/2003 | Fosnaugh et al. |
| 2003/0152947 A1 | 8/2003 | Crossman |
| 2003/0175772 A1 | 9/2003 | Wang |
| 2003/0190635 A1 | 10/2003 | McSwiggen |
| 2003/0224512 A1 | 12/2003 | Dobie |
| 2003/0232353 A1 | 12/2003 | Kennedy |
| 2004/0018520 A1 | 1/2004 | Thompson |
| 2004/0023390 A1 | 2/2004 | Davidson et al. |
| 2004/0023855 A1 | 2/2004 | John et al. |
| 2004/0186422 A1 | 9/2004 | Rioux |
| 2004/0215164 A1 | 10/2004 | Abbott |
| 2004/0220132 A1 | 11/2004 | Kaemmerer |
| 2004/0258666 A1 | 12/2004 | Passini |
| 2004/0259247 A1 | 12/2004 | Tuschl |
| 2004/0265849 A1* | 12/2004 | Cargill et al. ............... 435/6 |
| 2004/0266707 A1 | 12/2004 | Leake |
| 2005/0032733 A1 | 2/2005 | McSwiggen |
| 2005/0042646 A1 | 2/2005 | Davidson |
| 2005/0048641 A1 | 3/2005 | Hildebrand |
| 2005/0096284 A1* | 5/2005 | McSwiggen ............... 514/44 |
| 2005/0137134 A1 | 6/2005 | Gill |
| 2005/0153353 A1 | 7/2005 | Meibohm |
| 2005/0177866 A1 | 8/2005 | Kirsch |
| 2005/0180955 A1 | 8/2005 | Bankiewicz |
| 2005/0202075 A1 | 9/2005 | Pardridge |
| 2005/0209179 A1 | 9/2005 | McSwiggen |
| 2005/0255086 A1 | 11/2005 | Davidson |
| 2005/0282198 A1 | 12/2005 | Duff |
| 2006/0009408 A1 | 1/2006 | Davidson et al. |
| 2006/0014165 A1 | 1/2006 | Hakonarson |
| 2006/0041242 A1 | 2/2006 | Stypulkowski |
| 2006/0150747 A1 | 7/2006 | Mallett |
| 2006/0210538 A1 | 9/2006 | Kaplitt et al. |
| 2006/0224411 A1 | 10/2006 | Chang |
| 2006/0257912 A1 | 11/2006 | Kaemmerer |
| 2007/0031844 A1 | 2/2007 | Khvorova et al. |
| 2007/0161590 A1* | 7/2007 | Van Bilsen et al. ............... 514/44 |
| 2007/0184029 A1 | 8/2007 | Mishra |
| 2008/0113351 A1 | 5/2008 | Naito |
| 2009/0022864 A1 | 1/2009 | Steenhof |

FOREIGN PATENT DOCUMENTS

| | | |
|---|---|---|
| WO | WO9220400 | 11/1992 |
| WO | WO9323569 | 11/1993 |
| WO | WO9402595 | 2/1994 |
| WO | WO9618736 | 6/1996 |
| WO | WO9740847 | 11/1997 |
| WO | WO9846273 | 10/1998 |
| WO | WO9846740 | 10/1998 |
| WO | WO9939744 | 8/1999 |
| WO | WO9950300 | 10/1999 |
| WO | WO0030567 | 6/2000 |
| WO | WO0064505 | 11/2000 |
| WO | WO0116312 | 3/2001 |
| WO | WO0149844 | 7/2001 |
| WO | WO0160794 | 8/2001 |
| WO | WO0170276 | 9/2001 |
| WO | WO0180840 | 11/2001 |
| WO | WO0191801 | 12/2001 |
| WO | WO0205804 | 1/2002 |
| WO | WO0207810 | 1/2002 |
| WO | WO0222177 | 3/2002 |
| WO | WO03042385 | 5/2003 |
| WO | WO03047676 | 6/2003 |
| WO | WO03053516 | 7/2003 |
| WO | WO03070895 | 8/2003 |
| WO | WO03099298 | 12/2003 |
| WO | WO03102131 | 12/2003 |
| WO | WO2004007718 | 1/2004 |
| WO | WO2004010787 | 2/2004 |
| WO | WO2004013280 | 2/2004 |
| WO | WO2004013355 | 2/2004 |
| WO | WO2004041101 | 5/2004 |
| WO | WO2004047872 | 6/2004 |
| WO | WO2004058940 | 7/2004 |
| WO | WO2004084955 | 10/2004 |
| WO | WO2004098648 | 11/2004 |
| WO | WO2004101063 | 11/2004 |
| WO | WO2005027980 | 3/2005 |
| WO | WO2005045034 | 5/2005 |
| WO | WO2005116204 | 8/2005 |
| WO | WO2005120581 | 12/2005 |
| WO | WO2006022639 | 3/2006 |
| WO | WO2007039721 | 4/2007 |
| WO | WO2008005562 | 7/2007 |
| WO | WO2007087451 | 8/2007 |
| WO | WO2007139811 | 12/2007 |
| WO | WO2008004260 | 1/2008 |
| WO | WO2008021157 | 2/2008 |
| WO | WO2008046273 | 4/2008 |
| WO | WO2008143774 | 11/2008 |

OTHER PUBLICATIONS

Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc© vectors), for the intracellular targeting of recombinant proteins and antibodies, Catalog Nos. V820-20, V821-20, V822-20, V823-20, Version E, copyright 1998-2001, 35 pgs.
Invitrogen, pTRACER™-CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).

(56) References Cited

OTHER PUBLICATIONS

Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Feb. 2, 2005, 5 pgs.
Mirus, TransIT-TKO® Transfection Reagent, Product Nos. MIR 2154, MIR 2150, MIR 2155, MIR 2156, Lit. # ML015, Rev. 7/04, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
National Center for Biotechnology Information, National Library of Medicine, National Institutes of Health, "What does NCBI do?" [online]. Bethesda, MD [retrieved on Dec. 5, 2005], Revised Dec. 2005. Retrieved from the Internet: <URL:http://www.ncbi.nlm.nih.gov>; 2 pgs.
National Center for Biotechnology Information, National Library of Medicine, National Institutes of Health, GenBank Locus AF163864, Accession No. AF163864, "Homo sapiens SNCA isoform (SNCA) gene, complete cds, alternatively spliced, " [online]. Bethesda, MD [retrieved on Jun. 21, 2004]. Retrieved from the Internet: <URL:http://www.ncbi.nlm.nih.gov/entrez/viewer.fcgi?db=nucleotide&val=11118351>; 43 pgs.
National Center for Biotechnology Information, National Library of Medicine, National Institutes of Health, GenBank Locus AF163865, Accession No. AF163865, "Mus musculus alpha-synuclein (SNCA) gene, complete cds," [online]. Bethesda, MD [retrieved on Jun. 21, 2004]. Retrieved from the Internet<URL:http://www.ncbi.nlm.nih.gov/entrez/viewer.fcgi?db=nucleotide&val=11118354>; 33 pgs.
Aebisher, Trends in Neurosci. 24(9) 553-540 (Sep. 2001).
Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 µg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.
Ausubel et al., Eds., Current Protocols in Molecular Biology, vols. 1-3, John Wiley & Sons, Inc., New York, NY, 1994; title page, publisher's page and table of contents only, 14 pgs.
Basi et al., "Antagonistic Effects of ß -site Amyloid Precursor Protein-cleaving Enzymes 1 and 2 on ß - Amyloid Peptide Production in Cells," J. Bio. Chem., Published, JBC Papers in Press, Jun. 2003; 278(34): 31512-31520.
Bass et al., Nature 411: 428-429 (2001).
Bertrand et al., Biochem Biophys Res Comm 296: 1000-1004 (2002).
Bodendorf et al., J. Neurochem. 80(5), 799-806 (Mar. 2002).
Boillée et al., "Gene therapy for ALS deliver," Trends in Neurosciences, May 2004; 27(5): 235-238.
Bortolin, Susan et al., "Analytical validation of the tag-it high-throughout microsphere-based universal array genotyping platform. Application to the multiplex detection of a panel of thrombophilia-associates single-nucleotide polymorphisms." American Association for Clinical Chemistry vol. 50(11) 2028-2036 (2004).
Brentano et al., P.N.A.S. 89:4099-4103 (1992).
Brummelkamp et al., Science 296: 550-553 (2002).
Burger et al., Mol. Ther. 10(2) 302-317 (Aug. 2004).
Cahill et al Atlas of Human Cross-Sectional Anatomy Wiley-Liss, 3rd Ed. (1995).
Cai et al., Nat. Neurosci. 4(3) 233-234 (2004).
Callahan Am. J. Pathol. 158(3) 1173-1177 (2001).
Caplen et al, Human Mol. Genet. 11(2) 175-184 (2002).
Chen et al., Nucl. Acid. Res. 20, 4581-4589 (1992).
Chi et al., "Genomewide view of gene silencing by small interfering RNAs," Proc. Natl. Acad. Sci. USA, May 2003; 100 (11): 6343-6346.
Chowhira et al., J. Biol. Chem. 269, 25856-25863 (1994).
Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J. Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; 12(12): 1587-1598.
Elbashir et al., "Analysis of gene function in somatic mammalian cells using small interfering RNAs," Methods 26 (2002); pp. 199-213.
ElBashir, EMBOJ 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behay. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Zhang et al., 1996 J. Mol. Neurosci. 7: 13-28 (1996).
Zhao et al., J. Biol. Chem. 271(49), 31407-31411 (Dec. 1996).
Zlokovic et al., Neurosurgery 40 805-813 (1997).
National Center for Biotechnology Information, National Library of Medicine, National Institutes of Health, GenBank Locus XM_032588, Accession No. XM_032588, "Homo sapiens dentatorubral-pallidoluysian atrophy (artrophin-1) (DRPLA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=20555988>; 3 pgs.
National Center for Biotechnology Information, National Library of Medicine, National Institutes of Health, GenBank Locus XM_132846, Accession No. XM_132846, "Mus musculus dentatorubral pallidoluysian atrophy (DRPLA) mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=20832263>; 3 pgs.
Noonberg et al., Nucl. Acid Res. 22(14) 2830-2836 (1994).
Noordmans et al., Soc. Neurosci. Abstr. 27, Program 572.14 (2001).
Ohkawa Nucl. Acid. Symp. Ser. 27, 15-16 (1992).
Ohno et al., "BACEI Deficiency Rescues Memory Deficits and Cholinergic Dysfunction in a Mouse Model of Alzheimer's Disease," Neuron, Jan. 2004; 41: 27-33.
Ojwang et al., Proc. Nat. Acad. Sci. 89 10802-10806, 1992.

(56) References Cited

OTHER PUBLICATIONS

Paxinos et al The Mouse Brain in Stereotactic Coordinates, Acad. Press 2nd Ed. (2001).
Potter, N. T. et al., "Technical standards and guidelines for huntington disease testing," Genetics in Medicine 6:61-65 (2004).
Promega Corporation, T4 DNA Ligase Blue/White Cloning Qualified, Part# 9PIM180, Revised Apr. 2005, 2 pgs.
Promega Corporation, T4 DNA Polymerase(a), Part# 9PIM421, Revised May 2004, 2 pgs.
Qiagen, Qiaex II Handbook, Feb. 1999, 24 pgs.
Qiagen, Rneasy Mini Handbook, 3rd Edition, Jun. 2001, 116 pgs.
R&D Systems, ß -Secretase Activity Kit, Catalog No. FP002, Aug. 2002, 2 pgs.
Roberds et al., "BACE knockout mice are healthy despite lacking the primary ß -secretase activity in brain: implications for Alzheimer's disease therapeutics," Human Molecular Genetics, Jun. 2001; 10(12): 1317-1324.
Ryu, Biomaterials 26: 319-326 (2005).
Salehi et al., J. Neural Transm. 106 955-986 (1999).
Sapru et al., Annual Meeting Soc. Neurosci. Abstract 297.9, XP001204566 (2003).
Sarver et al., Science 247, 1222-1225 (1990).
Scanlon et al., Proc. Nat. Acad. Sci. 88, 10591-10595 (1995).
Schenk, "Amyloid-ß immunotherapy for Alzheimer's disease: the end of the beginning," Nature Reviews—Neuroscience, Oct. 2002; 3: 824-828.
Scherr et al., Cell Cycle 2(3) 251-257 (2003).
Serra et at., Medical Image Analysis 1(4) 317-329 (1996).
Singer et al., Nat. Neurosci. 8(10) 1343-1349 (ePub Aug. 28, 2005).
Stackman et al., Experimental Neurology 184, 510-520 (2003).
Strategene, AAV Helper-Free System, Instruction Manual, Catalog #240071, #240074, #240075, Revision #084007i, Aug. 2004, 50 pgs.
Strategene, pBluescript® II Phagemid Vectors, Instruction Manual, Catalog #212205, #212206, #212207, #212208, Revision #083001m, Aug. 2003, 35 pgs.
Sullenger, Science 262, p. 1566 (Dec. 3, 1993).
Taira et al., Nucl. Acid. Res. 19(19) 5125-5130 (1991).
Thompson et al., Nucl. Acid. Res. 23(12), 2259 (1995).
Timson et al., Biochem J 363:515-520 (2002).
Tuscjl Lab, "The siRNA user guide," Revised May 2004, [online]. Retrieved on Nov. 29, 2005. Retrieved from the Internet: <URL:rockefeller.edu/labheads/tuschl/sirna.html>, 6 pgs.
Ui-Tei et al., "Guidelines for the selection of highly effective siRNA sequences for mammalian and chick RNA interference,"; Nucleic Acids Research (2004); vol. 32, No. 3, pp. 936-948.
Valbonesi et al., Ttransf. And Apheresis Sci. 30: 153-156 (2004).
Van Bilsen et al., "Identification and allele-specific silencing of the mutant huntingtin allele in Huntington's disease patient-derived fibroblasts," Human Gene Therapy, vol. 19, pp. 710-718 (2008).
Vassar et al., Science 286 735-741 (1999).
Ventura et al., Nucl. Acid. Res. 21(14) 3249-3255 (1993).
Vickers, Journal of Bio. Chemistry, vol. 278, No. 9 7108-7118 (2003).
Watanabe et al., J. Mol. Cel. Card. 37 (3) 691-698 (2004).
Weerasinghe et al., J. Virol. 65(10), 5531-3334 (1991).
Whitesell et al., Proc. Nat. Acad. Sci. 90: 4665-4669 (1993).
Xia et al., Nat. Biotech. 20, 1006-1010 (2002).
Xia et al., Nat. Med. 10(8) 816-820 (2004).
Yamamoto et al., Cell 101, 57-66 (2000).
Yu et al., Proc. Nat. Acad. Sci. 90 6340-6344 (1993).
Yu et al., Proc. Nat. Acad. Sci. 99 6047-6052 (2002).
Zhang et al., "Global Non-Viral Gene Transfer to the Primate Brain Following Intravenous Administration," Molecular Therapy, Jan. 2003; 7(1): 11-18.
Zhang et al., "In vivo knockdown of gene expression in brain cancer with intravenous RNAi in adult rats," J. Gene Med., 2003; 5:1039-1045; published online Aug. 4, 2003.
Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.
National Center for Biotechnology Information, National Library of Medicine, National Institutes of Health, GenBank Locus NM_000202, Accession No. NM_000202, "*Homo sapiens* iduronate 2-sulfatase (Hunter syndrome)(ID), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=5360215>; 8 pgs.
National Center for Biotechnology Information, National Library of Medicine, National Institutes of Health, GenBank Locus NM_000203, Accession No. NM_000203, "*Homo sapiens* iduronidase, alpha-L-(IDUA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=40354208>; 6 pgs.
National Center for Biotechnology Information, National Library of Medicine, National Institutes of Health, GenBank Locus NM_000235, Accession No. NM_000235, "*Homo sapiens* lipase A, lysosomal acid, cholesterol esterase (Wolman disease) (LIPA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4557720>; 4 pgs.
National Center for Biotechnology Information, National Library of Medicine, National Institutes of Health, GenBank Locus NM_000262, Accession No. NM_000262, "*Homo sapiens* N-acetylgalactosaminidase, alpha- (NAGA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=4557780>; 4 pgs.
National Center for Biotechnology Information, National Library of Medicine, National Institutes of Health, GenBank Locus NM_000263, Accession No. NM_000263, "*Homo sapiens* N-acetylglucosaminidase, alpha-(Sanfilippo disease) (IIIB)(NAGLU), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=40548380>; 4 pgs.
National Center for Biotechnology Information, National Library of Medicine, National Institutes of Health, GenBank Locus NM_000310, Accession No. NM_000310, "*Homo sapiens* palmitoyl-protein thioesterase 1 (ceroid-lipofuscinosis, neuronal 1, infantile) (PPT1), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=4506030>; 4 pgs.
National Center for Biotechnology Information, National Library of Medicine, National Institutes of Health, GenBank Locus NM_000332, Accession No. NM_000332, "*Homo sapiens* spinocerebellar ataxia 1 (olivopontocerebellar ataxia 1, autosomal dominant, ataxin 1) (SCA1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4506792>; 7 pgs.
National Center for Biotechnology Information, National Library of Medicine, National Institutes of Health, GenBank Locus NM_000345, Accession No. NM_000345, "*Homo sapiens* synuclein, alpha (nonA4 component of amyloid precursor) (SNCA), transcript variant NACP140, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=6806896>; 6 pgs.
National Center for Biotechnology Information, National Library of Medicine, National Institutes of Health, GenBank Locus NM_000404, Accession No. NM_000404, "*Homo sapiens* glactosidase, beta 1 (GLB1), transcript variant 179423, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=10834965>; 5 pgs.
National Center for Biotechnology Information, National Library of Medicine, National Institutes of Health, GenBank Locus NM_000434, Accession No. NM_000434, "*Homo sapiens* sialidase

(56) References Cited

OTHER PUBLICATIONS 1 (lysosomal sialidase)(NEU1), mRNA," [online]. Bethesda, MD [retrieved on Mar. 5, 2009]. Retrieved from the Internet<URL:http://www.ncbi.nlm.nih. gov/entrez/viewer.fcgi?db=nucleotide&val=40806202>; 5 pgs.

National Center for Biotechnology Information, National Library of Medicine, National Institutes of Health, GenBank Locus NM_000487, Accession No. NM_000487, "*Homo sapiens* arysulfatase A (ARSA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=7262293>; 4 pgs.

National Center for Biotechnology Information, National Library of Medicine, National Institutes of Health, GenBank Locus NM_000512, Accession No. NM_000512, "*Homo sapiens* galactosamine (N-acetyl)-6-sulfate sulfatase (Morquio syndrome, mucopolysaccharidosis type IVA), (GALNS), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=9945384>; 4 pgs.

National Center for Biotechnology Information, National Library of Medicine, National Institutes of Health, GenBank Locus NM_000520, Accession No. NM_000520, "*Homo sapiens* hexosaminidase A (alpha polypeptide) (HEXA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13128865>; 5 pgs.

National Center for Biotechnology Information, National Library of Medicine, National Institutes of Health, GenBank Locus NM_000521, Accession No. NM_000521, "*Homo sapiens* hexosaminidase B (beta polypeptide) (HEXB), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=13128866>; 6 pgs.

National Center for Biotechnology Information, National Library of Medicine, National Institutes of Health, GenBank Locus NM_000528, Accession No. NM_000528, "*Homo sapiens* mannosidase, alpha, class 2B, member 1 (MAN2B1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=10834967>; 4 pgs.

National Center for Biotechnology Information, National Library of Medicine, National Institutes of Health, GenBank Locus NM_000543, Accession No. NM_000543, "*Homo sapiens* sphingomyelin phosphodiesterase 1 acid lysosomal (acid sphingomyelinase) (SMPD1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=40254417>; 5 pgs.

National Center for Biotechnology Information, National Library of Medicine, National Institutes of Health, GenBank Locus NM_002076, Accession No. NM_002076, "*Homo sapiens* glucosamine (N-acetyl)-6-sulfatase (Sanfilippo disease)(IIID)(GNS), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=42490755>; 7 pgs.

National Center for Biotechnology Information, National Library of Medicine, National Institutes of Health, GenBank Locus NM_002778, Accession No. NM_0002778, Accession No. NM_000169, "*Homo sapiens* glactosidase, alpha (GLA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4504008>; 4 pgs.

National Center for Biotechnology Information, National Library of Medicine, National Institutes of Health, GenBank Locus NM_002778, Accession No. NM_002778, "*Homo sapiens* prosaposin (variant Gaucher disease and variant metachromatic leukodystrophy) (PSAP), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=11386146>; 8 pgs.

National Center for Biotechnology Information, National Library of Medicine, National Institutes of Health, GenBank Locus NM_004315, Accession No. NM_004315, "*Homo sapiens* N-acylsphingosine amidohydrolase (acid ceramidase) 1 (ASAHI), transcript variant 2, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=30089929>; 5 pgs.

National Center for Biotechnology Information, National Library of Medicine, National Institutes of Health, GenBank Locus NM_004993, Accession No. NM_004993, "*Homo sapiens* Machado-Joseph disease (spinocerebellar ataxia 3, olivopontocerebellar ataxia 3, autosomal dominant, ataxin 3) (MJD), transcript variant 1, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518018>; 9 pgs.

National Center for Biotechnology Information, National Library of Medicine, National Institutes of Health, GenBank Locus NM_005908, Accession No. NM_005908, "*Homo sapiens* mannosidase, beta A, lyosomal (MANBA), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24797157>; 4 pgs.

National Center for Biotechnology Information, National Library of Medicine, National Institutes of Health, GenBank Locus NM_007308, Accession No. NM_007308, "*Homo sapiens* synuclein, alpha (nonA4 component of amyloid precursor) (SNCA), transcript variant NACP112, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=6806897>; 5 pgs.

National Center for Biotechnology Information, National Library of Medicine, National Institutes of Health, GenBank Locus NM_009124, Accession No. NM_009124, "Definition," [online]. Bethesda, MD [retrieved on Mar. 5, 2009]. Retrieved from the Internet<URL:http://www.ncbi.nlm.nih.gov/entrez/viewer.fcgi?db=nucleotide&val=33636695>; 5 pgs.

National Center for Biotechnology Information, National Library of Medicine, National Institutes of Health, GenBank Locus NM_011792, Accession No. NM_011792, Version NM_011792.2, "*Mus musculus* beta-site APP cleaving enzyme 1 (Bace 1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=31981411>; 5 pgs.

National Center for Biotechnology Information, National Library of Medicine, National Institutes of Health, GenBank Locus NM_011792.2, Accession No. NM_011792, "*Mus musculus* beta-site APP cleaving enzyme (Bace), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=6857758>; 4 pgs.

National Center for Biotechnology Information, National Library of Medicine, National Institutes of Health, GenBank Locus NM_012104, Accession No. NM_012104, "*Homo sapiens* beta-site APP-cleaving enzyme 1 (BACE1), transcript variant a, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255011>; 8 pgs.

National Center for Biotechnology Information, National Library of Medicine, National Institutes of Health, GenBank Locus NM_012104, Accession No. NM_012104, Version NM_012104.2, "*Homo sapiens* beta-site APP-cleaving enzyme (BACE), transcript variant a, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040369>; 10 pgs.

National Center for Biotechnology Information, National Library of Medicine, National Institutes of Health, GenBank Locus NM_013995, Accession No. NM_013995, "*Homo sapiens* lysosomal-associated membrane protein 2 (LAMP2), transcript vari-

(56) References Cited

OTHER PUBLICATIONS ant LAMP2B, mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=7669502>; 6 pgs.

National Center for Biotechnology Information, National Library of Medicine, National Institutes of Health, GenBank Locus NM_030660, Accession No. NM_030660, "*Homo sapiens* Machado-Joseph disease (spinocerebellar ataxia 3, olivopontocerebellar ataxia 3, autosomal dominant, ataxin 3) (MJD), transcript variant 2, mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=13518012>; 8 pgs.

National Center for Biotechnology Information, National Library of Medicine, National Institutes of Health, GenBank Locus NM_032520, Accession No. NM_032520, "*Homo sapiens* N-acetylglucosamine-1-phosphotransferase, gamma subunit (GNPTAG), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=42476109>; 5 pgs.

National Center for Biotechnology Information, National Library of Medicine, National Institutes of Health, GenBank Locus NM_138971, Accession No. NM_138971, "*Homo sapiens* beta-site APP-cleaving enzyme 1 (BACE1), transcript variant c, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255012>; 8 pgs.

National Center for Biotechnology Information, National Library of Medicine, National Institutes of Health, GenBank Locus NM_138971, Accession No. NM_138971, Version NM_138971.1, "*Homo sapiens* beta-site APP-cleaving enzyme (BACE), transcript variant c, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040363>; 10 pgs.

National Center for Biotechnology Information, National Library of Medicine, National Institutes of Health, GenBank Locus NM_138972, Accession No. NM_138972, "*Homo sapiens* beta-site APP-cleaving enzyme 1 (BACE1), transcript variant b, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255013>; 8 pgs.

National Center for Biotechnology Information, National Library of Medicine, National Institutes of Health, GenBank Locus NM_138972, Accession No. NM_138972, Version NM_138972.1, "*Homo sapiens* beta-site APP-cleaving enzyme (BACE), transcript variant b, mRNA," [online]. Bethesda, MD [retrieved on Mar. 5, 2009]. Retrieved from the Internet<URl:http://www.ncbi.nlm.nih.gov/entrez/viewer.fcgi?db=nucleotide&val=21040365>; 10 pgs.

National Center for Biotechnology Information, National Library of Medicine, National Institutes of Health, GenBank Locus NM_138973, Accession No. NM_138973, "*Homo sapiens* beta-site APP-cleaving enzyme 1 (BACE1), transcript variant d, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=46255014>; 8 pgs.

National Center for Biotechnology Information, National Library of Medicine, National Institutes of Health, GenBank Locus NM_138973, Accession No. NM_138973, Version NM_138973.1, "*Homo sapiens* beta-site APP-cleaving enzyme (BACE), transcript variant d, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=21040367>; 10 pgs.

National Center for Biotechnology Information, National Library of Medicine, National Institutes of Health, GenBank Locus U24233, Accession No. U24233, "*Mus musculus* huntingtin (Hd) mRNA, complete cds," [online]. Bethesda, MD [retrieved on Mar. 5, 2009]. Retrieved from the Internet: <URL:http://www.ncbi.nlm.nih.gov/entrez/viewer.fcgi?db=nucleotide&val=902003>; 5 pgs.

Lee e tal., "Tsix, a gene antisense to Xist at the X-inactivation centre," Nat Genet (1999); 21(4):400-404.

Okuda et al. "Verification of 525 coding SNPs in 179 hypertension candidate genes in the Japanese population: identification of 159 SNPs in 93 genes," J. Human Genetics (2002); Vo. 47, pp. 387-394.

Database SNP (online) (Jul. 13, 2000) XP002522351, retrieved from NCBI Database Accession No. ss1556778, ref. SNP rs363099.

Database SNP (online) (Aug. 20, 2004) XP002522352, retrieved from NCBI Database Accession No. ss23893221, ref. SNP rs363099.

Database SNP (online) (Sep. 6, 2000) XP002522353, retrieved from NCBI Database Accession No. ss1303522, ref. SNP rs362331.

Tjelle et al., "Taking electroporation-based delivery of DNA vaccination into humans: a generic clincial protocol," Methods in Molecular Biology; Humana Press 2008; vol. 423, pp. 497-507.

Ambion, Inc., Siport siRNA electrospun Buffer (Part No. AM8990G, AM8900, AM8991) Protocol 2008 (18 pages).

Eun et al., "Molecular beacons: a new approach to plant virus detection," Phytopathology (2000); vol. 90, No. 3, pp. 269-275.

National Center for Biotechnology Information, National Library of Medicine, National Institutes of Health, GenBank Locus AH003045, Accession No. AH003045, "*Homo sapiens* huntingtin (HD) gene, exon 1," [online]. Bethesda, MD [retrieved on Mar. 5, 2009]. Retrieved from the Internet<URL:http://www.ncbi.nlm.nih.gov/entrez/viewer.fcgi?db=nucleotide&val=663286>; 42 pgs.

National Center for Biotechnology Information, National Library of Medicine, National Institutes of Health, GenBank Locus NM_000027, Accession No. NM_000027, "*Homo sapiens* aspartylglucosaminidase (AGA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=32313568>; 4 pgs.

National Center for Biotechnology Information, National Library of Medicine, National Institutes of Health, GenBank Locus NM_000046, Accession No. NM_000046, "*Homo sapiens* arylsulfatase B (ARSB), transcript variant 1, mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=38569404>; 4 pgs.

National Center for Biotechnology Information, National Library of Medicine, National Institutes of Health, GenBank Locus NM_000049, Accession No. NM_000049, "*Homo sapiens* aspartoacylase (aminoacylase 1, Canavan disease) (ASPA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557334>; 4 pgs.

National Center for Biotechnology Information, National Library of Medicine, National Institutes of Health, GenBank Locus NM_000147, Accession No. NM_000147, "*Homo sapiens* fucosidase, alpha-L1, tissue (FUCA1), mRNA," [online]. Bethesda, MD [retrieved on Mar. 5, 2009]. Retrieved from the Internet:<URL:http://www.ncbi.nlm.nih.gov/entrez/viewer.fcgi?db=nucleotide&val=24475878>; 3 pgs.

National Center for Biotechnology Information, National Library of Medicine, National Institutes of Health, GenBank Locus NM_000152, Accession No. NM_000152, "*Homo sapiens* glucosidase, alpha; acid (Pompe disease, glycogen storage disease type II) (GAA), mRNA," [online]. Bethesda, MD [retrieved on Mar. 5, 2009]. Retrieved from the Internet: <URL:http://www.ncbi.nlm.nih.gov/entrez/viewer.fcgi?db=nucleotide&val=11496988>, 4 pgs.

National Center for Biotechnology Information, National Library of Medicine, National Institutes of Health, GenBank Locus NM_00153, Accession No. NM_000153, "*Homo sapiens* galactosylceramidase (Krabbe disease) (GALC), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557612>, 5 pgs.

National Center for Biotechnology Information, National Library of Medicine, National Institutes of Health, GenBank Locus NM_000157, Accession No. NM_000157, "*Homo sapiens* glucosidase, beta; acid (includes glucosylceramidase) (GBA), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4503934>; 7 pgs.

National Center for Biotechnology Information, National Library of Medicine, National Institutes of Health, GenBank Locus

(56) References Cited

OTHER PUBLICATIONS

NM_000158, Accession No. NM_000158, "*Homo sapiens* glucan (1, 4-alpha-), branching enzyme 1 (glucogen branching enzyme, Andersen disease, glycogen storage disease trype (IV)(GBE1), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4557618>; 2 pgs.

National Center for Biotechnology Information, National Library of Medicine, National Institutes of Health, GenBank Locus NM_000181, Accession No. NM_000181, "*Homo sapiens* glucuronidase, beta (GUSB), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=4504222>; 4 pgs.

National Center for Biotechnology Information, National Library of Medicine, National Institutes of Health, GenBank Locus NM_000199, Accession No. NM_000199, "*Homo sapiens* N-sulfoglucosamine sulfohydrolase (sulfamidase) (SGSH), mRNA," [online]. Bethesda, MD [retrieved on Mar. 5, 2009]. Retrieved from the Internet<URL:http://www.ncbi.nlm.nih.gov/entrez/viewer.fcgi?db=nucleotide&val=31543619>, 3 pgs.

* cited by examiner

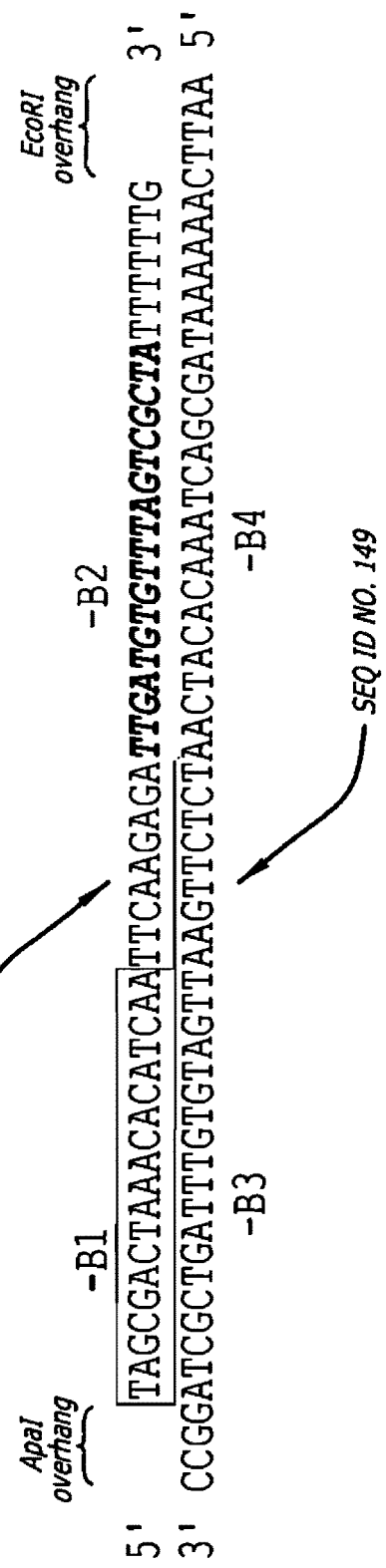

SEQUENCE LISTING

```
<160> NUMBER OF SEQ ID NOS: 149

<210> SEQ ID NO 1
<211> LENGTH: 19
<212> TYPE: DNA
<213> ORGANISM: Homo sapiens

<400> SEQUENCE: 1
aggccttcat agcgaacct                                              19

<210> SEQ ID NO 2
```

```
<211> LENGTH: 19
<212> TYPE: DNA
<213> ORGANISM: Homo sapiens

<400> SEQUENCE: 2
aggccttcac agcgaacct                                                      19

<210> SEQ ID NO 3
<211> LENGTH: 19
<212> TYPE: DNA
<213> ORGANISM: Homo sapiens

<400> SEQUENCE: 3
aaatgtgctg ttaggctta                                                      19

<210> SEQ ID NO 4
<211> LENGTH: 19
<212> TYPE: DNA
<213> ORGANISM: Homo sapiens

<400> SEQUENCE: 4
aaatgtgctc ttaggctta                                                      19

<210> SEQ ID NO 5
<211> LENGTH: 19
<212> TYPE: DNA
<213> ORGANISM: Homo sapiens

<400> SEQUENCE: 5
caataaagga agccttgcc                                                      19

<210> SEQ ID NO 6
<211> LENGTH: 19
<212> TYPE: DNA
<213> ORGANISM: Homo sapiens

<400> SEQUENCE: 6
caataaaggc agccttgcc                                                      19

<210> SEQ ID NO 7
<211> LENGTH: 19
<212> TYPE: DNA
<213> ORGANISM: Homo sapiens

<400> SEQUENCE: 7
agggtttctc cgctcagcc                                                      19

<210> SEQ ID NO 8
<211> LENGTH: 19
<212> TYPE: DNA
<213> ORGANISM: Homo sapiens

<400> SEQUENCE: 8
agggtttctt cgctcagcc                                                      19

<210> SEQ ID NO 9
<211> LENGTH: 19
<212> TYPE: DNA
<213> ORGANISM: Homo sapiens

<400> SEQUENCE: 9
gagcaggaga acgacacct                                                      19
```

```
<210> SEQ ID NO 10
<211> LENGTH: 19
<212> TYPE: DNA
<213> ORGANISM: Homo sapiens

<400> SEQUENCE: 10
gagcaggagc acgacacct                                                   19

<210> SEQ ID NO 11
<211> LENGTH: 19
<212> TYPE: DNA
<213> ORGANISM: Homo sapiens

<400> SEQUENCE: 11
taagaggaac aaataaagc                                                   19

<210> SEQ ID NO 12
<211> LENGTH: 19
<212> TYPE: DNA
<213> ORGANISM: Homo sapiens

<400> SEQUENCE: 12
taagaggaat aaataaagc                                                   19

<210> SEQ ID NO 13
<211> LENGTH: 19
<212> TYPE: DNA
<213> ORGANISM: Homo sapiens

<400> SEQUENCE: 13
gggacagtac ttcaacgct                                                   19

<210> SEQ ID NO 14
<211> LENGTH: 19
<212> TYPE: DNA
<213> ORGANISM: Homo sapiens

<400> SEQUENCE: 14
gggacagtaa ttcaacgct                                                   19

<210> SEQ ID NO 15
<211> LENGTH: 19
<212> TYPE: DNA
<213> ORGANISM: Homo sapiens

<400> SEQUENCE: 15
tccctcatct actgtgtgc                                                   19

<210> SEQ ID NO 16
<211> LENGTH: 19
<212> TYPE: DNA
<213> ORGANISM: Homo sapiens

<400> SEQUENCE: 16
tccctcatcc actgtgtgc                                                   19

<210> SEQ ID NO 17
<211> LENGTH: 19
<212> TYPE: DNA
<213> ORGANISM: Homo sapiens

<400> SEQUENCE: 17
ccgcatcaac acactaggc                                                   19
```

```
<210> SEQ ID NO 18
<211> LENGTH: 19
<212> TYPE: DNA
<213> ORGANISM: Homo sapiens

<400> SEQUENCE: 18
ccgcatcaat acactaggc                                                19

<210> SEQ ID NO 19
<211> LENGTH: 19
<212> TYPE: DNA
<213> ORGANISM: Homo sapiens

<400> SEQUENCE: 19
ctggtgacgc agcccctcg                                                19

<210> SEQ ID NO 20
<211> LENGTH: 19
<212> TYPE: DNA
<213> ORGANISM: Homo sapiens

<400> SEQUENCE: 20
ctggtgacgt agcccctcg                                                19

<210> SEQ ID NO 21
<211> LENGTH: 19
<212> TYPE: DNA
<213> ORGANISM: Homo sapiens

<400> SEQUENCE: 21
aagcccatat caccggctg                                                19

<210> SEQ ID NO 22
<211> LENGTH: 19
<212> TYPE: DNA
<213> ORGANISM: Homo sapiens

<400> SEQUENCE: 22
aagcccatac caccggctg                                                19

<210> SEQ ID NO 23
<211> LENGTH: 19
<212> TYPE: DNA
<213> ORGANISM: Homo sapiens

<400> SEQUENCE: 23
ggccttcata gcgaacctg                                                19

<210> SEQ ID NO 24
<211> LENGTH: 19
<212> TYPE: DNA
<213> ORGANISM: Homo sapiens

<400> SEQUENCE: 24
gccttcatag cgaacctga                                                19

<210> SEQ ID NO 25
<211> LENGTH: 19
<212> TYPE: DNA
<213> ORGANISM: Homo sapiens

<400> SEQUENCE: 25
aaggccttca tagcgaacc                                                19
```

```
<210> SEQ ID NO 26
<211> LENGTH: 19
<212> TYPE: DNA
<213> ORGANISM: Homo sapiens

<400> SEQUENCE: 26
aaaggccttc atagcgaac                                                  19

<210> SEQ ID NO 27
<211> LENGTH: 19
<212> TYPE: DNA
<213> ORGANISM: Homo sapiens

<400> SEQUENCE: 27
ggccttcaca gcgaacctg                                                  19

<210> SEQ ID NO 28
<211> LENGTH: 19
<212> TYPE: DNA
<213> ORGANISM: Homo sapiens

<400> SEQUENCE: 28
gccttcacag cgaacctga                                                  19

<210> SEQ ID NO 29
<211> LENGTH: 19
<212> TYPE: DNA
<213> ORGANISM: Homo sapiens

<400> SEQUENCE: 29
aaggccttca cagcgaacc                                                  19

<210> SEQ ID NO 30
<211> LENGTH: 19
<212> TYPE: DNA
<213> ORGANISM: Homo sapiens

<400> SEQUENCE: 30
aaaggccttc acagcgaac                                                  19

<210> SEQ ID NO 31
<211> LENGTH: 19
<212> TYPE: DNA
<213> ORGANISM: Homo sapiens

<400> SEQUENCE: 31
taaatgtgct gttaggctt                                                  19

<210> SEQ ID NO 32
<211> LENGTH: 19
<212> TYPE: DNA
<213> ORGANISM: Homo sapiens

<400> SEQUENCE: 32
ctaaatgtgc tgttaggct                                                  19

<210> SEQ ID NO 33
<211> LENGTH: 19
<212> TYPE: DNA
<213> ORGANISM: Homo sapiens

<400> SEQUENCE: 33
```

```
aatgtgctgt taggcttac                                                19
```

<210> SEQ ID NO 34
<211> LENGTH: 19
<212> TYPE: DNA
<213> ORGANISM: Homo sapiens

<400> SEQUENCE: 34

```
atgtgctgtt aggcttact                                                19
```

<210> SEQ ID NO 35
<211> LENGTH: 19
<212> TYPE: DNA
<213> ORGANISM: Homo sapiens

<400> SEQUENCE: 35

```
taaatgtgct cttaggctt                                                19
```

<210> SEQ ID NO 36
<211> LENGTH: 19
<212> TYPE: DNA
<213> ORGANISM: Homo sapiens

<400> SEQUENCE: 36

```
ctaaatgtgc tcttaggct                                                19
```

<210> SEQ ID NO 37
<211> LENGTH: 19
<212> TYPE: DNA
<213> ORGANISM: Homo sapiens

<400> SEQUENCE: 37

```
aatgtgctct taggcttac                                                19
```

<210> SEQ ID NO 38
<211> LENGTH: 19
<212> TYPE: DNA
<213> ORGANISM: Homo sapiens

<400> SEQUENCE: 38

```
atgtgctctt aggcttact                                                19
```

<210> SEQ ID NO 39
<211> LENGTH: 19
<212> TYPE: DNA
<213> ORGANISM: Homo sapiens

<400> SEQUENCE: 39

```
gcaataaagg aagccttgc                                                19
```

<210> SEQ ID NO 40
<211> LENGTH: 19
<212> TYPE: DNA
<213> ORGANISM: Homo sapiens

<400> SEQUENCE: 40

```
cgcaataaag gaagccttg                                                19
```

<210> SEQ ID NO 41
<211> LENGTH: 19
<212> TYPE: DNA
<213> ORGANISM: Homo sapiens

<400> SEQUENCE: 41

```
aataaaggaa gccttgcct                                               19

<210> SEQ ID NO 42
<211> LENGTH: 19
<212> TYPE: DNA
<213> ORGANISM: Homo sapiens

<400> SEQUENCE: 42
ataaaggaag ccttgcctt                                               19

<210> SEQ ID NO 43
<211> LENGTH: 19
<212> TYPE: DNA
<213> ORGANISM: Homo sapiens

<400> SEQUENCE: 43
gcaataaagg cagccttgc                                               19

<210> SEQ ID NO 44
<211> LENGTH: 19
<212> TYPE: DNA
<213> ORGANISM: Homo sapiens

<400> SEQUENCE: 44
cgcaataaag gcagccttg                                               19

<210> SEQ ID NO 45
<211> LENGTH: 19
<212> TYPE: DNA
<213> ORGANISM: Homo sapiens

<400> SEQUENCE: 45
aataaaggca gccttgcct                                               19

<210> SEQ ID NO 46
<211> LENGTH: 19
<212> TYPE: DNA
<213> ORGANISM: Homo sapiens

<400> SEQUENCE: 46
ataaaggcag ccttgcctt                                               19

<210> SEQ ID NO 47
<211> LENGTH: 19
<212> TYPE: DNA
<213> ORGANISM: Homo sapiens

<400> SEQUENCE: 47
gagggtttct ccgctcagc                                               19

<210> SEQ ID NO 48
<211> LENGTH: 19
<212> TYPE: DNA
<213> ORGANISM: Homo sapiens

<400> SEQUENCE: 48
ggagggtttc tccgctcag                                               19

<210> SEQ ID NO 49
<211> LENGTH: 19
<212> TYPE: DNA
<213> ORGANISM: Homo sapiens
```

```
<400> SEQUENCE: 49
gggtttctcc gctcagcct                                          19

<210> SEQ ID NO 50
<211> LENGTH: 19
<212> TYPE: DNA
<213> ORGANISM: Homo sapiens

<400> SEQUENCE: 50
ggtttctccg ctcagcctt                                          19

<210> SEQ ID NO 51
<211> LENGTH: 19
<212> TYPE: DNA
<213> ORGANISM: Homo sapiens

<400> SEQUENCE: 51
gagggtttct tcgctcagc                                          19

<210> SEQ ID NO 52
<211> LENGTH: 19
<212> TYPE: DNA
<213> ORGANISM: Homo sapiens

<400> SEQUENCE: 52
ggagggtttc ttcgctcag                                          19

<210> SEQ ID NO 53
<211> LENGTH: 19
<212> TYPE: DNA
<213> ORGANISM: Homo sapiens

<400> SEQUENCE: 53
gggtttcttc gctcagcct                                          19

<210> SEQ ID NO 54
<211> LENGTH: 19
<212> TYPE: DNA
<213> ORGANISM: Homo sapiens

<400> SEQUENCE: 54
ggtttcttcg ctcagcctt                                          19

<210> SEQ ID NO 55
<211> LENGTH: 19
<212> TYPE: DNA
<213> ORGANISM: Homo sapiens

<400> SEQUENCE: 55
ggagcaggag aacgacacc                                          19

<210> SEQ ID NO 56
<211> LENGTH: 19
<212> TYPE: DNA
<213> ORGANISM: Homo sapiens

<400> SEQUENCE: 56
cggagcagga gaacgacac                                          19

<210> SEQ ID NO 57
<211> LENGTH: 19
<212> TYPE: DNA
<213> ORGANISM: Homo sapiens
```

<400> SEQUENCE: 57
agcaggagaa cgacacctc                                            19

<210> SEQ ID NO 58
<211> LENGTH: 19
<212> TYPE: DNA
<213> ORGANISM: Homo sapiens

<400> SEQUENCE: 58
gcaggagaac gacacctcg                                            19

<210> SEQ ID NO 59
<211> LENGTH: 19
<212> TYPE: DNA
<213> ORGANISM: Homo sapiens

<400> SEQUENCE: 59
ggagcaggag cacgacacc                                            19

<210> SEQ ID NO 60
<211> LENGTH: 19
<212> TYPE: DNA
<213> ORGANISM: Homo sapiens

<400> SEQUENCE: 60
cggagcagga gcacgacac                                            19

<210> SEQ ID NO 61
<211> LENGTH: 19
<212> TYPE: DNA
<213> ORGANISM: Homo sapiens

<400> SEQUENCE: 61
agcaggagca cgacacctc                                            19

<210> SEQ ID NO 62
<211> LENGTH: 19
<212> TYPE: DNA
<213> ORGANISM: Homo sapiens

<400> SEQUENCE: 62
gcaggagcac gacacctcg                                            19

<210> SEQ ID NO 63
<211> LENGTH: 19
<212> TYPE: DNA
<213> ORGANISM: Homo sapiens

<400> SEQUENCE: 63
ttaagaggaa caaataaag                                            19

<210> SEQ ID NO 64
<211> LENGTH: 19
<212> TYPE: DNA
<213> ORGANISM: Homo sapiens

<400> SEQUENCE: 64
attaagagga acaaataaa                                            19

<210> SEQ ID NO 65
<211> LENGTH: 19
<212> TYPE: DNA

```
<213> ORGANISM: Homo sapiens

<400> SEQUENCE: 65
aagaggaaca aataaagct                                                   19

<210> SEQ ID NO 66
<211> LENGTH: 19
<212> TYPE: DNA
<213> ORGANISM: Homo sapiens

<400> SEQUENCE: 66
agaggaacaa ataaagctg                                                   19

<210> SEQ ID NO 67
<211> LENGTH: 19
<212> TYPE: DNA
<213> ORGANISM: Homo sapiens

<400> SEQUENCE: 67
ttaagaggaa taaataaag                                                   19

<210> SEQ ID NO 68
<211> LENGTH: 19
<212> TYPE: DNA
<213> ORGANISM: Homo sapiens

<400> SEQUENCE: 68
attaagagga taaataaa                                                    19

<210> SEQ ID NO 69
<211> LENGTH: 19
<212> TYPE: DNA
<213> ORGANISM: Homo sapiens

<400> SEQUENCE: 69
aagaggaata aataaagct                                                   19

<210> SEQ ID NO 70
<211> LENGTH: 19
<212> TYPE: DNA
<213> ORGANISM: Homo sapiens

<400> SEQUENCE: 70
agaggaataa ataaagctg                                                   19

<210> SEQ ID NO 71
<211> LENGTH: 19
<212> TYPE: DNA
<213> ORGANISM: Homo sapiens

<400> SEQUENCE: 71
ggacagtact tcaacgcta                                                   19

<210> SEQ ID NO 72
<211> LENGTH: 19
<212> TYPE: DNA
<213> ORGANISM: Homo sapiens

<400> SEQUENCE: 72
gacagtactt caacgctag                                                   19

<210> SEQ ID NO 73
<211> LENGTH: 19
```

<212> TYPE: DNA
<213> ORGANISM: Homo sapiens

<400> SEQUENCE: 73
ggggacagta cttcaacgc                                            19

<210> SEQ ID NO 74
<211> LENGTH: 19
<212> TYPE: DNA
<213> ORGANISM: Homo sapiens

<400> SEQUENCE: 74
tggggacagt acttcaacg                                            19

<210> SEQ ID NO 75
<211> LENGTH: 19
<212> TYPE: DNA
<213> ORGANISM: Homo sapiens

<400> SEQUENCE: 75
ggacagtaat tcaacgcta                                            19

<210> SEQ ID NO 76
<211> LENGTH: 19
<212> TYPE: DNA
<213> ORGANISM: Homo sapiens

<400> SEQUENCE: 76
gacagtaatt caacgctag                                            19

<210> SEQ ID NO 77
<211> LENGTH: 19
<212> TYPE: DNA
<213> ORGANISM: Homo sapiens

<400> SEQUENCE: 77
ggggacagta attcaacgc                                            19

<210> SEQ ID NO 78
<211> LENGTH: 19
<212> TYPE: DNA
<213> ORGANISM: Homo sapiens

<400> SEQUENCE: 78
tggggacagt aattcaacg                                            19

<210> SEQ ID NO 79
<211> LENGTH: 19
<212> TYPE: DNA
<213> ORGANISM: Homo sapiens

<400> SEQUENCE: 79
ctccctcatc tactgtgtg                                            19

<210> SEQ ID NO 80
<211> LENGTH: 19
<212> TYPE: DNA
<213> ORGANISM: Homo sapiens

<400> SEQUENCE: 80
gctccctcat ctactgtgt                                            19

<210> SEQ ID NO 81

```
<211> LENGTH: 19
<212> TYPE: DNA
<213> ORGANISM: Homo sapiens

<400> SEQUENCE: 81
ccctcatcta ctgtgtgca                                               19

<210> SEQ ID NO 82
<211> LENGTH: 19
<212> TYPE: DNA
<213> ORGANISM: Homo sapiens

<400> SEQUENCE: 82
cctcatctac tgtgtgcac                                               19

<210> SEQ ID NO 83
<211> LENGTH: 19
<212> TYPE: DNA
<213> ORGANISM: Homo sapiens

<400> SEQUENCE: 83
ctccctcatc cactgtgtg                                               19

<210> SEQ ID NO 84
<211> LENGTH: 19
<212> TYPE: DNA
<213> ORGANISM: Homo sapiens

<400> SEQUENCE: 84
gctccctcat ccactgtgt                                               19

<210> SEQ ID NO 85
<211> LENGTH: 19
<212> TYPE: DNA
<213> ORGANISM: Homo sapiens

<400> SEQUENCE: 85
ccctcatcca ctgtgtgca                                               19

<210> SEQ ID NO 86
<211> LENGTH: 19
<212> TYPE: DNA
<213> ORGANISM: Homo sapiens

<400> SEQUENCE: 86
cctcatccac tgtgtgcac                                               19

<210> SEQ ID NO 87
<211> LENGTH: 19
<212> TYPE: DNA
<213> ORGANISM: Homo sapiens

<400> SEQUENCE: 87
accgcatcaa cacactagg                                               19

<210> SEQ ID NO 88
<211> LENGTH: 19
<212> TYPE: DNA
<213> ORGANISM: Homo sapiens

<400> SEQUENCE: 88
taccgcatca acacactag                                               19
```

```
<210> SEQ ID NO 89
<211> LENGTH: 19
<212> TYPE: DNA
<213> ORGANISM: Homo sapiens

<400> SEQUENCE: 89
cgcatcaaca cactaggct                                                19

<210> SEQ ID NO 90
<211> LENGTH: 19
<212> TYPE: DNA
<213> ORGANISM: Homo sapiens

<400> SEQUENCE: 90
gcatcaacac actaggctg                                                19

<210> SEQ ID NO 91
<211> LENGTH: 19
<212> TYPE: DNA
<213> ORGANISM: Homo sapiens

<400> SEQUENCE: 91
accgcatcaa tacactagg                                                19

<210> SEQ ID NO 92
<211> LENGTH: 19
<212> TYPE: DNA
<213> ORGANISM: Homo sapiens

<400> SEQUENCE: 92
taccgcatca atacactag                                                19

<210> SEQ ID NO 93
<211> LENGTH: 19
<212> TYPE: DNA
<213> ORGANISM: Homo sapiens

<400> SEQUENCE: 93
cgcatcaata cactaggct                                                19

<210> SEQ ID NO 94
<211> LENGTH: 19
<212> TYPE: DNA
<213> ORGANISM: Homo sapiens

<400> SEQUENCE: 94
gcatcaatac actaggctg                                                19

<210> SEQ ID NO 95
<211> LENGTH: 19
<212> TYPE: DNA
<213> ORGANISM: Homo sapiens

<400> SEQUENCE: 95
cctggtgacg cagcccctc                                                19

<210> SEQ ID NO 96
<211> LENGTH: 19
<212> TYPE: DNA
<213> ORGANISM: Homo sapiens

<400> SEQUENCE: 96
tcctggtgac gcagcccct                                                19
```

```
<210> SEQ ID NO 97
<211> LENGTH: 19
<212> TYPE: DNA
<213> ORGANISM: Homo sapiens

<400> SEQUENCE: 97
tggtgacgca gccctcgt                                                19

<210> SEQ ID NO 98
<211> LENGTH: 19
<212> TYPE: DNA
<213> ORGANISM: Homo sapiens

<400> SEQUENCE: 98
ggtgacgcag ccctcgtg                                                19

<210> SEQ ID NO 99
<211> LENGTH: 19
<212> TYPE: DNA
<213> ORGANISM: Homo sapiens

<400> SEQUENCE: 99
cctggtgacg tagcccctc                                               19

<210> SEQ ID NO 100
<211> LENGTH: 19
<212> TYPE: DNA
<213> ORGANISM: Homo sapiens

<400> SEQUENCE: 100
tcctggtgac gtagcccct                                               19

<210> SEQ ID NO 101
<211> LENGTH: 19
<212> TYPE: DNA
<213> ORGANISM: Homo sapiens

<400> SEQUENCE: 101
tggtgacgta gccctcgt                                                19

<210> SEQ ID NO 102
<211> LENGTH: 19
<212> TYPE: DNA
<213> ORGANISM: Homo sapiens

<400> SEQUENCE: 102
ggtgacgtag ccctcgtg                                                19

<210> SEQ ID NO 103
<211> LENGTH: 19
<212> TYPE: DNA
<213> ORGANISM: Homo sapiens

<400> SEQUENCE: 103
gaagcccata tcaccggct                                               19

<210> SEQ ID NO 104
<211> LENGTH: 19
<212> TYPE: DNA
<213> ORGANISM: Homo sapiens

<400> SEQUENCE: 104
ggaagcccat atcaccggc                                               19
```

<210> SEQ ID NO 105
<211> LENGTH: 19
<212> TYPE: DNA
<213> ORGANISM: Homo sapiens

<400> SEQUENCE: 105
agcccatatc accggctgc                                                19

<210> SEQ ID NO 106
<211> LENGTH: 19
<212> TYPE: DNA
<213> ORGANISM: Homo sapiens

<400> SEQUENCE: 106
gcccatatca ccggctgct                                                19

<210> SEQ ID NO 107
<211> LENGTH: 19
<212> TYPE: DNA
<213> ORGANISM: Homo sapiens

<400> SEQUENCE: 107
gaagcccata ccaccggct                                                19

<210> SEQ ID NO 108
<211> LENGTH: 19
<212> TYPE: DNA
<213> ORGANISM: Homo sapiens

<400> SEQUENCE: 108
ggaagcccat accaccggc                                                19

<210> SEQ ID NO 109
<211> LENGTH: 19
<212> TYPE: DNA
<213> ORGANISM: Homo sapiens

<400> SEQUENCE: 109
agcccatacc accggctgc                                                19

<210> SEQ ID NO 110
<211> LENGTH: 19
<212> TYPE: DNA
<213> ORGANISM: Homo sapiens

<400> SEQUENCE: 110
gcccatacca ccggctgct                                                19

<210> SEQ ID NO 111
<211> LENGTH: 19
<212> TYPE: DNA
<213> ORGANISM: Homo sapiens

<400> SEQUENCE: 111
tagcgactaa acacatcaa                                                19

<210> SEQ ID NO 112
<211> LENGTH: 53
<212> TYPE: DNA
<213> ORGANISM: Homo sapiens

<400> SEQUENCE: 112

```
aggccttcat agcgaaccctt tcaagagaag gttcgctatg aaggcctttt ttg    53
```

<210> SEQ ID NO 113
<211> LENGTH: 54
<212> TYPE: DNA
<213> ORGANISM: Homo sapiens

<400> SEQUENCE: 113

```
tagcgactaa acacatcaat tcaagagatt gatgtgttta gtcgctattt tttg    54
```

<210> SEQ ID NO 114
<211> LENGTH: 19
<212> TYPE: DNA
<213> ORGANISM: Homo sapiens

<400> SEQUENCE: 114

```
aaatgtgctg tgaggctta                                          19
```

<210> SEQ ID NO 115
<211> LENGTH: 19
<212> TYPE: DNA
<213> ORGANISM: Homo sapiens

<400> SEQUENCE: 115

```
gctactaaat gtgctgtta                                          19
```

<210> SEQ ID NO 116
<211> LENGTH: 19
<212> TYPE: DNA
<213> ORGANISM: Homo sapiens

<400> SEQUENCE: 116

```
aaatgtgctc tgaggctta                                          19
```

<210> SEQ ID NO 117
<211> LENGTH: 19
<212> TYPE: DNA
<213> ORGANISM: Homo sapiens

<400> SEQUENCE: 117

```
gctactaaat gtgctctta                                          19
```

<210> SEQ ID NO 118
<211> LENGTH: 19
<212> TYPE: DNA
<213> ORGANISM: Homo sapiens

<400> SEQUENCE: 118

```
gtttggaggg tttctccgc                                          19
```

<210> SEQ ID NO 119
<211> LENGTH: 19
<212> TYPE: DNA
<213> ORGANISM: Homo sapiens

<400> SEQUENCE: 119

```
agggtttctc ctctcagcc                                          19
```

<210> SEQ ID NO 120
<211> LENGTH: 19
<212> TYPE: DNA
<213> ORGANISM: Homo sapiens

<400> SEQUENCE: 120
agggtttctc cactcagcc                                              19

<210> SEQ ID NO 121
<211> LENGTH: 19
<212> TYPE: DNA
<213> ORGANISM: Homo sapiens

<400> SEQUENCE: 121
gtttggaggg tttcttcgc                                              19

<210> SEQ ID NO 122
<211> LENGTH: 19
<212> TYPE: DNA
<213> ORGANISM: Homo sapiens

<400> SEQUENCE: 122
agggtttctt ctctcagcc                                              19

<210> SEQ ID NO 123
<211> LENGTH: 19
<212> TYPE: DNA
<213> ORGANISM: Homo sapiens

<400> SEQUENCE: 123
agggtttctt cactcagcc                                              19

<210> SEQ ID NO 124
<211> LENGTH: 19
<212> TYPE: DNA
<213> ORGANISM: Homo sapiens

<400> SEQUENCE: 124
ggacagtaca tcaacgcta                                              19

<210> SEQ ID NO 125
<211> LENGTH: 19
<212> TYPE: DNA
<213> ORGANISM: Homo sapiens

<400> SEQUENCE: 125
gagatgggga cagtacttc                                              19

<210> SEQ ID NO 126
<211> LENGTH: 19
<212> TYPE: DNA
<213> ORGANISM: Homo sapiens

<400> SEQUENCE: 126
ggggacagta cttaaacgc                                              19

<210> SEQ ID NO 127
<211> LENGTH: 19
<212> TYPE: DNA
<213> ORGANISM: Homo sapiens

<400> SEQUENCE: 127
ggacagtaag tcaacgcta                                              19

<210> SEQ ID NO 128
<211> LENGTH: 19
<212> TYPE: DNA
<213> ORGANISM: Homo sapiens

```
<400> SEQUENCE: 128
gagatgggga cagtaattc                                                19

<210> SEQ ID NO 129
<211> LENGTH: 19
<212> TYPE: DNA
<213> ORGANISM: Homo sapiens

<400> SEQUENCE: 129
ggggacagta attaaacgc                                                19

<210> SEQ ID NO 130
<211> LENGTH: 19
<212> TYPE: DNA
<213> ORGANISM: Homo sapiens

<400> SEQUENCE: 130
gcctgctccc tcatctact                                                19

<210> SEQ ID NO 131
<211> LENGTH: 19
<212> TYPE: DNA
<213> ORGANISM: Homo sapiens

<400> SEQUENCE: 131
tccctcatct actgggtgc                                                19

<210> SEQ ID NO 132
<211> LENGTH: 19
<212> TYPE: DNA
<213> ORGANISM: Homo sapiens

<400> SEQUENCE: 132
tccctcatct acggtgtgc                                                19

<210> SEQ ID NO 133
<211> LENGTH: 19
<212> TYPE: DNA
<213> ORGANISM: Homo sapiens

<400> SEQUENCE: 133
gcctgctccc tcatccact                                                19

<210> SEQ ID NO 134
<211> LENGTH: 19
<212> TYPE: DNA
<213> ORGANISM: Homo sapiens

<400> SEQUENCE: 134
tccctcatcc actgggtgc                                                19

<210> SEQ ID NO 135
<211> LENGTH: 19
<212> TYPE: DNA
<213> ORGANISM: Homo sapiens

<400> SEQUENCE: 135
tccctcatcc acggtgtgc                                                19

<210> SEQ ID NO 136
<211> LENGTH: 21
<212> TYPE: DNA
<213> ORGANISM: Homo sapiens
```

```
<400> SEQUENCE: 136
gagaugggga caguacuuct t                                              21

<210> SEQ ID NO 137
<211> LENGTH: 21
<212> TYPE: DNA
<213> ORGANISM: Homo sapiens

<400> SEQUENCE: 137
gaaguacugu ccccaucuct t                                              21

<210> SEQ ID NO 138
<211> LENGTH: 21
<212> TYPE: DNA
<213> ORGANISM: Homo sapiens

<400> SEQUENCE: 138
ggacaguaag ucaacgcuat t                                              21

<210> SEQ ID NO 139
<211> LENGTH: 21
<212> TYPE: DNA
<213> ORGANISM: Homo sapiens

<400> SEQUENCE: 139
uagcguugac uuacuguccc t                                              21

<210> SEQ ID NO 140
<211> LENGTH: 19
<212> TYPE: DNA
<213> ORGANISM: Homo sapiens

<400> SEQUENCE: 140
actcctccac ctttgacgc                                                 19

<210> SEQ ID NO 141
<211> LENGTH: 21
<212> TYPE: DNA
<213> ORGANISM: Homo sapiens

<400> SEQUENCE: 141
gttgctgtag ccaaattcgt t                                              21

<210> SEQ ID NO 142
<211> LENGTH: 40
<212> TYPE: DNA
<213> ORGANISM: Homo sapiens

<400> SEQUENCE: 142
cgcgatcgat ggggacagta cttcaacgct agagatcgcg                          40

<210> SEQ ID NO 143
<211> LENGTH: 26
<212> TYPE: DNA
<213> ORGANISM: Homo sapiens

<400> SEQUENCE: 143
agatattgtt ctttctcgta ttcagg                                         26

<210> SEQ ID NO 144
<211> LENGTH: 21
<212> TYPE: DNA
```

```
<213> ORGANISM: Homo sapiens

<400> SEQUENCE: 144
tgctcactca tttccacctt c                                           21

<210> SEQ ID NO 145
<211> LENGTH: 35
<212> TYPE: DNA
<213> ORGANISM: Homo sapiens

<400> SEQUENCE: 145
agtgcgtggg acagtaattc aacgctagac gcact                            35

<210> SEQ ID NO 146
<211> LENGTH: 27
<212> TYPE: DNA
<213> ORGANISM: Homo sapiens

<400> SEQUENCE: 146
ccttctctcc gtatttaatc tcctgta                                     27

<210> SEQ ID NO 147
<211> LENGTH: 27
<212> TYPE: DNA
<213> ORGANISM: Homo sapiens

<400> SEQUENCE: 147
tcatttccac cttcagctgt tttgtaa                                     27

<210> SEQ ID NO 148
<211> LENGTH: 62
<212> TYPE: DNA
<213> ORGANISM: Homo sapiens

<400> SEQUENCE: 148
ccggtccgga agtatcgctt ggaaagttct cttccaagcg atacttccgg aaaaaaactt 60
aa                                                                62

<210> SEQ ID NO 149
<211> LENGTH: 62
<212> TYPE: DNA
<213> ORGANISM: Homo sapiens

<400> SEQUENCE: 149
ccggatcgct gatttgtgta gttaagttct ctaactacac aaatcagcga taaaaaactt 60
aa                                                                62
```

METHODS AND SEQUENCES TO PREFERENTIALLY SUPPRESS EXPRESSION OF MUTATED HUNTINGTIN

CROSS REFERENCE TO RELATED APPLICATIONS

This application is a continuation of a PCT application PCT/US2008/064532 filed on May 22, 2008 which is a continuation-in-part of a PCT application PCT/US07/012259 filed on May 23, 2007, which is a continuation-in-part application and claims the benefit of U.S. patent application Ser. No. 11/439,858, filed on May 24, 2006. This application is also a continuation-in-part of U.S. application Ser. No. 11/478,110 filed on Jun. 28, 2006, which claims the benefit under 35 U.S.C. §119(e) of U.S. Provisional Application No. 60/695,078, filed Jun. 28, 2005.

FIELD OF THE INVENTION

The present invention relates to methods and sequences to preferentially suppress the expression of the mutated huntingtin ("htt") protein over expression of the normal htt protein.

BACKGROUND OF THE INVENTION

Huntington's disease ("HD") is a degenerative brain disorder. It slowly destroys an affected individual's ability to walk, think, talk and reason. Symptoms include changes in cognitive ability, such as impaired short-term memory and a decreased ability to concentrate; changes in mood, such as the development of mood swings, depression and irritability; and changes in coordination and physical movement such as clumsiness, involuntary movements and twitching. These symptoms gradually worsen until HD patients die, approximately 15-20 years after the onset of the disease.

While the biochemical cause of HD is not yet fully understood, it is now known that HD is inherited. Organisms typically inherit two copies of each gene, one from each parent. An individual copy of a gene inherited from one parent is called an allele. With regard to the inheritance of HD, every individual who inherits a HD-causing allele from either parent will develop the disease.

One breakthrough in research regarding HD has been the identification of the mutated gene that causes HD. Based on this breakthrough, researchers and physicians now can predict which individuals will develop HD. Specifically, researchers and physicians can predict which individuals will develop HD by counting the number of "CAG repeats" that exist within an individual's HD genes. If a person has 35 or less CAG repeats in each of their HD gene alleles, that person will not develop HD. If a person has more than 35 CAG repeats in either of their HD gene alleles, that person will develop the disease. The more CAG repeats a person has over 35 in either gene allele, the earlier the person will develop the symptoms of HD.

The HD gene encodes for a protein called "huntingtin" ("htt"). The exact function of htt is not known. However, it is known that the increased number of CAG repeats in HD-causing gene alleles leads to htt proteins with expanded polyglutamine sequences. Expanded polyglutamine sequences in proteins confer novel toxic properties resulting from a tendency of the protein to misfold and form aggregates within brain cells. Thus, suppressing the production of htt in brain cells may provide an avenue to prevent the accumulation of toxic htt in brain cells. This prevention can provide an avenue to further study the physiological mechanisms underlying HD and may also prevent or alleviate the symptoms or occurrence of HD.

While suppressing the production of htt could provide a method to prevent or treat the symptoms of HD, because its functions are not fully understood, fully blocking the expression of this protein may not be desirable. Indeed, animal studies have shown that htt is critical at least during development because animals lacking the protein altogether do not survive. Thus, it would be desirable to preferentially suppress the expression of toxic or mutated htt encoded for by a mutated HD allele while allowing expression of the normal HD allele that encodes for a normal htt protein.

Recent developments in genetic technologies have made the selective suppression of certain alleles and proteins, such as the mutated HD gene allele and the mutated htt protein, possible. Some background in the art is required to understand the potential impact of these technologies. Generally, for a protein to exert an effect, the cell that will use the protein must create it. To create a protein the cell first makes a copy of the protein's gene sequence in the nucleus of the cell. This copy of the gene sequence that encodes for the protein (called messenger RNA ("mRNA")) leaves the nucleus and is trafficked to a region of the cell containing ribosomes. Ribosomes read the sequence of the mRNA and create the protein for which it encodes. This process of new protein synthesis is known as translation. A variety of factors affect the rate and efficiency of protein translation. Among the most significant of these factors is the intrinsic stability of the mRNA itself. If the mRNA is degraded quickly within the cell (such as before it reaches a ribosome), it is unable to serve as a template for new protein translation, thus reducing the cell's ability to create the protein for which it encoded.

Based on the foregoing, the technology of RNA interference ("RNAi") has emerged. RNA interference is, in fact, a naturally occurring mechanism for suppressing gene expression and subsequent protein translation. RNA interference suppresses protein translation by either degrading the mRNA before it can be translated or by binding the mRNA and directly preventing its translation. Generally, RNAi has been used to suppress the expression of both gene alleles that lead to the production of a given protein. However, in some cases, such as those involved in the present invention, it is desirable to suppress the expression of only one allele.

Recently, several single nucleotide polymorphisms ("SNPs") have been identified that can be used to distinguish between the two HD gene alleles in human cells. SNPs are single nucleotide changes in the nucleotide sequence of a given gene. Thus, using RNAi, it is now possible to derive therapeutic agents to specifically suppress the expression of a mutated HD gene allele carrying a SNP. This personal approach can lead to individualized or "directed" therapeutics for HD patients, and provides an avenue to suppress the expression and actions of mutated toxic htt in an attempt to prevent or alleviate the symptoms of HD.

SUMMARY OF THE INVENTION

The present invention describes methods, nucleic acid sequences and molecules, expression cassettes and vectors for using RNA interference ("RNAi") to preferentially suppress the expression of the disease-causing HD gene allele while allowing expression of the normal HD gene allele. Specifically, RNAi is mediated by double stranded RNA ("dsRNA"), short hairpin RNA ("shRNA") or other nucleic acid molecules with similar characteristics. These nucleic acid molecules are processed or cut into smaller pieces by cellular enzymes including Dicer and Drosha. The smaller fragments of the nucleic acid molecules can then be taken up by a protein complex called the RNA-induced silencing complex ("RISC complex") that mediates degradation of specific mRNAs. The RISC complex will degrade mRNA that complementarily base pairs with the nucleic acid molecules it has taken up. In this manner, the mRNA is specifically destroyed, thus preventing the encoded-for protein from being made.

The understanding of the mechanism of RNAi now allows geneticists to create nucleic acid molecules with sequences that are homologous to known gene sequences in order to suppress the expression or formation of certain proteins within a cell. In this invention, individuals (including patients and/or human or non-human research subjects) are screened for the presence of specific single nucleotide polymorphisms (SNPs) in their HD genes until a SNP is found in one of the patient's HD alleles that is not present in the other of the HD patient's alleles. The genetic information obtained from the screening then is used to choose nucleic acid sequences and molecules that are homologous to the mutated htt mRNA sequences. These nucleic acid sequences and molecules are introduced into cells to preferentially suppress the expression of mutated htt protein while allowing expression of the normal htt protein. Preferentially suppressing the expression of the mutated htt protein while allowing expression of the normal htt protein provides beneficial techniques to study the physiological mechanisms underlying HD and may also prevent or treat the symptoms of HD without fully blocking the expression of htt.

One embodiment of the present invention includes methods comprising administering to an individual nucleic acid molecules comprising nucleotide sequences that preferentially suppress the expression of amino acid sequences encoding for mutated huntingtin ("htt") over suppressing the expression of amino acid sequences encoding for normal htt by targeting an area of a Huntington's disease gene that is heterozygous for the presence of one or more single nucleotide polymorphisms wherein the individual has been screened for the heterozygous presence of one or more single nucleotide polymorphisms within the individual's Huntington's genes. In another embodiment of the methods of the present invention, the nucleic acid molecules comprise a nucleotide sequence that comprises SEQ ID NO: 1. In another embodiment of the methods of the present invention, the nucleic acid molecules comprise a nucleotide sequence that comprises SEQ ID NO: 2. In another embodiment of the methods of the present invention, the nucleic acid molecules comprise a nucleotide sequence that comprises SEQ ID NO: 3. In another embodiment of the methods of the present invention, the nucleic acid molecules comprise a nucleotide sequence that comprises SEQ ID NO: 4. In another embodiment of the methods of the present invention, the nucleic acid molecules comprise a nucleotide sequence that comprises SEQ ID NO: 5. In another embodiment of the methods of the present invention, the nucleic acid molecules comprise a nucleotide sequence that comprises SEQ ID NO: 6. In another embodiment of the methods of the present invention, the nucleic acid molecules comprise a nucleotide sequence that comprises SEQ ID NO: 7. In another embodiment of the methods of the present invention, the nucleic acid molecules comprise a nucleotide sequence that comprises SEQ ID NO: 8. In another embodiment of the methods of the present invention, the nucleic acid molecules comprise a nucleotide sequence that comprises SEQ ID NO: 9. In another embodiment of the methods of the present invention, the nucleic acid molecules comprise a nucleotide sequence that comprises SEQ ID NO: 10. In another embodiment of the methods of the present invention, the nucleic acid molecules comprise a nucleotide sequence that comprises SEQ ID NO: 11. In another embodiment of the methods of the present invention, the nucleic acid molecules comprise a nucleotide sequence that comprises SEQ ID NO: 12. In another embodiment of the methods of the present invention, the nucleic acid molecules comprise a nucleotide sequence that comprises SEQ ID NO: 13. In another embodiment of the methods of the present invention, the nucleic acid molecules comprise a nucleotide sequence that comprises SEQ ID NO: 14. In another embodiment of the methods of the present invention, the nucleic acid molecules comprise a nucleotide sequence that comprises SEQ ID NO: 15. In another embodiment of the methods of the present invention, the nucleic acid molecules comprise a nucleotide sequence that comprises SEQ ID NO: 16. In another embodiment of the methods of the present invention, the nucleic acid molecules comprise a nucleotide sequence that comprises SEQ ID NO: 17. In another embodiment of the methods of the present invention, the nucleic acid molecules comprise a nucleotide sequence that comprises SEQ ID NO: 18. In another embodiment of the methods of the present invention, the nucleic acid molecules comprise a nucleotide sequence that comprises SEQ ID NO: 19. In another embodiment of the methods of the present invention, the nucleic acid molecules comprise a nucleotide sequence that comprises SEQ ID NO: 20. In another embodiment of the methods of the present invention, the nucleic acid molecules comprise a nucleotide sequence that comprises SEQ ID NO: 21. In another embodiment of the methods of the present invention, the nucleic acid molecules comprise a nucleotide sequence that comprises SEQ ID NO: 22. In another embodiment of the methods of the present invention, the nucleic acid molecules comprise a nucleotide sequence that comprises SEQ ID NO: 23. In another embodiment of the methods of the present invention, the nucleic acid molecules comprise a nucleotide sequence that comprises SEQ ID NO: 24. In another embodiment of the methods of the present invention, the nucleic acid molecules comprise a nucleotide sequence that comprises SEQ ID NO: 25. In another embodiment of the methods of the present invention, the nucleic acid molecules comprise a nucleotide sequence that comprises SEQ ID NO: 26. In another embodiment of the methods of the present invention, the nucleic acid molecules comprise a nucleotide sequence that comprises SEQ ID NO: 27. In another embodiment of the methods of the present invention, the nucleic acid molecules comprise a nucleotide sequence that comprises SEQ ID NO: 28. In another embodiment of the methods of the present invention, the nucleic acid molecules comprise a nucleotide sequence that comprises SEQ ID NO: 29. In another embodiment of the methods of the present invention, the nucleic acid molecules comprise a nucleotide sequence that comprises SEQ ID NO: 30. In another embodiment of the methods of the present invention, the nucleic acid molecules comprise a nucleotide sequence that comprises SEQ ID NO: 31. In another embodiment of the methods of the present invention, the nucleic acid molecules comprise a nucleotide sequence that comprises SEQ ID NO: 32. In another embodiment of the methods of the present invention, the nucleic acid molecules comprise a nucleotide sequence that comprises SEQ ID NO: 33. In another embodiment of the methods of the present invention, the nucleic acid molecules comprise a nucleotide sequence that comprises SEQ ID NO: 34. In another embodiment of the methods of the present invention, the nucleic acid molecules comprise a nucleotide sequence that comprises SEQ ID NO: 35. In another embodiment of the methods of the present invention, the nucleic acid molecules comprise a nucleotide sequence that comprises SEQ ID NO: 36. In another embodiment of the methods of the present invention, the nucleic acid molecules comprise a nucleotide sequence that comprises SEQ ID NO: 37. In another embodiment of the methods of the present invention, the nucleic acid molecules comprise a nucleotide sequence that comprises SEQ ID NO: 38. In another embodiment of the methods of the present invention, the nucleic acid molecules comprise a nucleotide sequence that comprises SEQ ID NO: 39. In another embodiment of the methods of the present invention, the nucleic acid molecules comprise a nucleotide sequence that comprises SEQ ID NO: 40. In another embodiment of the methods of the present invention, the nucleic acid molecules comprise a nucleotide sequence that comprises SEQ ID NO: 41. In another embodiment of the methods of the present invention, the nucleic acid molecules comprise a nucleotide sequence that comprises SEQ ID NO: 42. In another embodiment of the methods of the present invention, the nucleic acid molecules comprise a nucleotide sequence that comprises SEQ ID NO: 43. In another embodiment of the methods of the present invention, the nucleic acid molecules comprise a nucleotide sequence that comprises SEQ ID NO: 44. In another embodiment of the methods of the present invention, the nucleic acid molecules comprise a nucleotide sequence that comprises SEQ ID NO: 45. In another embodiment of the methods of the present invention, the nucleic acid molecules comprise a nucleotide sequence that comprises SEQ ID NO: 46. In another embodiment of the methods of the present invention, the nucleic acid molecules comprise a nucleotide sequence that comprises SEQ ID NO: 47. In another embodiment of the methods of the present invention, the nucleic acid molecules comprise a nucleotide sequence that comprises SEQ ID NO: 48. In another embodiment of the methods of the present invention, the nucleic acid molecules comprise a nucleotide sequence that comprises SEQ ID NO: 49. In another embodiment of the methods of the present invention, the nucleic acid molecules comprise a nucleotide sequence that comprises SEQ ID NO: 50. In another embodiment of the methods of the present invention, the nucleic acid molecules comprise a nucleotide sequence that comprises SEQ ID NO: 51. In another embodiment of the methods of the present invention, the nucleic acid molecules comprise a nucleotide sequence that comprises SEQ ID NO: 52. In another embodiment of the methods of the present invention, the nucleic acid molecules comprise a nucleotide sequence that comprises SEQ ID NO: 53. In another embodiment of the methods of the present invention, the nucleic acid molecules comprise a nucleotide sequence that comprises SEQ ID NO: 54. In another embodiment of the methods of the present invention, the nucleic acid molecules comprise a nucleotide sequence that comprises SEQ ID NO: 55. In another embodiment of the methods of the present invention, the nucleic acid molecules comprise a nucleotide sequence that comprises SEQ ID NO: 56. In another embodiment of the methods of the present invention, the nucleic acid molecules comprise a nucleotide sequence that comprises SEQ ID NO: 57. In another embodiment of the methods of the present invention, the nucleic acid molecules comprise a nucleotide sequence that comprises SEQ ID NO: 58. In another embodiment of the methods of the present invention, the nucleic acid molecules comprise a nucleotide sequence that comprises SEQ ID NO: 59. In another embodiment of the methods of the present invention, the nucleic acid molecules comprise a nucleotide sequence that comprises SEQ ID NO: 60. In another embodiment of the methods of the present invention, the nucleic acid molecules comprise a nucleotide sequence that comprises SEQ ID NO: 61. In another embodiment of the methods of the present invention, the nucleic acid molecules comprise a nucleotide sequence that comprises SEQ ID NO: 62. In another embodiment of the methods of the present invention, the nucleic acid molecules comprise a nucleotide sequence that comprises SEQ ID NO: 63. In another embodiment of the methods of the present invention, the nucleic acid molecules comprise a nucleotide sequence that comprises SEQ ID NO: 64. In another embodiment of the methods of the present invention, the nucleic acid molecules comprise a nucleotide sequence that comprises SEQ ID NO: 65. In another embodiment of the methods of the present invention, the nucleic acid molecules comprise a nucleotide sequence that comprises SEQ ID NO: 66. In another embodiment of the methods of the present invention, the nucleic acid molecules comprise a nucleotide sequence that comprises SEQ ID NO: 67. In another embodiment of the methods of the present invention, the nucleic acid molecules comprise a nucleotide sequence that comprises SEQ ID NO: 68. In another embodiment of the methods of the present invention, the nucleic acid molecules comprise a nucleotide sequence that comprises SEQ ID NO: 69. In another embodiment of the methods of the present invention, the nucleic acid molecules comprise a nucleotide sequence that comprises SEQ ID NO: 70. In another embodiment of the methods of the present invention, the nucleic acid molecules comprise a nucleotide sequence that comprises SEQ ID NO: 71. In another embodiment of the methods of the present invention, the nucleic acid molecules comprise a nucleotide sequence that comprises SEQ ID NO: 72. In another embodiment of the methods of the present invention, the nucleic acid molecules comprise a nucleotide sequence that comprises SEQ ID NO: 73. In another embodiment of the methods of the present invention, the nucleic acid molecules comprise a nucleotide sequence that comprises SEQ ID NO: 74. In another embodiment of the methods of the present invention, the nucleic acid molecules comprise a nucleotide sequence that comprises SEQ ID NO: 75. In another embodiment of the methods of the present invention, the nucleic acid molecules comprise a nucleotide sequence that comprises SEQ ID NO: 76. In another embodiment of the methods of the present invention, the nucleic acid molecules comprise a nucleotide sequence that comprises SEQ ID NO: 77. In another embodiment of the methods of the present invention, the nucleic acid molecules comprise a nucleotide sequence that comprises SEQ ID NO: 78. In another embodiment of the methods of the present invention, the nucleic acid molecules comprise a nucleotide sequence that comprises SEQ ID NO: 79. In another embodiment of the methods of the present invention, the nucleic acid molecules comprise a nucleotide sequence that comprises SEQ ID NO: 80. In another embodiment of the methods of the present invention, the nucleic acid molecules comprise a nucleotide sequence that comprises SEQ ID NO: 81. In another embodiment of the methods of the present invention, the nucleic acid molecules comprise a nucleotide sequence that comprises SEQ ID NO: 82. In another embodiment of the methods of the present invention, the nucleic acid molecules comprise a nucleotide sequence that comprises SEQ ID NO: 83. In another embodiment of the methods of the present invention, the nucleic acid molecules comprise a nucleotide sequence that comprises SEQ ID NO: 84. In another embodiment of the methods of the present invention, the nucleic acid molecules comprise a nucleotide sequence that comprises SEQ ID NO: 85. In another embodiment of the methods of the present invention, the nucleic acid molecules comprise a nucleotide sequence that comprises SEQ ID NO: 86. In another embodiment of the methods of the present invention, the nucleic acid molecules comprise a nucleotide sequence that comprises SEQ ID NO: 87. In another embodiment of the methods of the present invention, the nucleic acid molecules comprise a nucleotide sequence that comprises SEQ ID NO: 88. In another embodiment of the methods of the present invention, the nucleic acid molecules comprise a nucleotide sequence that comprises SEQ ID NO: 89. In another embodiment of the methods of the present invention, the nucleic acid molecules comprise a nucleotide sequence that comprises SEQ ID NO: 90. In another embodiment of the methods of the present invention, the nucleic acid molecules comprise a nucleotide sequence that comprises SEQ ID NO: 91. In another embodiment of the methods of the present invention, the nucleic acid molecules comprise a nucleotide sequence that comprises SEQ ID NO: 92. In another embodiment of the methods of the present invention, the nucleic acid molecules comprise a nucleotide sequence that comprises SEQ ID NO: 93. In another embodiment of the methods of the present invention, the nucleic acid molecules comprise a nucleotide sequence that comprises SEQ ID NO: 94. In another embodiment of the methods of the present invention, the nucleic acid molecules comprise a nucleotide sequence that comprises SEQ ID NO: 95. In another embodiment of the methods of the present invention, the nucleic acid molecules comprise a nucleotide sequence that comprises SEQ ID NO: 96. In another embodiment of the methods of the present invention, the nucleic acid molecules comprise a nucleotide sequence that comprises SEQ ID NO: 97. In another embodiment of the methods of the present invention, the nucleic acid molecules comprise a nucleotide sequence that comprises SEQ ID NO: 98. In another embodiment of the methods of the present invention, the nucleic acid molecules comprise a nucleotide sequence that comprises SEQ ID NO: 99. In another embodiment of the methods of the present invention, the nucleic acid molecules comprise a nucleotide sequence that comprises SEQ ID NO: 100. In another embodiment of the methods of the present invention, the nucleic acid molecules comprise a nucleotide sequence that comprises SEQ ID NO: 101. In another embodiment of the methods of the present invention, the nucleic acid molecules comprise a nucleotide sequence that comprises SEQ ID NO: 102. In another embodiment of the methods of the present invention, the nucleic acid molecules comprise a nucleotide sequence that comprises SEQ ID NO: 103. In another embodiment of the methods of the present invention, the nucleic acid molecules comprise a nucleotide sequence that comprises SEQ ID NO: 104. In another embodiment of the methods of the present invention, the nucleic acid molecules comprise a nucleotide sequence that comprises SEQ ID NO: 105. In another embodiment of the methods of the present invention, the nucleic acid molecules comprise a nucleotide sequence that comprises SEQ ID NO: 106. In another embodiment of the methods of the present invention, the nucleic acid molecules comprise a nucleotide sequence that comprises SEQ ID NO: 107. In another embodiment of the methods of the present invention, the nucleic acid molecules comprise a nucleotide sequence that comprises SEQ ID NO: 108. In another embodiment of the methods of the present invention, the nucleic acid molecules comprise a nucleotide sequence that comprises SEQ ID NO: 109. In another embodiment of the methods of the present invention, the nucleic acid molecules comprise a nucleotide sequence that comprises SEQ ID NO: 110. In another embodiment of the methods of the present invention, the nucleic acid molecules comprise a nucleotide sequence that comprises SEQ ID NO: 114. In another embodiment of the methods of the present invention, the nucleic acid molecules comprise a nucleotide sequence that comprises SEQ ID NO: 115. In another embodiment of the methods of the present invention, the nucleic acid molecules comprise a nucleotide sequence that comprises SEQ ID NO: 116. In another embodiment of the methods of the present invention, the nucleic acid molecules comprise a nucleotide sequence that comprises SEQ ID NO: 117. In another embodiment of the methods of the present invention, the nucleic acid molecules comprise a nucleotide sequence that comprises SEQ ID NO: 118. In another embodiment of the methods of the present invention, the nucleic acid molecules comprise a nucleotide sequence that comprises SEQ ID NO: 119. In another embodiment of the methods of the present invention, the nucleic acid molecules comprise a nucleotide sequence that comprises SEQ ID NO: 120. In another embodiment of the methods of the present invention, the nucleic acid molecules comprise a nucleotide sequence that comprises SEQ ID NO: 121. In another embodiment of the methods of the present invention, the nucleic acid molecules comprise a nucleotide sequence that comprises SEQ ID NO: 122. In another embodiment of the methods of the present invention, the nucleic acid molecules comprise a nucleotide sequence that comprises SEQ ID NO: 123. In another embodiment of the methods of the present invention, the nucleic acid molecules comprise a nucleotide sequence that comprises SEQ ID NO: 124. In another embodiment of the methods of the present invention, the nucleic acid molecules comprise a nucleotide sequence that comprises SEQ ID NO: 125. In another embodiment of the methods of the present invention, the nucleic acid molecules comprise a nucleotide sequence that comprises SEQ ID NO: 126. In another embodiment of the methods of the present invention, the nucleic acid molecules comprise a nucleotide sequence that comprises SEQ ID NO: 127. In another embodiment of the methods of the present invention, the nucleic acid molecules comprise a nucleotide sequence that comprises SEQ ID NO: 128. In another embodiment of the methods of the present invention, the nucleic acid molecules comprise a nucleotide sequence that comprises SEQ ID NO: 129. In another embodiment of the methods of the present invention, the nucleic acid molecules comprise a nucleotide sequence that comprises SEQ ID NO: 130. In another embodiment of the methods of the present invention, the nucleic acid molecules comprise a nucleotide sequence that comprises SEQ ID NO: 131. In another embodiment of the methods of the present invention, the nucleic acid molecules comprise a nucleotide sequence that comprises SEQ ID NO: 132. In another embodiment of the methods of the present invention, the nucleic acid molecules comprise a nucleotide sequence that comprises SEQ ID NO: 133. In another embodiment of the methods of the present invention, the nucleic acid molecules comprise a nucleotide sequence that comprises SEQ ID NO: 134. In another embodiment of the methods of the present invention, the nucleic acid molecules comprise a nucleotide sequence that comprises SEQ ID NO: 135. In another embodiment of the methods of the present invention, the nucleic acid molecules comprise nucleotide sequences selected from SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof. In another embodiment of the methods of the present invention, the nucleic acid molecules comprise a nucleotide sequence that comprises SEQ ID NO: 1 in shNA format. In another embodiment of the methods of the present invention, the nucleic acid molecules comprise a nucleotide sequence that comprises SEQ ID NO: 2 in shNA format. In another embodiment of the methods of the present invention, the nucleic acid molecules comprise a nucleotide sequence that comprises SEQ ID NO: 3 in shNA format. In another embodiment of the methods of the present invention, the nucleic acid molecules comprise a nucleotide sequence that comprises SEQ ID NO: 4 in shNA format. In another embodiment of the methods of the present invention, the nucleic acid molecules comprise a nucleotide sequence that comprises SEQ ID NO: 5 in shNA format. In another embodiment of the methods of the present invention, the nucleic acid molecules comprise a nucleotide sequence that comprises SEQ ID NO: 6 in shNA format. In another embodiment of the methods of the present invention, the nucleic acid molecules comprise a nucleotide sequence that comprises SEQ ID NO: 7 in shNA format. In another embodiment of the methods of the present invention, the nucleic acid molecules comprise a nucleotide sequence that comprises SEQ ID NO: 8 in shNA format. In another embodiment of the methods of the present invention, the nucleic acid molecules comprise a nucleotide sequence that comprises SEQ ID NO: 9 in shNA format. In another embodiment of the methods of the present invention, the nucleic acid molecules comprise a nucleotide sequence that comprises SEQ ID NO: 10 in shNA format. In another embodiment of the methods of the present invention, the nucleic acid molecules comprise a nucleotide sequence that comprises SEQ ID NO: 11 in shNA format. In another embodiment of the methods of the present invention, the nucleic acid molecules comprise a nucleotide sequence that comprises SEQ ID NO: 12 in shNA format. In another embodiment of the methods of the present invention, the nucleic acid molecules comprise a nucleotide sequence that comprises SEQ ID NO: 13 in shNA format. In another embodiment of the methods of the present invention, the nucleic acid molecules comprise a nucleotide sequence that comprises SEQ ID NO: 14 in shNA format. In another embodiment of the methods of the present invention, the nucleic acid molecules comprise a nucleotide sequence that comprises SEQ ID NO: 15 in shNA format. In another embodiment of the methods of the present invention, the nucleic acid molecules comprise a nucleotide sequence that comprises SEQ ID NO: 16 in shNA format. In another embodiment of the methods of the present invention, the nucleic acid molecules comprise a nucleotide sequence that comprises SEQ ID NO: 17 in shNA format. In another embodiment of the methods of the present invention, the nucleic acid molecules comprise a nucleotide sequence that comprises SEQ ID NO: 18 in shNA format. In another embodiment of the methods of the present invention, the nucleic acid molecules comprise a nucleotide sequence that comprises SEQ ID NO: 19 in shNA format. In another embodiment of the methods of the present invention, the nucleic acid molecules comprise a nucleotide sequence that comprises SEQ ID NO: 20 in shNA format. In another embodiment of the methods of the present invention, the nucleic acid molecules comprise a nucleotide sequence that comprises SEQ ID NO: 21 in shNA format. In another embodiment of the methods of the present invention, the nucleic acid molecules comprise a nucleotide sequence that comprises SEQ ID NO: 22 in shNA format. In another embodiment of the methods of the present invention, the nucleic acid molecules comprise a nucleotide sequence that comprises SEQ ID NO: 23 in shNA format. In another embodiment of the methods of the present invention, the nucleic acid molecules comprise a nucleotide sequence that comprises SEQ ID NO: 24 in shNA format. In another embodiment of the methods of the present invention, the nucleic acid molecules comprise a nucleotide sequence that comprises SEQ ID NO: 25 in shNA format. In another embodiment of the methods of the present invention, the nucleic acid molecules comprise a nucleotide sequence that comprises SEQ ID NO: 26 in shNA format. In another embodiment of the methods of the present invention, the nucleic acid molecules comprise a nucleotide sequence that comprises SEQ ID NO: 27 in shNA format. In another embodiment of the methods of the present invention, the nucleic acid molecules comprise a nucleotide sequence that comprises SEQ ID NO: 28 in shNA format. In another embodiment of the methods of the present invention, the nucleic acid molecules comprise a nucleotide sequence that comprises SEQ ID NO: 29 in shNA format. In another embodiment of the methods of the present invention, the nucleic acid molecules comprise a nucleotide sequence that comprises SEQ ID NO: 30 in shNA format. In another embodiment of the methods of the present invention, the nucleic acid molecules comprise a nucleotide sequence that comprises SEQ ID NO: 31 in shNA format. In another embodiment of the methods of the present invention, the nucleic acid molecules comprise a nucleotide sequence that comprises SEQ ID NO: 32 in shNA format. In another embodiment of the methods of the present invention, the nucleic acid molecules comprise a nucleotide sequence that comprises SEQ ID NO: 33 in shNA format. In another embodiment of the methods of the present invention, the nucleic acid molecules comprise a nucleotide sequence that comprises SEQ ID NO: 34 in shNA format. In another embodiment of the methods of the present invention, the nucleic acid molecules comprise a nucleotide sequence that comprises SEQ ID NO: 35 in shNA format. In another embodiment of the methods of the present invention, the nucleic acid molecules comprise a nucleotide sequence that comprises SEQ ID NO: 36 in shNA format. In another embodiment of the methods of the present invention, the nucleic acid molecules comprise a nucleotide sequence that comprises SEQ ID NO: 37 in shNA format. In another embodiment of the methods of the present invention, the nucleic acid molecules comprise a nucleotide sequence that comprises SEQ ID NO: 38 in shNA format. In another embodiment of the methods of the present invention, the nucleic acid molecules comprise a nucleotide sequence that comprises SEQ ID NO: 39 in shNA format. In another embodiment of the methods of the present invention, the nucleic acid molecules comprise a nucleotide sequence that comprises SEQ ID NO: 40 in shNA format. In another embodiment of the methods of the present invention, the nucleic acid molecules comprise a nucleotide sequence that comprises SEQ ID NO: 41 in shNA format. In another embodiment of the methods of the present invention, the nucleic acid molecules comprise a nucleotide sequence that comprises SEQ ID NO: 42 in shNA format. In another embodiment of the methods of the present invention, the nucleic acid molecules comprise a nucleotide sequence that comprises SEQ ID NO: 43 in shNA format. In another embodiment of the methods of the present invention, the nucleic acid molecules comprise a nucleotide sequence that comprises SEQ ID NO: 44 in shNA format. In another embodiment of the methods of the present invention, the nucleic acid molecules comprise a nucleotide sequence that comprises SEQ ID NO: 45 in shNA format. In another embodiment of the methods of the present invention, the nucleic acid molecules comprise a nucleotide sequence that comprises SEQ ID NO: 46 in shNA format. In another embodiment of the methods of the present invention, the nucleic acid molecules comprise a nucleotide sequence that comprises SEQ ID NO: 47 in shNA format. In another embodiment of the methods of the present invention, the nucleic acid molecules comprise a nucleotide sequence that comprises SEQ ID NO: 48 in shNA format. In another embodiment of the methods of the present invention, the nucleic acid molecules comprise a nucleotide sequence that comprises SEQ ID NO: 49 in shNA format. In another embodiment of the methods of the present invention, the nucleic acid molecules comprise a nucleotide sequence that comprises SEQ ID NO: 50 in shNA format. In another embodiment of the methods of the present invention, the nucleic acid molecules comprise a nucleotide sequence that comprises SEQ ID NO: 51 in shNA format. In another embodiment of the methods of the present invention, the nucleic acid molecules comprise a nucleotide sequence that comprises SEQ ID NO: 52 in shNA format. In another embodiment of the methods of the present invention, the nucleic acid molecules comprise a nucleotide sequence that comprises SEQ ID NO: 53 in shNA format. In another embodiment of the methods of the present invention, the nucleic acid molecules comprise a nucleotide sequence that comprises SEQ ID NO: 54 in shNA format. In another embodiment of the methods of the present invention, the nucleic acid molecules comprise a nucleotide sequence that comprises SEQ ID NO: 55 in shNA format. In another embodiment of the methods of the present invention, the nucleic acid molecules comprise a nucleotide sequence that comprises SEQ ID NO: 56 in shNA format. In another embodiment of the methods of the present invention, the nucleic acid molecules comprise a nucleotide sequence that comprises SEQ ID NO: 57 in shNA format. In another embodiment of the methods of the present invention, the nucleic acid molecules comprise a nucleotide sequence that comprises SEQ ID NO: 58 in shNA format. In another embodiment of the methods of the present invention, the nucleic acid molecules comprise a nucleotide sequence that comprises SEQ ID NO: 59 in shNA format. In another embodiment of the methods of the present invention, the nucleic acid molecules comprise a nucleotide sequence that comprises SEQ ID NO: 60 in shNA format. In another embodiment of the methods of the present invention, the nucleic acid molecules comprise a nucleotide sequence that comprises SEQ ID NO: 61 in shNA format. In another embodiment of the methods of the present invention, the nucleic acid molecules comprise a nucleotide sequence that comprises SEQ ID NO: 62 in shNA format. In another embodiment of the methods of the present invention, the nucleic acid molecules comprise a nucleotide sequence that comprises SEQ ID NO: 63 in shNA format. In another embodiment of the methods of the present invention, the nucleic acid molecules comprise a nucleotide sequence that comprises SEQ ID NO: 64 in shNA format. In another embodiment of the methods of the present invention, the nucleic acid molecules comprise a nucleotide sequence that comprises SEQ ID NO: 65 in shNA format. In another embodiment of the methods of the present invention, the nucleic acid molecules comprise a nucleotide sequence that comprises SEQ ID NO: 66 in shNA format. In another embodiment of the methods of the present invention, the nucleic acid molecules comprise a nucleotide sequence that comprises SEQ ID NO: 67 in shNA format. In another embodiment of the methods of the present invention, the nucleic acid molecules comprise a nucleotide sequence that comprises SEQ ID NO: 68 in shNA format. In another embodiment of the methods of the present invention, the nucleic acid molecules comprise a nucleotide sequence that comprises SEQ ID NO: 69 in shNA format. In another embodiment of the methods of the present invention, the nucleic acid molecules comprise a nucleotide sequence that comprises SEQ ID NO: 70 in shNA format. In another embodiment of the methods of the present invention, the nucleic acid molecules comprise a nucleotide sequence that comprises SEQ ID NO: 71 in shNA format. In another embodiment of the methods of the present invention, the nucleic acid molecules comprise a nucleotide sequence that comprises SEQ ID NO: 72 in shNA format. In another embodiment of the methods of the present invention, the nucleic acid molecules comprise a nucleotide sequence that comprises SEQ ID NO: 73 in shNA format. In another embodiment of the methods of the present invention, the nucleic acid molecules comprise a nucleotide sequence that comprises SEQ ID NO: 74 in shNA format. In another embodiment of the methods of the present invention, the nucleic acid molecules comprise a nucleotide sequence that comprises SEQ ID NO: 75 in shNA format. In another embodiment of the methods of the present invention, the nucleic acid molecules comprise a nucleotide sequence that comprises SEQ ID NO: 76 in shNA format. In another embodiment of the methods of the present invention, the nucleic acid molecules comprise a nucleotide sequence that comprises SEQ ID NO: 77 in shNA format. In another embodiment of the methods of the present invention, the nucleic acid molecules comprise a nucleotide sequence that comprises SEQ ID NO: 78 in shNA format. In another embodiment of the methods of the present invention, the nucleic acid molecules comprise a nucleotide sequence that comprises SEQ ID NO: 79 in shNA format. In another embodiment of the methods of the present invention, the nucleic acid molecules comprise a nucleotide sequence that comprises SEQ ID NO: 80 in shNA format. In another embodiment of the methods of the present invention, the nucleic acid molecules comprise a nucleotide sequence that comprises SEQ ID NO: 81 in shNA format. In another embodiment of the methods of the present invention, the nucleic acid molecules comprise a nucleotide sequence that comprises SEQ ID NO: 82 in shNA format. In another embodiment of the methods of the present invention, the nucleic acid molecules comprise a nucleotide sequence that comprises SEQ ID NO: 83 in shNA format. In another embodiment of the methods of the present invention, the nucleic acid molecules comprise a nucleotide sequence that comprises SEQ ID NO: 84 in shNA format. In another embodiment of the methods of the present invention, the nucleic acid molecules comprise a nucleotide sequence that comprises SEQ ID NO: 85 in shNA format. In another embodiment of the methods of the present invention, the nucleic acid molecules comprise a nucleotide sequence that comprises SEQ ID NO: 86 in shNA format. In another embodiment of the methods of the present invention, the nucleic acid molecules comprise a nucleotide sequence that comprises SEQ ID NO: 87 in shNA format. In another embodiment of the methods of the present invention, the nucleic acid molecules comprise a nucleotide sequence that comprises SEQ ID NO: 88 in shNA format. In another embodiment of the methods of the present invention, the nucleic acid molecules comprise a nucleotide sequence that comprises SEQ ID NO: 89 in shNA format. In another embodiment of the methods of the present invention, the nucleic acid molecules comprise a nucleotide sequence that comprises SEQ ID NO: 90 in shNA format. In another embodiment of the methods of the present invention, the nucleic acid molecules comprise a nucleotide sequence that comprises SEQ ID NO: 91 in shNA format. In another embodiment of the methods of the present invention, the nucleic acid molecules comprise a nucleotide sequence that comprises SEQ ID NO: 92 in shNA format. In another embodiment of the methods of the present invention, the nucleic acid molecules comprise a nucleotide sequence that comprises SEQ ID NO: 93 in shNA format. In another embodiment of the methods of the present invention, the nucleic acid molecules comprise a nucleotide sequence that comprises SEQ ID NO: 94 in shNA format. In another embodiment of the methods of the present invention, the nucleic acid molecules comprise a nucleotide sequence that comprises SEQ ID NO: 95 in shNA format. In another embodiment of the methods of the present invention, the nucleic acid molecules comprise a nucleotide sequence that comprises SEQ ID NO: 96 in shNA format. In another embodiment of the methods of the present invention, the nucleic acid molecules comprise a nucleotide sequence that comprises SEQ ID NO: 97 in shNA format. In another embodiment of the methods of the present invention, the nucleic acid molecules comprise a nucleotide sequence that comprises SEQ ID NO: 98 in shNA format. In another embodiment of the methods of the present invention, the nucleic acid molecules comprise a nucleotide sequence that comprises SEQ ID NO: 99 in shNA format. In another embodiment of the methods of the present invention, the nucleic acid molecules comprise a nucleotide sequence that comprises SEQ ID NO: 100 in shNA format. In another embodiment of the methods of the present invention, the nucleic acid molecules comprise a nucleotide sequence that comprises SEQ ID NO: 101 in shNA format. In another embodiment of the methods of the present invention, the nucleic acid molecules comprise a nucleotide sequence that comprises SEQ ID NO: 102 in shNA format. In another embodiment of the methods of the present invention, the nucleic acid molecules comprise a nucleotide sequence that comprises SEQ ID NO: 103 in shNA format. In another embodiment of the methods of the present invention, the nucleic acid molecules comprise a nucleotide sequence that comprises SEQ ID NO: 104 in shNA format. In another embodiment of the methods of the present invention, the nucleic acid molecules comprise a nucleotide sequence that comprises SEQ ID NO: 105 in shNA format. In another embodiment of the methods of the present invention, the nucleic acid molecules comprise a nucleotide sequence that comprises SEQ ID NO: 106 in shNA format. In another embodiment of the methods of the present invention, the nucleic acid molecules comprise a nucleotide sequence that comprises SEQ ID NO: 107 in shNA format. In another embodiment of the methods of the present invention, the nucleic acid molecules comprise a nucleotide sequence that comprises SEQ ID NO: 108 in shNA format. In another embodiment of the methods of the present invention, the nucleic acid molecules comprise a nucleotide sequence that comprises SEQ ID NO: 109 in shNA format. In another embodiment of the methods of the present invention, the nucleic acid molecules comprise a nucleotide sequence that comprises SEQ ID NO: 110 in shNA format. In another embodiment of the methods of the present invention, the nucleic acid molecules comprise a nucleotide sequence that comprises SEQ ID NO: 114 in shNA format. In another embodiment of the methods of the present invention, the nucleic acid molecules comprise a nucleotide sequence that comprises SEQ ID NO: 115 in shNA format. In another embodiment of the methods of the present invention, the nucleic acid molecules comprise a nucleotide sequence that comprises SEQ ID NO: 116 in shNA format. In another embodiment of the methods of the present invention, the nucleic acid molecules comprise a nucleotide sequence that comprises SEQ ID NO: 117 in shNA format. In another embodiment of the methods of the present invention, the nucleic acid molecules comprise a nucleotide sequence that comprises SEQ ID NO: 118 in shNA format. In another embodiment of the methods of the present invention, the nucleic acid molecules comprise a nucleotide sequence that comprises SEQ ID NO: 119 in shNA format. In another embodiment of the methods of the present invention, the nucleic acid molecules comprise a nucleotide sequence that comprises SEQ ID NO: 120 in shNA format. In another embodiment of the methods of the present invention, the nucleic acid molecules comprise a nucleotide sequence that comprises SEQ ID NO: 121 in shNA format. In another embodiment of the methods of the present invention, the nucleic acid molecules comprise a nucleotide sequence that comprises SEQ ID NO: 122 in shNA format. In another embodiment of the methods of the present invention, the nucleic acid molecules comprise a nucleotide sequence that comprises SEQ ID NO: 123 in shNA format. In another embodiment of the methods of the present invention, the nucleic acid molecules comprise a nucleotide sequence that comprises SEQ ID NO: 124 in shNA format. In another embodiment of the methods of the present invention, the nucleic acid molecules comprise a nucleotide sequence that comprises SEQ ID NO: 125 in shNA format. In another embodiment of the methods of the present invention, the nucleic acid molecules comprise a nucleotide sequence that comprises SEQ ID NO: 126 in shNA format. In another embodiment of the methods of the present invention, the nucleic acid molecules comprise a nucleotide sequence that comprises SEQ ID NO: 127 in shNA format. In another embodiment of the methods of the present invention, the nucleic acid molecules comprise a nucleotide sequence that comprises SEQ ID NO: 128 in shNA format. In another embodiment of the methods of the present invention, the nucleic acid molecules comprise a nucleotide sequence that comprises SEQ ID NO: 129 in shNA format. In another embodiment of the methods of the present invention, the nucleic acid molecules comprise a nucleotide sequence that comprises SEQ ID NO: 130 in shNA format. In another embodiment of the methods of the present invention, the nucleic acid molecules comprise a nucleotide sequence that comprises SEQ ID NO: 131 in shNA format. In another embodiment of the methods of the present invention, the nucleic acid molecules comprise a nucleotide sequence that comprises SEQ ID NO: 132 in shNA format. In another embodiment of the methods of the present invention, the nucleic acid molecules comprise a nucleotide sequence that comprises SEQ ID NO: 133 in shNA format. In another embodiment of the methods of the present invention, the nucleic acid molecules comprise a nucleotide sequence that comprises SEQ ID NO: 134 in shNA format. In another embodiment of the methods of the present invention, the nucleic acid molecules comprise a nucleotide sequence that comprises SEQ ID NO: 135 in shNA format. In another embodiment of the methods of the present invention, the nucleic acid molecules comprise nucleotide sequences selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof in shNA format.

In one embodiment of the methods of the present invention, the nucleic acid molecules are administered to the intrathecal space of the spinal cord. In another embodiment of the methods of the present invention, the nucleic acid molecules are administered intracranially. In one embodiment of the methods of the present invention, the nucleic acid molecules are administered to the striatum.

Another embodiment according to the present invention includes administering nucleic acid sequences of the present invention through an administration system selected from the group consisting of a depot, an infusion pump, an osmotic pump, an interbody pump, a catheter, and combinations thereof. One additional embodiment according to present invention includes administering nucleic acid sequences of the present invention through an implanted pump that controls the delivery of the nucleic acid sequences to an area selected from the group consisting of the intrathecal space of the spinal cord; the striatum; intracranially; and combinations thereof wherein the nucleic acid sequences are delivered in a pharmaceutically effective amount to improve at least one symptom of Huntington's disease.

The present invention also includes nucleic acid molecules. In one embodiment, the nucleic acid molecule comprises a nucleotide sequence that preferentially suppresses the expression of amino acid sequences encoding for mutated huntingtin ("htt") over suppressing the expression of amino acid sequences encoding for normal htt. In one embodiment of the nucleic acid molecules of the present invention, the nucleic acid molecule comprises a nucleotide sequence comprising SEQ ID NO: 1. In another embodiment of the nucleic acid molecules of the present invention, the nucleic acid molecule comprises a nucleotide sequence comprising SEQ ID NO: 2. In another embodiment of the nucleic acid molecules of the present invention, the nucleic acid molecule comprises a nucleotide sequence comprising SEQ ID NO: 3. In another embodiment of the nucleic acid molecules of the present invention, the nucleic acid molecule comprises a nucleotide sequence comprising SEQ ID NO: 4. In another embodiment of the nucleic acid molecules of the present invention, the nucleic acid molecule comprises a nucleotide sequence comprising SEQ ID NO: 5. In another embodiment of the nucleic acid molecules of the present invention, the nucleic acid molecule comprises a nucleotide sequence comprising SEQ ID NO: 6. In another embodiment of the nucleic acid molecules of the present invention, the nucleic acid molecule comprises a nucleotide sequence comprising SEQ ID NO: 7. In another embodiment of the nucleic acid molecules of the present invention, the nucleic acid molecule comprises a nucleotide sequence comprising SEQ ID NO: 8. In another embodiment of the nucleic acid molecules of the present invention, the nucleic acid molecule comprises a nucleotide sequence comprising SEQ ID NO: 9. In another embodiment of the nucleic acid molecules of the present invention, the nucleic acid molecule comprises a nucleotide sequence comprising SEQ ID NO: 10. In another embodiment of the nucleic acid molecules of the present invention, the nucleic acid molecule comprises a nucleotide sequence comprising SEQ ID NO: 11. In another embodiment of the nucleic acid molecules of the present invention, the nucleic acid molecule comprises a nucleotide sequence comprising SEQ ID NO: 12. In another embodiment of the nucleic acid molecules of the present invention, the nucleic acid molecule comprises a nucleotide sequence comprising SEQ ID NO: 13. In another embodiment of the nucleic acid molecules of the present invention, the nucleic acid molecule comprises a nucleotide sequence comprising SEQ ID NO: 14. In another embodiment of the nucleic acid molecules of the present invention, the nucleic acid molecule comprises a nucleotide sequence comprising SEQ ID NO: 15. In another embodiment of the nucleic acid molecules of the present invention, the nucleic acid molecule comprises a nucleotide sequence comprising SEQ ID NO: 16. In another embodiment of the nucleic acid molecules of the present invention, the nucleic acid molecule comprises a nucleotide sequence comprising SEQ ID NO: 17. In another embodiment of the nucleic acid molecules of the present invention, the nucleic acid molecule comprises a nucleotide sequence comprising SEQ ID NO: 18. In another embodiment of the nucleic acid molecules of the present invention, the nucleic acid molecule comprises a nucleotide sequence comprising SEQ ID NO: 19. In another embodiment of the nucleic acid molecules of the present invention, the nucleic acid molecule comprises a nucleotide sequence comprising SEQ ID NO: 20. In another embodiment of the nucleic acid molecules of the present invention, the nucleic acid molecule comprises a nucleotide sequence comprising SEQ ID NO: 21. In another embodiment of the nucleic acid molecules of the present invention, the nucleic acid molecule comprises a nucleotide sequence comprising SEQ ID NO: 22. In another embodiment of the nucleic acid molecules of the present invention, the nucleic acid molecule comprises a nucleotide sequence comprising SEQ ID NO: 23. In another embodiment of the nucleic acid molecules of the present invention, the nucleic acid molecule comprises a nucleotide sequence comprising SEQ ID NO: 24. In another embodiment of the nucleic acid molecules of the present invention, the nucleic acid molecule comprises a nucleotide sequence comprising SEQ ID NO: 25. In another embodiment of the nucleic acid molecules of the present invention, the nucleic acid molecule comprises a nucleotide sequence comprising SEQ ID NO: 26. In another embodiment of the nucleic acid molecules of the present invention, the nucleic acid molecule comprises a nucleotide sequence comprising SEQ ID NO: 27. In another embodiment of the nucleic acid molecules of the present invention, the nucleic acid molecule comprises a nucleotide sequence comprising SEQ ID NO: 28. In another embodiment of the nucleic acid molecules of the present invention, the nucleic acid molecule comprises a nucleotide sequence comprising SEQ ID NO: 29. In another embodiment of the nucleic acid molecules of the present invention, the nucleic acid molecule comprises a nucleotide sequence comprising SEQ ID NO: 30. In another embodiment of the nucleic acid molecules of the present invention, the nucleic acid molecule comprises a nucleotide sequence comprising SEQ ID NO: 31. In another embodiment of the nucleic acid molecules of the present invention, the nucleic acid molecule comprises a nucleotide sequence comprising SEQ ID NO: 32. In another embodiment of the nucleic acid molecules of the present invention, the nucleic acid molecule comprises a nucleotide sequence comprising SEQ ID NO: 33. In another embodiment of the nucleic acid molecules of the present invention, the nucleic acid molecule comprises a nucleotide sequence comprising SEQ ID NO: 34. In another embodiment of the nucleic acid molecules of the present invention, the nucleic acid molecule comprises a nucleotide sequence comprising SEQ ID NO: 35. In another embodiment of the nucleic acid molecules of the present invention, the nucleic acid molecule comprises a nucleotide sequence comprising SEQ ID NO: 36. In another embodiment of the nucleic acid molecules of the present invention, the nucleic acid molecule comprises a nucleotide sequence comprising SEQ ID NO: 37. In another embodiment of the nucleic acid molecules of the present invention, the nucleic acid molecule comprises a nucleotide sequence comprising SEQ ID NO: 38. In another embodiment of the nucleic acid molecules of the present invention, the nucleic acid molecule comprises a nucleotide sequence comprising SEQ ID NO: 39. In another embodiment of the nucleic acid molecules of the present invention, the nucleic acid molecule comprises a nucleotide sequence comprising SEQ ID NO: 40. In another embodiment of the nucleic acid molecules of the present invention, the nucleic acid molecule comprises a nucleotide sequence comprising SEQ ID NO: 41. In another embodiment of the nucleic acid molecules of the present invention, the nucleic acid molecule comprises a nucleotide sequence comprising SEQ ID NO: 42. In another embodiment of the nucleic acid molecules of the present invention, the nucleic acid molecule comprises a nucleotide sequence comprising SEQ ID NO: 43. In another embodiment of the nucleic acid molecules of the present invention, the nucleic acid molecule comprises a nucleotide sequence comprising SEQ ID NO: 44. In another embodiment of the nucleic acid molecules of the present invention, the nucleic acid molecule comprises a nucleotide sequence comprising SEQ ID NO: 45. In another embodiment of the nucleic acid molecules of the present invention, the nucleic acid molecule comprises a nucleotide sequence comprising SEQ ID NO: 46. In another embodiment of the nucleic acid molecules of the present invention, the nucleic acid molecule comprises a nucleotide sequence comprising SEQ ID NO: 47. In another embodiment of the nucleic acid molecules of the present invention, the nucleic acid molecule comprises a nucleotide sequence comprising SEQ ID NO: 48. In another embodiment of the nucleic acid molecules of the present invention, the nucleic acid molecule comprises a nucleotide sequence comprising SEQ ID NO: 49. In another embodiment of the nucleic acid molecules of the present invention, the nucleic acid molecule comprises a nucleotide sequence comprising SEQ ID NO: 50. In another embodiment of the nucleic acid molecules of the present invention, the nucleic acid molecule comprises a nucleotide sequence comprising SEQ ID NO: 51. In another embodiment of the nucleic acid molecules of the present invention, the nucleic acid molecule comprises a nucleotide sequence comprising SEQ ID NO: 52. In another embodiment of the nucleic acid molecules of the present invention, the nucleic acid molecule comprises a nucleotide sequence comprising SEQ ID NO: 53. In another embodiment of the nucleic acid molecules of the present invention, the nucleic acid molecule comprises a nucleotide sequence comprising SEQ ID NO: 54. In another embodiment of the nucleic acid molecules of the present invention, the nucleic acid molecule comprises a nucleotide sequence comprising SEQ ID NO: 55. In another embodiment of the nucleic acid molecules of the present invention, the nucleic acid molecule comprises a nucleotide sequence comprising SEQ ID NO: 56. In another embodiment of the nucleic acid molecules of the present invention, the nucleic acid molecule comprises a nucleotide sequence comprising SEQ ID NO: 57. In another embodiment of the nucleic acid molecules of the present invention, the nucleic acid molecule comprises a nucleotide sequence comprising SEQ ID NO: 58. In another embodiment of the nucleic acid molecules of the present invention, the nucleic acid molecule comprises a nucleotide sequence comprising SEQ ID NO: 59. In another embodiment of the nucleic acid molecules of the present invention, the nucleic acid molecule comprises a nucleotide sequence comprising SEQ ID NO: 60. In another embodiment of the nucleic acid molecules of the present invention, the nucleic acid molecule comprises a nucleotide sequence comprising SEQ ID NO: 61. In another embodiment of the nucleic acid molecules of the present invention, the nucleic acid molecule comprises a nucleotide sequence comprising SEQ ID NO: 62. In another embodiment of the nucleic acid molecules of the present invention, the nucleic acid molecule comprises a nucleotide sequence comprising SEQ ID NO: 63. In another embodiment of the nucleic acid molecules of the present invention, the nucleic acid molecule comprises a nucleotide sequence comprising SEQ ID NO: 64. In another embodiment of the nucleic acid molecules of the present invention, the nucleic acid molecule comprises a nucleotide sequence comprising SEQ ID NO: 65. In another embodiment of the nucleic acid molecules of the present invention, the nucleic acid molecule comprises a nucleotide sequence comprising SEQ ID NO: 66. In another embodiment of the nucleic acid molecules of the present invention, the nucleic acid molecule comprises a nucleotide sequence comprising SEQ ID NO: 67. In another embodiment of the nucleic acid molecules of the present invention, the nucleic acid molecule comprises a nucleotide sequence comprising SEQ ID NO: 68. In another embodiment of the nucleic acid molecules of the present invention, the nucleic acid molecule comprises a nucleotide sequence comprising SEQ ID NO: 69. In another embodiment of the nucleic acid molecules of the present invention, the nucleic acid molecule comprises a nucleotide sequence comprising SEQ ID NO: 70. In another embodiment of the nucleic acid molecules of the present invention, the nucleic acid molecule comprises a nucleotide sequence comprising SEQ ID NO: 71. In another embodiment of the nucleic acid molecules of the present invention, the nucleic acid molecule comprises a nucleotide sequence comprising SEQ ID NO: 72. In another embodiment of the nucleic acid molecules of the present invention, the nucleic acid molecule comprises a nucleotide sequence comprising SEQ ID NO: 73. In another embodiment of the nucleic acid molecules of the present invention, the nucleic acid molecule comprises a nucleotide sequence comprising SEQ ID NO: 74. In another embodiment of the nucleic acid molecules of the present invention, the nucleic acid molecule comprises a nucleotide sequence comprising SEQ ID NO: 75. In another embodiment of the nucleic acid molecules of the present invention, the nucleic acid molecule comprises a nucleotide sequence comprising SEQ ID NO: 76. In another embodiment of the nucleic acid molecules of the present invention, the nucleic acid molecule comprises a nucleotide sequence comprising SEQ ID NO: 77. In another embodiment of the nucleic acid molecules of the present invention, the nucleic acid molecule comprises a nucleotide sequence comprising SEQ ID NO: 78. In another embodiment of the nucleic acid molecules of the present invention, the nucleic acid molecule comprises a nucleotide sequence comprising SEQ ID NO: 79. In another embodiment of the nucleic acid molecules of the present invention, the nucleic acid molecule comprises a nucleotide sequence comprising SEQ ID NO: 80. In another embodiment of the nucleic acid molecules of the present invention, the nucleic acid molecule comprises a nucleotide sequence comprising SEQ ID NO: 81. In another embodiment of the nucleic acid molecules of the present invention, the nucleic acid molecule comprises a nucleotide sequence comprising SEQ ID NO: 82. In another embodiment of the nucleic acid molecules of the present invention, the nucleic acid molecule comprises a nucleotide sequence comprising SEQ ID NO: 83. In another embodiment of the nucleic acid molecules of the present invention, the nucleic acid molecule comprises a nucleotide sequence comprising SEQ ID NO: 84. In another embodiment of the nucleic acid molecules of the present invention, the nucleic acid molecule comprises a nucleotide sequence comprising SEQ ID NO: 85. In another embodiment of the nucleic acid molecules of the present invention, the nucleic acid molecule comprises a nucleotide sequence comprising SEQ ID NO: 86. In another embodiment of the nucleic acid molecules of the present invention, the nucleic acid molecule comprises a nucleotide sequence comprising SEQ ID NO: 87. In another embodiment of the nucleic acid molecules of the present invention, the nucleic acid molecule comprises a nucleotide sequence comprising SEQ ID NO: 88. In another embodiment of the nucleic acid molecules of the present invention, the nucleic acid molecule comprises a nucleotide sequence comprising SEQ ID NO: 89. In another embodiment of the nucleic acid molecules of the present invention, the nucleic acid molecule comprises a nucleotide sequence comprising SEQ ID NO: 90. In another embodiment of the nucleic acid molecules of the present invention, the nucleic acid molecule comprises a nucleotide sequence comprising SEQ ID NO: 91. In another embodiment of the nucleic acid molecules of the present invention, the nucleic acid molecule comprises a nucleotide sequence comprising SEQ ID NO: 92. In another embodiment of the nucleic acid molecules of the present invention, the nucleic acid molecule comprises a nucleotide sequence comprising SEQ ID NO: 93. In another embodiment of the nucleic acid molecules of the present invention, the nucleic acid molecule comprises a nucleotide sequence comprising SEQ ID NO: 94. In another embodiment of the nucleic acid molecules of the present invention, the nucleic acid molecule comprises a nucleotide sequence comprising SEQ ID NO: 95. In another embodiment of the nucleic acid molecules of the present invention, the nucleic acid molecule comprises a nucleotide sequence comprising SEQ ID NO: 96. In another embodiment of the nucleic acid molecules of the present invention, the nucleic acid molecule comprises a nucleotide sequence comprising SEQ ID NO: 97. In another embodiment of the nucleic acid molecules of the present invention, the nucleic acid molecule comprises a nucleotide sequence comprising SEQ ID NO: 98. In another embodiment of the nucleic acid molecules of the present invention, the nucleic acid molecule comprises a nucleotide sequence comprising SEQ ID NO: 99. In another embodiment of the nucleic acid molecules of the present invention, the nucleic acid molecule comprises a nucleotide sequence comprising SEQ ID NO: 100. In another embodiment of the nucleic acid molecules of the present invention, the nucleic acid molecule comprises a nucleotide sequence comprising SEQ ID NO: 101. In another embodiment of the nucleic acid molecules of the present invention, the nucleic acid molecule comprises a nucleotide sequence comprising SEQ ID NO: 102. In another embodiment of the nucleic acid molecules of the present invention, the nucleic acid molecule comprises a nucleotide sequence comprising SEQ ID NO: 103. In another embodiment of the nucleic acid molecules of the present invention, the nucleic acid molecule comprises a nucleotide sequence comprising SEQ ID NO: 104. In another embodiment of the nucleic acid molecules of the present invention, the nucleic acid molecule comprises a nucleotide sequence comprising SEQ ID NO: 105. In another embodiment of the nucleic acid molecules of the present invention, the nucleic acid molecule comprises a nucleotide sequence comprising SEQ ID NO: 106. In another embodiment of the nucleic acid molecules of the present invention, the nucleic acid molecule comprises a nucleotide sequence comprising SEQ ID NO: 107. In another embodiment of the nucleic acid molecules of the present invention, the nucleic acid molecule comprises a nucleotide sequence comprising SEQ ID NO: 108. In another embodiment of the nucleic acid molecules of the present invention, the nucleic acid molecule comprises a nucleotide sequence comprising SEQ ID NO: 109. In another embodiment of the nucleic acid molecules of the present invention, the nucleic acid molecule comprises a nucleotide sequence comprising SEQ ID NO: 110. In another embodiment of the nucleic acid molecules of the present invention, the nucleic acid molecule comprises a nucleotide sequence comprising SEQ ID NO: 114. In another embodiment of the nucleic acid molecules of the present invention, the nucleic acid molecule comprises a nucleotide sequence comprising SEQ ID NO: 115. In another embodiment of the nucleic acid molecules of the present invention, the nucleic acid molecule comprises a nucleotide sequence comprising SEQ ID NO: 116. In another embodiment of the nucleic acid molecules of the present invention, the nucleic acid molecule comprises a nucleotide sequence comprising SEQ ID NO: 117. In another embodiment of the nucleic acid molecules of the present invention, the nucleic acid molecule comprises a nucleotide sequence comprising SEQ ID NO: 118. In another embodiment of the nucleic acid molecules of the present invention, the nucleic acid molecule comprises a nucleotide sequence comprising SEQ ID NO: 119. In another embodiment of the nucleic acid molecules of the present invention, the nucleic acid molecule comprises a nucleotide sequence comprising SEQ ID NO: 120. In another embodiment of the nucleic acid molecules of the present invention, the nucleic acid molecule comprises a nucleotide sequence comprising SEQ ID NO: 121. In another embodiment of the nucleic acid molecules of the present invention, the nucleic acid molecule comprises a nucleotide sequence comprising SEQ ID NO: 122. In another embodiment of the nucleic acid molecules of the present invention, the nucleic acid molecule comprises a nucleotide sequence comprising SEQ ID NO: 123. In another embodiment of the nucleic acid molecules of the present invention, the nucleic acid molecule comprises a nucleotide sequence comprising SEQ ID NO: 124. In another embodiment of the nucleic acid molecules of the present invention, the nucleic acid molecule comprises a nucleotide sequence comprising SEQ ID NO: 125. In another embodiment of the nucleic acid molecules of the present invention, the nucleic acid molecule comprises a nucleotide sequence comprising SEQ ID NO: 126. In another embodiment of the nucleic acid molecules of the present invention, the nucleic acid molecule comprises a nucleotide sequence comprising SEQ ID NO: 127. In another embodiment of the nucleic acid molecules of the present invention, the nucleic acid molecule comprises a nucleotide sequence comprising SEQ ID NO: 128. In another embodiment of the nucleic acid molecules of the present invention, the nucleic acid molecule comprises a nucleotide sequence comprising SEQ ID NO: 129. In another embodiment of the nucleic acid molecules of the present invention, the nucleic acid molecule comprises a nucleotide sequence comprising SEQ ID NO: 130. In another embodiment of the nucleic acid molecules of the present invention, the nucleic acid molecule comprises a nucleotide sequence comprising SEQ ID NO: 131. In another embodiment of the nucleic acid molecules of the present invention, the nucleic acid molecule comprises a nucleotide sequence comprising SEQ ID NO: 132. In another embodiment of the nucleic acid molecules of the present invention, the nucleic acid molecule comprises a nucleotide sequence comprising SEQ ID NO: 133. In another embodiment of the nucleic acid molecules of the present invention, the nucleic acid molecule comprises a nucleotide sequence comprising SEQ ID NO: 134. In another embodiment of the nucleic acid molecules of the present invention, the nucleic acid molecule comprises a nucleotide sequence comprising SEQ ID NO: 135. In another embodiment of the nucleic acid molecules of the present invention, the nucleic acid molecule comprises nucleotide sequences selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof. In another embodiment of the nucleic acid molecules of the present invention, the nucleic acid molecule comprises a nucleotide sequence comprising SEQ ID NO: 1 in shNA format. In another embodiment of the nucleic acid molecules of the present invention, the nucleic acid molecule comprises a nucleotide sequence comprising SEQ ID NO: 2 in shNA format. In another embodiment of the nucleic acid molecules of the present invention, the nucleic acid molecule comprises a nucleotide sequence comprising SEQ ID NO: 3 in shNA format. In another embodiment of the nucleic acid molecules of the present invention, the nucleic acid molecule comprises a nucleotide sequence comprising SEQ ID NO: 4 in shNA format. In another embodiment of the nucleic acid molecules of the present invention, the nucleic acid molecule comprises a nucleotide sequence comprising SEQ ID NO: 5 in shNA format. In another embodiment of the nucleic acid molecules of the present invention, the nucleic acid molecule comprises a nucleotide sequence comprising SEQ ID NO: 6 in shNA format. In another embodiment of the nucleic acid molecules of the present invention, the nucleic acid molecule comprises a nucleotide sequence comprising SEQ ID NO: 7 in shNA format. In another embodiment of the nucleic acid molecules of the present invention, the nucleic acid molecule comprises a nucleotide sequence comprising SEQ ID NO: 8 in shNA format. In another embodiment of the nucleic acid molecules of the present invention, the nucleic acid molecule comprises a nucleotide sequence comprising SEQ ID NO: 9 in shNA format. In another embodiment of the nucleic acid molecules of the present invention, the nucleic acid molecule comprises a nucleotide sequence comprising SEQ ID NO: 10 in shNA format. In another embodiment of the nucleic acid molecules of the present invention, the nucleic acid molecule comprises a nucleotide sequence comprising SEQ ID NO: 11 in shNA format. In another embodiment of the nucleic acid molecules of the present invention, the nucleic acid molecule comprises a nucleotide sequence comprising SEQ ID NO: 12 in shNA format. In another embodiment of the nucleic acid molecules of the present invention, the nucleic acid molecule comprises a nucleotide sequence comprising SEQ ID NO: 13 in shNA format. In another embodiment of the nucleic acid molecules of the present invention, the nucleic acid molecule comprises a nucleotide sequence comprising SEQ ID NO: 14 in shNA format. In another embodiment of the nucleic acid molecules of the present invention, the nucleic acid molecule comprises a nucleotide sequence comprising SEQ ID NO: 15 in shNA format. In another embodiment of the nucleic acid molecules of the present invention, the nucleic acid molecule comprises a nucleotide sequence comprising SEQ ID NO: 16 in shNA format. In another embodiment of the nucleic acid molecules of the present invention, the nucleic acid molecule comprises a nucleotide sequence comprising SEQ ID NO: 17 in shNA format. In another embodiment of the nucleic acid molecules of the present invention, the nucleic acid molecule comprises a nucleotide sequence comprising SEQ ID NO: 18 in shNA format. In another embodiment of the nucleic acid molecules of the present invention, the nucleic acid molecule comprises a nucleotide sequence comprising SEQ ID NO: 19 in shNA format. In another embodiment of the nucleic acid molecules of the present invention, the nucleic acid molecule comprises a nucleotide sequence comprising SEQ ID NO: 20 in shNA format. In another embodiment of the nucleic acid molecules of the present invention, the nucleic acid molecule comprises a nucleotide sequence comprising SEQ ID NO: 21 in shNA format. In another embodiment of the nucleic acid molecules of the present invention, the nucleic acid molecule comprises a nucleotide sequence comprising SEQ ID NO: 22 in shNA format. In another embodiment of the nucleic acid molecules of the present invention, the nucleic acid molecule comprises a nucleotide sequence comprising SEQ ID NO: 23 in shNA format. In another embodiment of the nucleic acid molecules of the present invention, the nucleic acid molecule comprises a nucleotide sequence comprising SEQ ID NO: 24 in shNA format. In another embodiment of the nucleic acid molecules of the present invention, the nucleic acid molecule comprises a nucleotide sequence comprising SEQ ID NO: 25 in shNA format. In another embodiment of the nucleic acid molecules of the present invention, the nucleic acid molecule comprises a nucleotide sequence comprising SEQ ID NO: 26 in shNA format. In another embodiment of the nucleic acid molecules of the present invention, the nucleic acid molecule comprises a nucleotide sequence comprising SEQ ID NO: 27 in shNA format. In another embodiment of the nucleic acid molecules of the present invention, the nucleic acid molecule comprises a nucleotide sequence comprising SEQ ID NO: 28 in shNA format. In another embodiment of the nucleic acid molecules of the present invention, the nucleic acid molecule comprises a nucleotide sequence comprising SEQ ID NO: 29 in shNA format. In another embodiment of the nucleic acid molecules of the present invention, the nucleic acid molecule comprises a nucleotide sequence comprising SEQ ID NO: 30 in shNA format. In another embodiment of the nucleic acid molecules of the present invention, the nucleic acid molecule comprises a nucleotide sequence comprising SEQ ID NO: 31 in shNA format. In another embodiment of the nucleic acid molecules of the present invention, the nucleic acid molecule comprises a nucleotide sequence comprising SEQ ID NO: 32 in shNA format. In another embodiment of the nucleic acid molecules of the present invention, the nucleic acid molecule comprises a nucleotide sequence comprising SEQ ID NO: 33 in shNA format. In another embodiment of the nucleic acid molecules of the present invention, the nucleic acid molecule comprises a nucleotide sequence comprising SEQ ID NO: 34 in shNA format. In another embodiment of the nucleic acid molecules of the present invention, the nucleic acid molecule comprises a nucleotide sequence comprising SEQ ID NO: 35 in shNA format. In another embodiment of the nucleic acid molecules of the present invention, the nucleic acid molecule comprises a nucleotide sequence comprising SEQ ID NO: 36 in shNA format. In another embodiment of the nucleic acid molecules of the present invention, the nucleic acid molecule comprises a nucleotide sequence comprising SEQ ID NO: 37 in shNA format. In another embodiment of the nucleic acid molecules of the present invention, the nucleic acid molecule comprises a nucleotide sequence comprising SEQ ID NO: 38 in shNA format. In another embodiment of the nucleic acid molecules of the present invention, the nucleic acid molecule comprises a nucleotide sequence comprising SEQ ID NO: 39 in shNA format. In another embodiment of the nucleic acid molecules of the present invention, the nucleic acid molecule comprises a nucleotide sequence comprising SEQ ID NO: 40 in shNA format. In another embodiment of the nucleic acid molecules of the present invention, the nucleic acid molecule comprises a nucleotide sequence comprising SEQ ID NO: 41 in shNA format. In another embodiment of the nucleic acid molecules of the present invention, the nucleic acid molecule comprises a nucleotide sequence comprising SEQ ID NO: 42 in shNA format. In another embodiment of the nucleic acid molecules of the present invention, the nucleic acid molecule comprises a nucleotide sequence comprising SEQ ID NO: 43 in shNA format. In another embodiment of the nucleic acid molecules of the present invention, the nucleic acid molecule comprises a nucleotide sequence comprising SEQ ID NO: 44 in shNA format. In another embodiment of the nucleic acid molecules of the present invention, the nucleic acid molecule comprises a nucleotide sequence comprising SEQ ID NO: 45 in shNA format. In another embodiment of the nucleic acid molecules of the present invention, the nucleic acid molecule comprises a nucleotide sequence comprising SEQ ID NO: 46 in shNA format. In another embodiment of the nucleic acid molecules of the present invention, the nucleic acid molecule comprises a nucleotide sequence comprising SEQ ID NO: 47 in shNA format. In another embodiment of the nucleic acid molecules of the present invention, the nucleic acid molecule comprises a nucleotide sequence comprising SEQ ID NO: 48 in shNA format. In another embodiment of the nucleic acid molecules of the present invention, the nucleic acid molecule comprises a nucleotide sequence comprising SEQ ID NO: 49 in shNA format. In another embodiment of the nucleic acid molecules of the present invention, the nucleic acid molecule comprises a nucleotide sequence comprising SEQ ID NO: 50 in shNA format. In another embodiment of the nucleic acid molecules of the present invention, the nucleic acid molecule comprises a nucleotide sequence comprising SEQ ID NO: 51 in shNA format. In another embodiment of the nucleic acid molecules of the present invention, the nucleic acid molecule comprises a nucleotide sequence comprising SEQ ID NO: 52 in shNA format. In another embodiment of the nucleic acid molecules of the present invention, the nucleic acid molecule comprises a nucleotide sequence comprising SEQ ID NO: 53 in shNA format. In another embodiment of the nucleic acid molecules of the present invention, the nucleic acid molecule comprises a nucleotide sequence comprising SEQ ID NO: 54 in shNA format. In another embodiment of the nucleic acid molecules of the present invention, the nucleic acid molecule comprises a nucleotide sequence comprising SEQ ID NO: 55 in shNA format. In another embodiment of the nucleic acid molecules of the present invention, the nucleic acid molecule comprises a nucleotide sequence comprising SEQ ID NO: 56 in shNA format. In another embodiment of the nucleic acid molecules of the present invention, the nucleic acid molecule comprises a nucleotide sequence comprising SEQ ID NO: 57 in shNA format. In another embodiment of the nucleic acid molecules of the present invention, the nucleic acid molecule comprises a nucleotide sequence comprising SEQ ID NO: 58 in shNA format. In another embodiment of the nucleic acid molecules of the present invention, the nucleic acid molecule comprises a nucleotide sequence comprising SEQ ID NO: 59 in shNA format. In another embodiment of the nucleic acid molecules of the present invention, the nucleic acid molecule comprises a nucleotide sequence comprising SEQ ID NO: 60 in shNA format. In another embodiment of the nucleic acid molecules of the present invention, the nucleic acid molecule comprises a nucleotide sequence comprising SEQ ID NO: 61 in shNA format. In another embodiment of the nucleic acid molecules of the present invention, the nucleic acid molecule comprises a nucleotide sequence comprising SEQ ID NO: 62 in shNA format. In another embodiment of the nucleic acid molecules of the present invention, the nucleic acid molecule comprises a nucleotide sequence comprising SEQ ID NO: 63 in shNA format. In another embodiment of the nucleic acid molecules of the present invention, the nucleic acid molecule comprises a nucleotide sequence comprising SEQ ID NO: 64 in shNA format. In another embodiment of the nucleic acid molecules of the present invention, the nucleic acid molecule comprises a nucleotide sequence comprising SEQ ID NO: 65 in shNA format. In another embodiment of the nucleic acid molecules of the present invention, the nucleic acid molecule comprises a nucleotide sequence comprising SEQ ID NO: 66 in shNA format. In another embodiment of the nucleic acid molecules of the present invention, the nucleic acid molecule comprises a nucleotide sequence comprising SEQ ID NO: 67 in shNA format. In another embodiment of the nucleic acid molecules of the present invention, the nucleic acid molecule comprises a nucleotide sequence comprising SEQ ID NO: 68 in shNA format. In another embodiment of the nucleic acid molecules of the present invention, the nucleic acid molecule comprises a nucleotide sequence comprising SEQ ID NO: 69 in shNA format. In another embodiment of the nucleic acid molecules of the present invention, the nucleic acid molecule comprises a nucleotide sequence comprising SEQ ID NO: 70 in shNA format. In another embodiment of the nucleic acid molecules of the present invention, the nucleic acid molecule comprises a nucleotide sequence comprising SEQ ID NO: 71 in shNA format. In another embodiment of the nucleic acid molecules of the present invention, the nucleic acid molecule comprises a nucleotide sequence comprising SEQ ID NO: 72 in shNA format. In another embodiment of the nucleic acid molecules of the present invention, the nucleic acid molecule comprises a nucleotide sequence comprising SEQ ID NO: 73 in shNA format. In another embodiment of the nucleic acid molecules of the present invention, the nucleic acid molecule comprises a nucleotide sequence comprising SEQ ID NO: 74 in shNA format. In another embodiment of the nucleic acid molecules of the present invention, the nucleic acid molecule comprises a nucleotide sequence comprising SEQ ID NO: 75 in shNA format. In another embodiment of the nucleic acid molecules of the present invention, the nucleic acid molecule comprises a nucleotide sequence comprising SEQ ID NO: 76 in shNA format. In another embodiment of the nucleic acid molecules of the present invention, the nucleic acid molecule comprises a nucleotide sequence comprising SEQ ID NO: 77 in shNA format. In another embodiment of the nucleic acid molecules of the present invention, the nucleic acid molecule comprises a nucleotide sequence comprising SEQ ID NO: 78 in shNA format. In another embodiment of the nucleic acid molecules of the present invention, the nucleic acid molecule comprises a nucleotide sequence comprising SEQ ID NO: 79 in shNA format. In another embodiment of the nucleic acid molecules of the present invention, the nucleic acid molecule comprises a nucleotide sequence comprising SEQ ID NO: 80 in shNA format. In another embodiment of the nucleic acid molecules of the present invention, the nucleic acid molecule comprises a nucleotide sequence comprising SEQ ID NO: 81 in shNA format. In another embodiment of the nucleic acid molecules of the present invention, the nucleic acid molecule comprises a nucleotide sequence comprising SEQ ID NO: 82 in shNA format. In another embodiment of the nucleic acid molecules of the present invention, the nucleic acid molecule comprises a nucleotide sequence comprising SEQ ID NO: 83 in shNA format. In another embodiment of the nucleic acid molecules of the present invention, the nucleic acid molecule comprises a nucleotide sequence comprising SEQ ID NO: 84 in shNA format. In another embodiment of the nucleic acid molecules of the present invention, the nucleic acid molecule comprises a nucleotide sequence comprising SEQ ID NO: 85 in shNA format. In another embodiment of the nucleic acid molecules of the present invention, the nucleic acid molecule comprises a nucleotide sequence comprising SEQ ID NO: 86 in shNA format. In another embodiment of the nucleic acid molecules of the present invention, the nucleic acid molecule comprises a nucleotide sequence comprising SEQ ID NO: 87 in shNA format. In another embodiment of the nucleic acid molecules of the present invention, the nucleic acid molecule comprises a nucleotide sequence comprising SEQ ID NO: 88 in shNA format. In another embodiment of the nucleic acid molecules of the present invention, the nucleic acid molecule comprises a nucleotide sequence comprising SEQ ID NO: 89 in shNA format. In another embodiment of the nucleic acid molecules of the present invention, the nucleic acid molecule comprises a nucleotide sequence comprising SEQ ID NO: 90 in shNA format. In another embodiment of the nucleic acid molecules of the present invention, the nucleic acid molecule comprises a nucleotide sequence comprising SEQ ID NO: 91 in shNA format. In another embodiment of the nucleic acid molecules of the present invention, the nucleic acid molecule comprises a nucleotide sequence comprising SEQ ID NO: 92 in shNA format. In another embodiment of the nucleic acid molecules of the present invention, the nucleic acid molecule comprises a nucleotide sequence comprising SEQ ID NO: 93 in shNA format. In another embodiment of the nucleic acid molecules of the present invention, the nucleic acid molecule comprises a nucleotide sequence comprising SEQ ID NO: 94 in shNA format. In another embodiment of the nucleic acid molecules of the present invention, the nucleic acid molecule comprises a nucleotide sequence comprising SEQ ID NO: 95 in shNA format. In another embodiment of the nucleic acid molecules of the present invention, the nucleic acid molecule comprises a nucleotide sequence comprising SEQ ID NO: 96 in shNA format. In another embodiment of the nucleic acid molecules of the present invention, the nucleic acid molecule comprises a nucleotide sequence comprising SEQ ID NO: 97 in shNA format. In another embodiment of the nucleic acid molecules of the present invention, the nucleic acid molecule comprises a nucleotide sequence comprising SEQ ID NO: 98 in shNA format. In another embodiment of the nucleic acid molecules of the present invention, the nucleic acid molecule comprises a nucleotide sequence comprising SEQ ID NO: 99 in shNA format. In another embodiment of the nucleic acid molecules of the present invention, the nucleic acid molecule comprises a nucleotide sequence comprising SEQ ID NO: 100 in shNA format. In another embodiment of the nucleic acid molecules of the present invention, the nucleic acid molecule comprises a nucleotide sequence comprising SEQ ID NO: 101 in shNA format. In another embodiment of the nucleic acid molecules of the present invention, the nucleic acid molecule comprises a nucleotide sequence comprising SEQ ID NO: 102 in shNA format. In another embodiment of the nucleic acid molecules of the present invention, the nucleic acid molecule comprises a nucleotide sequence comprising SEQ ID NO: 103 in shNA format. In another embodiment of the nucleic acid molecules of the present invention, the nucleic acid molecule comprises a nucleotide sequence comprising SEQ ID NO: 104 in shNA format. In another embodiment of the nucleic acid molecules of the present invention, the nucleic acid molecule comprises a nucleotide sequence comprising SEQ ID NO: 105 in shNA format. In another embodiment of the nucleic acid molecules of the present invention, the nucleic acid molecule comprises a nucleotide sequence comprising SEQ ID NO: 106 in shNA format. In another embodiment of the nucleic acid molecules of the present invention, the nucleic acid molecule comprises a nucleotide sequence comprising SEQ ID NO: 107 in shNA format. In another embodiment of the nucleic acid molecules of the present invention, the nucleic acid molecule comprises a nucleotide sequence comprising SEQ ID NO: 108 in shNA format. In another embodiment of the nucleic acid molecules of the present invention, the nucleic acid molecule comprises a nucleotide sequence comprising SEQ ID NO: 109 in shNA format. In another embodiment of the nucleic acid molecules of the present invention, the nucleic acid molecule comprises a nucleotide sequence comprising SEQ ID NO: 110 in shNA format. In another embodiment of the nucleic acid molecules of the present invention, the nucleic acid molecule comprises a nucleotide sequence comprising SEQ ID NO: 114 in shNA format. In another embodiment of the nucleic acid molecules of the present invention, the nucleic acid molecule comprises a nucleotide sequence comprising SEQ ID NO: 115 in shNA format. In another embodiment of the nucleic acid molecules of the present invention, the nucleic acid molecule comprises a nucleotide sequence comprising SEQ ID NO: 116 in shNA format. In another embodiment of the nucleic acid molecules of the present invention, the nucleic acid molecule comprises a nucleotide sequence comprising SEQ ID NO: 117 in shNA format. In another embodiment of the nucleic acid molecules of the present invention, the nucleic acid molecule comprises a nucleotide sequence comprising SEQ ID NO: 118 in shNA format. In another embodiment of the nucleic acid molecules of the present invention, the nucleic acid molecule comprises a nucleotide sequence comprising SEQ ID NO: 119 in shNA format. In another embodiment of the nucleic acid molecules of the present invention, the nucleic acid molecule comprises a nucleotide sequence comprising SEQ ID NO: 120 in shNA format. In another embodiment of the nucleic acid molecules of the present invention, the nucleic acid molecule comprises a nucleotide sequence comprising SEQ ID NO: 121 in shNA format. In another embodiment of the nucleic acid molecules of the present invention, the nucleic acid molecule comprises a nucleotide sequence comprising SEQ ID NO: 122 in shNA format. In another embodiment of the nucleic acid molecules of the present invention, the nucleic acid molecule comprises a nucleotide sequence comprising SEQ ID NO: 123 in shNA format. In another embodiment of the nucleic acid molecules of the present invention, the nucleic acid molecule comprises a nucleotide sequence comprising SEQ ID NO: 124 in shNA format. In another embodiment of the nucleic acid molecules of the present invention, the nucleic acid molecule comprises a nucleotide sequence comprising SEQ ID NO: 125 in shNA format. In another embodiment of the nucleic acid molecules of the present invention, the nucleic acid molecule comprises a nucleotide sequence comprising SEQ ID NO: 126 in shNA format. In another embodiment of the nucleic acid molecules of the present invention, the nucleic acid molecule comprises a nucleotide sequence comprising SEQ ID NO: 127 in shNA format. In another embodiment of the nucleic acid molecules of the present invention, the nucleic acid molecule comprises a nucleotide sequence comprising SEQ ID NO: 128 in shNA format. In another embodiment of the nucleic acid molecules of the present invention, the nucleic acid molecule comprises a nucleotide sequence comprising SEQ ID NO: 129 in shNA format. In another embodiment of the nucleic acid molecules of the present invention, the nucleic acid molecule comprises a nucleotide sequence comprising SEQ ID NO: 130 in shNA format. In another embodiment of the nucleic acid molecules of the present invention, the nucleic acid molecule comprises a nucleotide sequence comprising SEQ ID NO: 131 in shNA format. In another embodiment of the nucleic acid molecules of the present invention, the nucleic acid molecule comprises a nucleotide sequence comprising SEQ ID NO: 132 in shNA format. In another embodiment of the nucleic acid molecules of the present invention, the nucleic acid molecule comprises a nucleotide sequence comprising SEQ ID NO: 133 in shNA format. In another embodiment of the nucleic acid molecules of the present invention, the nucleic acid molecule comprises a nucleotide sequence comprising SEQ ID NO: 134 in shNA format. In another embodiment of the nucleic acid molecules of the present invention, the nucleic acid molecule comprises a nucleotide sequence comprising SEQ ID NO: 135 in shNA format. In another embodiment of the nucleic acid molecules of the present invention, the nucleic acid molecule comprises nucleotide sequences selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof in shNA format. One embodiment of the present invention includes an expression cassette comprising a nucleotide sequence. In one embodiment of the expression cassette the nucleotide sequence is a human sequence. In another embodiment of the expression cassette of the present invention, the nucleotide sequence comprises SEQ ID NO: 1. In another embodiment of the expression cassette of the present invention, the nucleotide sequence comprises SEQ ID NO: 2. In another embodiment of the expression cassette of the present invention, the nucleotide sequence comprises SEQ ID NO: 3. In another embodiment of the expression cassette of the present invention, the nucleotide sequence comprises SEQ ID NO: 4. In another embodiment of the expression cassette of the present invention, the nucleotide sequence comprises SEQ ID NO: 5. In another embodiment of the expression cassette of the present invention, the nucleotide sequence comprises SEQ ID NO: 6. In another embodiment of the expression cassette of the present invention, the nucleotide sequence comprises SEQ ID NO: 7. In another embodiment of the expression cassette of the present invention, the nucleotide sequence comprises SEQ ID NO: 8. In another embodiment of the expression cassette of the present invention, the nucleotide sequence comprises SEQ ID NO: 9. In another embodiment of the expression cassette of the present invention, the nucleotide sequence comprises SEQ ID NO: 10. In another embodiment of the expression cassette of the present invention, the nucleotide sequence comprises SEQ ID NO: 11. In another embodiment of the expression cassette of the present invention, the nucleotide sequence comprises SEQ ID NO: 12. In another embodiment of the expression cassette of the present invention, the nucleotide sequence comprises SEQ ID NO: 13. In another embodiment of the expression cassette of the present invention, the nucleotide sequence comprises SEQ ID NO: 14. In another embodiment of the expression cassette of the present invention, the nucleotide sequence comprises SEQ ID NO: 15. In another embodiment of the expression cassette of the present invention, the nucleotide sequence comprises SEQ ID NO: 16. In another embodiment of the expression cassette of the present invention, the nucleotide sequence comprises SEQ ID NO: 17. In another embodiment of the expression cassette of the present invention, the nucleotide sequence comprises SEQ ID NO: 18. In another embodiment of the expression cassette of the present invention, the nucleotide sequence comprises SEQ ID NO: 19. In another embodiment of the expression cassette of the present invention, the nucleotide sequence comprises SEQ ID NO: 20. In another embodiment of the expression cassette of the present invention, the nucleotide sequence comprises SEQ ID NO: 21. In another embodiment of the expression cassette of the present invention, the nucleotide sequence comprises SEQ ID NO: 22. In another embodiment of the expression cassette of the present invention, the nucleotide sequence comprises SEQ ID NO: 23. In another embodiment of the expression cassette of the present invention, the nucleotide sequence comprises SEQ ID NO: 24. In another embodiment of the expression cassette of the present invention, the nucleotide sequence comprises SEQ ID NO: 25. In another embodiment of the expression cassette of the present invention, the nucleotide sequence comprises SEQ ID NO: 26. In another embodiment of the expression cassette of the present invention, the nucleotide sequence comprises SEQ ID NO: 27. In another embodiment of the expression cassette of the present invention, the nucleotide sequence comprises SEQ ID NO: 28. In another embodiment of the expression cassette of the present invention, the nucleotide sequence comprises SEQ ID NO: 29. In another embodiment of the expression cassette of the present invention, the nucleotide sequence comprises SEQ ID NO: 30. In another embodiment of the expression cassette of the present invention, the nucleotide sequence comprises SEQ ID NO: 31. In another embodiment of the expression cassette of the present invention, the nucleotide sequence comprises SEQ ID NO: 32. In another embodiment of the expression cassette of the present invention, the nucleotide sequence comprises SEQ ID NO: 33. In another embodiment of the expression cassette of the present invention, the nucleotide sequence comprises SEQ ID NO: 34. In another embodiment of the expression cassette of the present invention, the nucleotide sequence comprises SEQ ID NO: 35. In another embodiment of the expression cassette of the present invention, the nucleotide sequence comprises SEQ ID NO: 36. In another embodiment of the expression cassette of the present invention, the nucleotide sequence comprises SEQ ID NO: 37. In another embodiment of the expression cassette of the present invention, the nucleotide sequence comprises SEQ ID NO: 38. In another embodiment of the expression cassette of the present invention, the nucleotide sequence comprises SEQ ID NO: 39. In another embodiment of the expression cassette of the present invention, the nucleotide sequence comprises SEQ ID NO: 40. In another embodiment of the expression cassette of the present invention, the nucleotide sequence comprises SEQ ID NO: 41. In another embodiment of the expression cassette of the present invention, the nucleotide sequence comprises SEQ ID NO: 42. In another embodiment of the expression cassette of the present invention, the nucleotide sequence comprises SEQ ID NO: 43. In another embodiment of the expression cassette of the present invention, the nucleotide sequence comprises SEQ ID NO: 44. In another embodiment of the expression cassette of the present invention, the nucleotide sequence comprises SEQ ID NO: 45. In another embodiment of the expression cassette of the present invention, the nucleotide sequence comprises SEQ ID NO: 46. In another embodiment of the expression cassette of the present invention, the nucleotide sequence comprises SEQ ID NO: 47. In another embodiment of the expression cassette of the present invention, the nucleotide sequence comprises SEQ ID NO: 48. In another embodiment of the expression cassette of the present invention, the nucleotide sequence comprises SEQ ID NO: 49. In another embodiment of the expression cassette of the present invention, the nucleotide sequence comprises SEQ ID NO: 50. In another embodiment of the expression cassette of the present invention, the nucleotide sequence comprises SEQ ID NO: 51. In another embodiment of the expression cassette of the present invention, the nucleotide sequence comprises SEQ ID NO: 52. In another embodiment of the expression cassette of the present invention, the nucleotide sequence comprises SEQ ID NO: 53. In another embodiment of the expression cassette of the present invention, the nucleotide sequence comprises SEQ ID NO: 54. In another embodiment of the expression cassette of the present invention, the nucleotide sequence comprises SEQ ID NO: 55. In another embodiment of the expression cassette of the present invention, the nucleotide sequence comprises SEQ ID NO: 56. In another embodiment of the expression cassette of the present invention, the nucleotide sequence comprises SEQ ID NO: 57. In another embodiment of the expression cassette of the present invention, the nucleotide sequence comprises SEQ ID NO: 58. In another embodiment of the expression cassette of the present invention, the nucleotide sequence comprises SEQ ID NO: 59. In another embodiment of the expression cassette of the present invention, the nucleotide sequence comprises SEQ ID NO: 60. In another embodiment of the expression cassette of the present invention, the nucleotide sequence comprises SEQ ID NO: 61. In another embodiment of the expression cassette of the present invention, the nucleotide sequence comprises SEQ ID NO:

62. In another embodiment of the expression cassette of the present invention, the nucleotide sequence comprises SEQ ID NO: 63. In another embodiment of the expression cassette of the present invention, the nucleotide sequence comprises SEQ ID NO: 64. In another embodiment of the expression cassette of the present invention, the nucleotide sequence comprises SEQ ID NO: 65. In another embodiment of the expression cassette of the present invention, the nucleotide sequence comprises SEQ ID NO: 66. In another embodiment of the expression cassette of the present invention, the nucleotide sequence comprises SEQ ID NO: 67. In another embodiment of the expression cassette of the present invention, the nucleotide sequence comprises SEQ ID NO: 68. In another embodiment of the expression cassette of the present invention, the nucleotide sequence comprises SEQ ID NO: 69. In another embodiment of the expression cassette of the present invention, the nucleotide sequence comprises SEQ ID NO: 70. In another embodiment of the expression cassette of the present invention, the nucleotide sequence comprises SEQ ID NO: 71. In another embodiment of the expression cassette of the present invention, the nucleotide sequence comprises SEQ ID NO: 72. In another embodiment of the expression cassette of the present invention, the nucleotide sequence comprises SEQ ID NO: 73. In another embodiment of the expression cassette of the present invention, the nucleotide sequence comprises SEQ ID NO: 74. In another embodiment of the expression cassette of the present invention, the nucleotide sequence comprises SEQ ID NO: 75. In another embodiment of the expression cassette of the present invention, the nucleotide sequence comprises SEQ ID NO: 76. In another embodiment of the expression cassette of the present invention, the nucleotide sequence comprises SEQ ID NO: 77. In another embodiment of the expression cassette of the present invention, the nucleotide sequence comprises SEQ ID NO: 78. In another embodiment of the expression cassette of the present invention, the nucleotide sequence comprises SEQ ID NO: 79. In another embodiment of the expression cassette of the present invention, the nucleotide sequence comprises SEQ ID NO: 80. In another embodiment of the expression cassette of the present invention, the nucleotide sequence comprises SEQ ID NO: 81. In another embodiment of the expression cassette of the present invention, the nucleotide sequence comprises SEQ ID NO: 82. In another embodiment of the expression cassette of the present invention, the nucleotide sequence comprises SEQ ID NO: 83. In another embodiment of the expression cassette of the present invention, the nucleotide sequence comprises SEQ ID NO: 84. In another embodiment of the expression cassette of the present invention, the nucleotide sequence comprises SEQ ID NO: 85. In another embodiment of the expression cassette of the present invention, the nucleotide sequence comprises SEQ ID NO: 86. In another embodiment of the expression cassette of the present invention, the nucleotide sequence comprises SEQ ID NO: 87. In another embodiment of the expression cassette of the present invention, the nucleotide sequence comprises SEQ ID NO: 88. In another embodiment of the expression cassette of the present invention, the nucleotide sequence comprises SEQ ID NO: 89. In another embodiment of the expression cassette of the present invention, the nucleotide sequence comprises SEQ ID NO: 90. In another embodiment of the expression cassette of the present invention, the nucleotide sequence comprises SEQ ID NO: 91. In another embodiment of the expression cassette of the present invention, the nucleotide sequence comprises SEQ ID NO: 92. In another embodiment of the expression cassette of the present invention, the nucleotide sequence comprises SEQ ID NO: 93. In another embodiment of the expression cassette of the present invention, the nucleotide sequence comprises SEQ ID NO: 94. In another embodiment of the expression cassette of the present invention, the nucleotide sequence comprises SEQ ID NO: 95. In another embodiment of the expression cassette of the present invention, the nucleotide sequence comprises SEQ ID NO: 96. In another embodiment of the expression cassette of the present invention, the nucleotide sequence comprises SEQ ID NO: 97. In another embodiment of the expression cassette of the present invention, the nucleotide sequence comprises SEQ ID NO: 98. In another embodiment of the expression cassette of the present invention, the nucleotide sequence comprises SEQ ID NO: 99. In another embodiment of the expression cassette of the present invention, the nucleotide sequence comprises SEQ ID NO: 100. In another embodiment of the expression cassette of the present invention, the nucleotide sequence comprises SEQ ID NO: 101. In another embodiment of the expression cassette of the present invention, the nucleotide sequence comprises SEQ ID NO: 102. In another embodiment of the expression cassette of the present invention, the nucleotide sequence comprises SEQ ID NO: 103. In another embodiment of the expression cassette of the present invention, the nucleotide sequence comprises SEQ ID NO: 104. In another embodiment of the expression cassette of the present invention, the nucleotide sequence comprises SEQ ID NO: 105. In another embodiment of the expression cassette of the present invention, the nucleotide sequence comprises SEQ ID NO: 106. In another embodiment of the expression cassette of the present invention, the nucleotide sequence comprises SEQ ID NO: 107. In another embodiment of the expression cassette of the present invention, the nucleotide sequence comprises SEQ ID NO: 108. In another embodiment of the expression cassette of the present invention, the nucleotide sequence comprises SEQ ID NO: 109. In another embodiment of the expression cassette of the present invention, the nucleotide sequence comprises SEQ ID NO: 110. In another embodiment of the expression cassette of the present invention, the nucleotide sequence comprises SEQ ID NO: 114. In another embodiment of the expression cassette of the present invention, the nucleotide sequence comprises SEQ ID NO: 115. In another embodiment of the expression cassette of the present invention, the nucleotide sequence comprises SEQ ID NO: 116. In another embodiment of the expression cassette of the present invention, the nucleotide sequence comprises SEQ ID NO: 117. In another embodiment of the expression cassette of the present invention, the nucleotide sequence comprises SEQ ID NO: 118. In another embodiment of the expression cassette of the present invention, the nucleotide sequence comprises SEQ ID NO: 119. In another embodiment of the expression cassette of the present invention, the nucleotide sequence comprises SEQ ID NO: 120. In another embodiment of the expression cassette of the present invention, the nucleotide sequence comprises SEQ ID NO: 121. In another embodiment of the expression cassette of the present invention, the nucleotide sequence comprises SEQ ID NO: 122. In another embodiment of the expression cassette of the present invention, the nucleotide sequence comprises SEQ ID NO: 123. In another embodiment of the expression cassette of the present invention, the nucleotide sequence comprises SEQ ID NO: 124. In another embodiment of the expression cassette of the present invention, the nucleotide sequence comprises SEQ ID NO: 125. In another embodiment of the expression cassette of the present invention, the nucleotide sequence comprises SEQ ID NO: 126. In another embodiment of the expression cassette of the present invention, the nucleotide sequence comprises SEQ ID NO: 127. In another embodiment of the expression cassette of the present invention, the nucleotide sequence comprises SEQ ID NO: 128. In another embodiment of the expression cassette of the present invention, the nucleotide sequence comprises SEQ ID NO: 129. In another embodiment of the expression cassette of the present invention, the nucleotide sequence comprises SEQ ID NO: 130. In another embodiment of the expression cassette of the present invention, the nucleotide sequence comprises SEQ ID NO: 131. In another embodiment of the expression cassette of the present invention, the nucleotide sequence comprises SEQ ID NO: 132. In another embodiment of the expression cassette of the present invention, the nucleotide sequence comprises SEQ ID NO: 133. In another embodiment of the expression cassette of the present invention, the nucleotide sequence comprises SEQ ID NO: 134. In another embodiment of the expression cassette of the present invention, the nucleotide sequence comprises SEQ ID NO: 135. In another embodiment of the expression cassette of the present invention, the nucleotide sequence is selected from SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and any combination thereof. In another embodiment of the expression cassette of the present invention, the expression cassette further comprises a regulatable or a constitutive promoter operably linked to the nucleic acid sequence.

One embodiment of the present invention includes a cell comprising an expression cassette of the present invention. Another embodiment of the present invention includes a vector comprising an expression cassette of the present invention. In one embodiment of the vector of the present invention the vector is a viral vector. In another embodiment of the vector of the present invention the vector is an adenoviral virus vector. In another embodiment of the vector of the present invention the vector is a retroviral virus vector (e.g. lentivirus, Rous sarcoma virus, Harvey sarcoma virus, Moloney murine leukemia virus, feline immunodeficiency virus). In another embodiment of the vector of the present invention the vector is a parvoviral virus vector (e.g adeno-associated virus (AAV)). In another embodiment of the vector of the present invention the vector is a picornaviral virus vector (e.g. poliovirus). In another embodiment of the vector of the present invention the vector is a herpes virus vector (e.g. herpes simplex virus). In another embodiment of the vector of the present invention the vector comprises a regulatable or a constitutive promoter operably linked to a nucleic acid sequence of the present invention.

One embodiment of the present invention includes a kit for screening individuals for the heterozygous presence of one or more single nucleotide polymorphisms within the individual's Huntington's genes. In one embodiment of the kit of the present invention, the kit comprises a molecular beacon that detects a single nucleotide polymorphism found in SEQ ID NO: 1 wherein said molecular beacon comprises at least a portion of the reverse complement of SEQ ID NO: 1. In another embodiment of the kits of the present invention, the kit comprises a molecular beacon that detects a single nucleotide polymorphism found in SEQ ID NO: 2 wherein said molecular beacon comprises at least a portion of the reverse complement of SEQ ID NO: 2. In another embodiment of the kits of the present invention, the kit comprises a molecular beacon that detects a single nucleotide polymorphism found in SEQ ID NO: 3 wherein said molecular beacon comprises at least a portion of the reverse complement of SEQ ID NO: 3. In another embodiment of the kits of the present invention, the kit comprises a molecular beacon that detects a single nucleotide polymorphism found in SEQ ID NO: 4 wherein said molecular beacon comprises at least a portion of the reverse complement of SEQ ID NO: 4. In another embodiment of the kits of the present invention, the kit comprises a molecular beacon that detects a single nucleotide polymorphism found in SEQ ID NO: 5 wherein said molecular beacon comprises at least a portion of the reverse complement of SEQ ID NO: 5. In another embodiment of the kits of the present invention, the kit comprises a molecular beacon that detects a single nucleotide polymorphism found in SEQ ID NO: 6 wherein said molecular beacon comprises at least a portion of the reverse complement of SEQ ID NO: 6. In another embodiment of the kits of the present invention, the kit comprises a molecular beacon that detects a single nucleotide polymorphism found in SEQ ID NO: 7 wherein said molecular beacon comprises at least a portion of the reverse complement of SEQ ID NO: 7. In another embodiment of the kits of the present invention, the kit comprises a molecular beacon that detects a single nucleotide polymorphism found in SEQ ID NO: 8 wherein said molecular beacon comprises at least a portion of the reverse complement of SEQ ID NO: 8. In another embodiment of the kits of the present invention, the kit comprises a molecular beacon that detects a single nucleotide polymorphism found in SEQ ID NO: 9 wherein said molecular beacon comprises at least a portion of the reverse complement of SEQ ID NO: 9. In another embodiment of the kits of the present invention, the kit comprises a molecular beacon that detects a single nucleotide polymorphism found in SEQ ID NO: 10 wherein said molecular beacon comprises at least a portion of the reverse complement of SEQ ID NO: 10. In another embodiment of the kits of the present invention, the kit comprises a molecular beacon that detects a single nucleotide polymorphism found in SEQ ID NO: 11 wherein said molecular beacon comprises at least a portion of the reverse complement of SEQ ID NO: 11. In another embodiment of the kits of the present invention, the kit comprises a molecular beacon that detects a single nucleotide polymorphism found in SEQ ID NO: 12 wherein said molecular beacon comprises at least a portion of the reverse complement of SEQ ID NO: 12. In another embodiment of the kits of the present invention, the kit comprises a molecular beacon that detects a single nucleotide polymorphism found in SEQ ID NO: 13 wherein said molecular beacon comprises at least a portion of the reverse complement of SEQ ID NO: 13. In another embodiment of the kits of the present invention, the kit comprises a molecular beacon that detects a single nucleotide polymorphism found in SEQ ID NO: 14 wherein said molecular beacon comprises at least a portion of the reverse complement of SEQ ID NO: 14. In another embodiment of the kits of the present invention, the kit comprises a molecular beacon that detects a single nucleotide polymorphism found in SEQ ID NO: 15 wherein said molecular beacon comprises at least a portion of the reverse complement of SEQ ID NO: 15. In another embodiment of the kits of the present invention, the kit comprises a molecular beacon that detects a single nucleotide polymorphism found in SEQ ID NO: 16 wherein said molecular beacon comprises at least a portion of the reverse complement of SEQ ID NO: 16. In another embodiment of the kits of the present invention, the kit comprises a molecular beacon that detects a single nucleotide polymorphism found in SEQ ID NO: 17 wherein said molecular beacon comprises at least a portion of the reverse complement of SEQ ID NO: 17. In another embodiment of the kits of the present invention, the kit comprises a molecular beacon that detects a single nucleotide polymorphism found in SEQ ID NO: 18 wherein said molecular beacon comprises at least a portion of the reverse complement of SEQ ID NO: 18. In another embodiment of the kits of the present invention, the kit comprises a molecular beacon that detects a single nucleotide polymorphism found in SEQ ID NO: 19 wherein said molecular beacon comprises at least a portion of the reverse complement of SEQ ID NO: 19. In another embodiment of the kits of the present invention, the kit comprises a molecular beacon that detects a single nucleotide polymorphism found in SEQ ID NO: 20 wherein said molecular beacon comprises at least a portion of the reverse complement of SEQ ID NO: 20. In another embodiment of the kits of the present invention, the kit comprises a molecular beacon that detects a single nucleotide polymorphism found in SEQ ID NO: 21 wherein said molecular beacon comprises at least a portion of the reverse complement of SEQ ID NO: 21. In another embodiment of the kits of the present invention, the kit comprises a molecular beacon that detects a single nucleotide polymorphism found in SEQ ID NO: 22 wherein said molecular beacon comprises at least a portion of the reverse complement of SEQ ID NO: 22. In another embodiment according to the kits of the present invention, the kit comprises at least one molecular beacon that detects a single nucleotide polymorphism found in a sequence selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; and SEQ ID NO: 22 wherein the molecular beacon comprises at least a portion of the reverse complement of the sequence containing the detected single nucleotide polymorphism.

In one embodiment of the kit of the present invention, the kit comprises nucleic acid molecules that preferentially suppress the expression of amino acid sequences encoding for mutated huntingtin ("htt") over suppressing the expression of amino acid sequences encoding for normal htt by targeting an area of a Huntington's disease gene that is heterozygous for the presence of one or more single nucleotide polymorphisms. In another embodiment of the kit of the present invention, the kit includes nucleic acid molecules comprising nucleotide sequences comprising SEQ ID NO: 1. In another embodiment of the kit of the present invention, the kit includes nucleic acid molecules comprising nucleotide sequences comprising SEQ ID NO: 2. In another embodiment of the kit of the present invention, the kit includes nucleic acid molecules comprising nucleotide sequences comprising SEQ ID NO: 3. In another embodiment of the kit of the present invention, the kit includes nucleic acid molecules comprising nucleotide sequences comprising SEQ ID NO: 4. In another embodiment of the kit of the present invention, the kit includes nucleic acid molecules comprising nucleotide sequences comprising SEQ ID NO: 5. In another embodiment of the kit of the present invention, the kit includes nucleic acid molecules comprising nucleotide sequences comprising SEQ ID NO: 6. In another embodiment of the kit of the present invention, the kit includes nucleic acid molecules comprising nucleotide sequences comprising SEQ ID NO: 7. In another embodiment of the kit of the present invention, the kit includes nucleic acid molecules comprising nucleotide sequences comprising SEQ ID NO: 8. In another embodiment of the kit of the present invention, the kit includes nucleic acid molecules comprising nucleotide sequences comprising SEQ ID NO: 9. In another embodiment of the kit of the present invention, the kit includes nucleic acid molecules comprising nucleotide sequences comprising SEQ ID NO: 10. In another embodiment of the kit of the present invention, the kit includes nucleic acid molecules comprising nucleotide sequences comprising SEQ ID NO: 11. In another embodiment of the kit of the present invention, the kit includes nucleic acid molecules comprising nucleotide sequences comprising SEQ ID NO: 12. In another embodiment of the kit of the present invention, the kit includes nucleic acid molecules comprising nucleotide sequences comprising SEQ ID NO: 13. In another embodiment of the kit of the present invention, the kit includes nucleic acid molecules comprising nucleotide sequences comprising SEQ ID NO: 14. In another embodiment of the kit of the present invention, the kit includes nucleic acid molecules comprising nucleotide sequences comprising SEQ ID NO: 15. In another embodiment of the kit of the present invention, the kit includes nucleic acid molecules comprising nucleotide sequences comprising SEQ ID NO: 16. In another embodiment of the kit of the present invention, the kit includes nucleic acid molecules comprising nucleotide sequences comprising SEQ ID NO: 17. In another embodiment of the kit of the present invention, the kit includes nucleic acid molecules comprising nucleotide sequences comprising SEQ ID NO: 18. In another embodiment of the kit of the present invention, the kit includes nucleic acid molecules comprising nucleotide sequences comprising SEQ ID NO: 19. In another embodiment of the kit of the present invention, the kit includes nucleic acid molecules comprising nucleotide sequences comprising SEQ ID NO: 20. In another embodiment of the kit of the present invention, the kit includes nucleic acid molecules comprising nucleotide sequences comprising SEQ ID NO: 21. In another embodiment of the kit of the present invention, the kit includes nucleic acid molecules comprising nucleotide sequences comprising SEQ ID NO: 22. In another embodiment of the kit of the present invention, the kit includes nucleic acid molecules comprising nucleotide sequences comprising SEQ ID NO: 23. In another embodiment of the kit of the present invention, the kit includes nucleic acid molecules comprising nucleotide sequences comprising SEQ ID NO: 24. In another embodiment of the kit of the present invention, the kit includes nucleic acid molecules comprising nucleotide sequences comprising SEQ ID NO: 25. In another embodiment of the kit of the present invention, the kit includes nucleic acid molecules comprising nucleotide sequences comprising SEQ ID NO: 26. In another embodiment of the kit of the present invention, the kit includes nucleic acid molecules comprising nucleotide sequences comprising SEQ ID NO: 27. In another embodiment of the kit of the present invention, the kit includes nucleic acid molecules comprising nucleotide sequences comprising SEQ ID NO: 28. In another embodiment of the kit of the present invention, the kit includes nucleic acid molecules comprising nucleotide sequences comprising SEQ ID NO: 29. In another embodiment of the kit of the present invention, the kit includes nucleic acid molecules comprising nucleotide sequences comprising SEQ ID NO: 30. In another embodiment of the kit of the present invention, the kit includes nucleic acid molecules comprising nucleotide sequences comprising SEQ ID NO: 31. In another embodiment of the kit of the present invention, the kit includes nucleic acid molecules comprising nucleotide sequences comprising SEQ ID NO: 32. In another embodiment of the kit of the present invention, the kit includes nucleic acid molecules comprising nucleotide sequences comprising SEQ ID NO: 33. In another embodiment of the kit of the present invention, the kit includes nucleic acid molecules comprising nucleotide sequences comprising SEQ ID NO: 34. In another embodiment of the kit of the present invention, the kit includes nucleic acid molecules comprising nucleotide sequences comprising SEQ ID NO: 35. In another embodiment of the kit of the present invention, the kit includes nucleic acid molecules comprising nucleotide sequences comprising SEQ ID NO: 36. In another embodiment of the kit of the present invention, the kit includes nucleic acid molecules comprising nucleotide sequences comprising SEQ ID NO: 37. In another embodiment of the kit of the present invention, the kit includes nucleic acid molecules comprising nucleotide sequences comprising SEQ ID NO: 38. In another embodiment of the kit of the present invention, the kit includes nucleic acid molecules comprising nucleotide sequences comprising SEQ ID NO: 39. In another embodiment of the kit of the present invention, the kit includes nucleic acid molecules comprising nucleotide sequences comprising SEQ ID NO: 40. In another embodiment of the kit of the present invention, the kit includes nucleic acid molecules comprising nucleotide sequences comprising SEQ ID NO: 41. In another embodiment of the kit of the present invention, the kit includes nucleic acid molecules comprising nucleotide sequences comprising SEQ ID NO: 42. In another embodiment of the kit of the present invention, the kit includes nucleic acid molecules comprising nucleotide sequences comprising SEQ ID NO: 43. In another embodiment of the kit of the present invention, the kit includes nucleic acid molecules comprising nucleotide sequences comprising SEQ ID NO: 44. In another embodiment of the kit of the present invention, the kit includes nucleic acid molecules comprising nucleotide sequences comprising SEQ ID NO: 45. In another embodiment of the kit of the present invention, the kit includes nucleic acid molecules comprising nucleotide sequences comprising SEQ ID NO: 46. In another embodiment of the kit of the present invention, the kit includes nucleic acid molecules comprising nucleotide sequences comprising SEQ ID NO: 47. In another embodiment of the kit of the present invention, the kit includes nucleic acid molecules comprising nucleotide sequences comprising SEQ ID NO: 48. In another embodiment of the kit of the present invention, the kit includes nucleic acid molecules comprising nucleotide sequences comprising SEQ ID NO: 49. In another embodiment of the kit of the present invention, the kit includes nucleic acid molecules comprising nucleotide sequences comprising SEQ ID NO: 50. In another embodiment of the kit of the present invention, the kit includes nucleic acid molecules comprising nucleotide sequences comprising SEQ ID NO: 51. In another embodiment of the kit of the present invention, the kit includes nucleic acid molecules comprising nucleotide sequences comprising SEQ ID NO: 52. In another embodiment of the kit of the present invention, the kit includes nucleic acid molecules comprising nucleotide sequences comprising SEQ ID NO: 53. In another embodiment of the kit of the present invention, the kit includes nucleic acid molecules comprising nucleotide sequences comprising SEQ ID NO: 54. In another embodiment of the kit of the present invention, the kit includes nucleic acid molecules comprising nucleotide sequences comprising SEQ ID NO: 55. In another embodiment of the kit of the present invention, the kit includes nucleic acid molecules comprising nucleotide sequences comprising SEQ ID NO: 56. In another embodiment of the kit of the present invention, the kit includes nucleic acid molecules comprising nucleotide sequences comprising SEQ ID NO: 57. In another embodiment of the kit of the present invention, the kit includes nucleic acid molecules comprising nucleotide sequences comprising SEQ ID NO: 58. In another embodiment of the kit of the present invention, the kit includes nucleic acid molecules comprising nucleotide sequences comprising SEQ ID NO: 59. In another embodiment of the kit of the present invention, the kit includes nucleic acid molecules comprising nucleotide sequences comprising SEQ ID NO: 60. In another embodiment of the kit of the present invention, the kit includes nucleic acid molecules comprising nucleotide sequences comprising SEQ ID NO: 61. In another embodiment of the kit of the present invention, the kit includes nucleic acid molecules comprising nucleotide sequences comprising SEQ ID NO: 62. In another embodiment of the kit of the present invention, the kit includes nucleic acid molecules comprising nucleotide sequences comprising SEQ ID NO: 63. In another embodiment of the kit of the present invention, the kit includes nucleic acid molecules comprising nucleotide sequences comprising SEQ ID NO: 64. In another embodiment of the kit of the present invention, the kit includes nucleic acid molecules comprising nucleotide sequences comprising SEQ ID NO: 65. In another embodiment of the kit of the present invention, the kit includes nucleic acid molecules comprising nucleotide sequences comprising SEQ ID NO: 66. In another embodiment of the kit of the present invention, the kit includes nucleic acid molecules comprising nucleotide sequences comprising SEQ ID NO: 67. In another embodiment of the kit of the present invention, the kit includes nucleic acid molecules comprising nucleotide sequences comprising SEQ ID NO: 68. In another embodiment of the kit of the present invention, the kit includes nucleic acid molecules comprising nucleotide sequences comprising SEQ ID NO: 69. In another embodiment of the kit of the present invention, the kit includes nucleic acid molecules comprising nucleotide sequences comprising SEQ ID NO: 70. In another embodiment of the kit of the present invention, the kit includes nucleic acid molecules comprising nucleotide sequences comprising SEQ ID NO: 71. In another embodiment of the kit of the present invention, the kit includes nucleic acid molecules comprising nucleotide sequences comprising SEQ ID NO: 72. In another embodiment of the kit of the present invention, the kit includes nucleic acid molecules comprising nucleotide sequences comprising SEQ ID NO: 73. In another embodiment of the kit of the present invention, the kit includes nucleic acid molecules comprising nucleotide sequences comprising SEQ ID NO: 74. In another embodiment of the kit of the present invention, the kit includes nucleic acid molecules comprising nucleotide sequences comprising SEQ ID NO: 75. In another embodiment of the kit of the present invention, the kit includes nucleic acid molecules comprising nucleotide sequences comprising SEQ ID NO: 76. In another embodiment of the kit of the present invention, the kit includes nucleic acid molecules comprising nucleotide sequences comprising SEQ ID NO: 77. In another embodiment of the kit of the present invention, the kit includes nucleic acid molecules comprising nucleotide sequences comprising SEQ ID NO: 78. In another embodiment of the kit of the present invention, the kit includes nucleic acid molecules comprising nucleotide sequences comprising SEQ ID NO: 79. In another embodiment of the kit of the present invention, the kit includes nucleic acid molecules comprising nucleotide sequences comprising SEQ ID NO: 80. In another embodiment of the kit of the present invention, the kit includes nucleic acid molecules comprising nucleotide sequences comprising SEQ ID NO: 81. In another embodiment of the kit of the present invention, the kit includes nucleic acid molecules comprising nucleotide sequences comprising SEQ ID NO: 82. In another embodiment of the kit of the present invention, the kit includes nucleic acid molecules comprising nucleotide sequences comprising SEQ ID NO: 83. In another embodiment of the kit of the present invention, the kit includes nucleic acid molecules comprising nucleotide sequences comprising SEQ ID NO: 84. In another embodiment of the kit of the present invention, the kit includes nucleic acid molecules comprising nucleotide sequences comprising SEQ ID NO: 85. In another embodiment of the kit of the present invention, the kit includes nucleic acid molecules comprising nucleotide sequences comprising SEQ ID NO: 86. In another embodiment of the kit of the present invention, the kit includes nucleic acid molecules comprising nucleotide sequences comprising SEQ ID NO: 87. In another embodiment of the kit of the present invention, the kit includes nucleic acid molecules comprising nucleotide sequences comprising SEQ ID NO: 88. In another embodiment of the kit of the present invention, the kit includes nucleic acid molecules comprising nucleotide sequences comprising SEQ ID NO: 89. In another embodiment of the kit of the present invention, the kit includes nucleic acid molecules comprising nucleotide sequences comprising SEQ ID NO: 90. In another embodiment of the kit of the present invention, the kit includes nucleic acid molecules comprising nucleotide sequences comprising SEQ ID NO: 91. In another embodiment of the kit of the present invention, the kit includes nucleic acid molecules comprising nucleotide sequences comprising SEQ ID NO: 92. In another embodiment of the kit of the present invention, the kit includes nucleic acid molecules comprising nucleotide sequences comprising SEQ ID NO: 93. In another embodiment of the kit of the present invention, the kit includes nucleic acid molecules comprising nucleotide sequences comprising SEQ ID NO: 94. In another embodiment of the kit of the present invention, the kit includes nucleic acid molecules comprising nucleotide sequences comprising SEQ ID NO: 95. In another embodiment of the kit of the present invention, the kit includes nucleic acid molecules comprising nucleotide sequences comprising SEQ ID NO: 96. In another embodiment of the kit of the present invention, the kit includes nucleic acid molecules comprising nucleotide sequences comprising SEQ ID NO: 97. In another embodiment of the kit of the present invention, the kit includes nucleic acid molecules comprising nucleotide sequences comprising SEQ ID NO: 98. In another embodiment of the kit of the present invention, the kit includes nucleic acid molecules comprising nucleotide sequences comprising SEQ ID NO: 99. In another embodiment of the kit of the present invention, the kit includes nucleic acid molecules comprising nucleotide sequences comprising SEQ ID NO: 100. In another embodiment of the kit of the present invention, the kit includes nucleic acid molecules comprising nucleotide sequences comprising SEQ ID NO: 101. In another embodiment of the kit of the present invention, the kit includes nucleic acid molecules comprising nucleotide sequences comprising SEQ ID NO: 102. In another embodiment of the kit of the present invention, the kit includes nucleic acid molecules comprising nucleotide sequences comprising SEQ ID NO: 103. In another embodiment of the kit of the present invention, the kit includes nucleic acid molecules comprising nucleotide sequences comprising SEQ ID NO: 104. In another embodiment of the kit of the present invention, the kit includes nucleic acid molecules comprising nucleotide sequences comprising SEQ ID NO: 105. In another embodiment of the kit of the present invention, the kit includes nucleic acid molecules comprising nucleotide sequences comprising SEQ ID NO: 106. In another embodiment of the kit of the present invention, the kit includes nucleic acid molecules comprising nucleotide sequences comprising SEQ ID NO: 107. In another embodiment of the kit of the present invention, the kit includes nucleic acid molecules comprising nucleotide sequences comprising SEQ ID NO: 108. In another embodiment of the kit of the present invention, the kit includes nucleic acid molecules comprising nucleotide sequences comprising SEQ ID NO: 109. In another embodiment of the kit of the present invention, the kit includes nucleic acid molecules comprising nucleotide sequences comprising SEQ ID NO: 110. In another embodiment of the kit of the present invention, the kit includes nucleic acid molecules comprising nucleotide sequences comprising SEQ ID NO: 114. In another embodiment of the kit of the present invention, the kit includes nucleic acid molecules comprising nucleotide sequences comprising SEQ ID NO: 115. In another embodiment of the kit of the present invention, the kit includes nucleic acid molecules comprising nucleotide sequences comprising SEQ ID NO: 116. In another embodiment of the kit of the present invention, the kit includes nucleic acid molecules comprising nucleotide sequences comprising SEQ ID NO: 117. In another embodiment of the kit of the present invention, the kit includes nucleic acid molecules comprising nucleotide sequences comprising SEQ ID NO: 118. In another embodiment of the kit of the present invention, the kit includes nucleic acid molecules comprising nucleotide sequences comprising SEQ ID NO: 119. In another embodiment of the kit of the present invention, the kit includes nucleic acid molecules comprising nucleotide sequences comprising SEQ ID NO: 120. In another embodiment of the kit of the present invention, the kit includes nucleic acid molecules comprising nucleotide sequences comprising SEQ ID NO: 121. In another embodiment of the kit of the present invention, the kit includes nucleic acid molecules comprising nucleotide sequences comprising SEQ ID NO: 122. In another embodiment of the kit of the present invention, the kit includes nucleic acid molecules comprising nucleotide sequences comprising SEQ ID NO: 123. In another embodiment of the kit of the present invention, the kit includes nucleic acid molecules comprising nucleotide sequences comprising SEQ ID NO: 124. In another embodiment of the kit of the present invention, the kit includes nucleic acid molecules comprising nucleotide sequences comprising SEQ ID NO: 125. In another embodiment of the kit of the present invention, the kit includes nucleic acid molecules comprising nucleotide sequences comprising SEQ ID NO: 126. In another embodiment of the kit of the present invention, the kit includes nucleic acid molecules comprising nucleotide sequences comprising SEQ ID NO: 127. In another embodiment of the kit of the present invention, the kit includes nucleic acid molecules comprising nucleotide sequences comprising SEQ ID NO: 128. In another embodiment of the kit of the present invention, the kit includes nucleic acid molecules comprising nucleotide sequences comprising SEQ ID NO: 129. In another embodiment of the kit of the present invention, the kit includes nucleic acid molecules comprising nucleotide sequences comprising SEQ ID NO: 130. In another embodiment of the kit of the present invention, the kit includes nucleic acid molecules comprising nucleotide sequences comprising SEQ ID NO: 131. In another embodiment of the kit of the present invention, the kit includes nucleic acid molecules comprising nucleotide sequences comprising SEQ ID NO: 132. In another embodiment of the kit of the present invention, the kit includes nucleic acid molecules comprising nucleotide sequences comprising SEQ ID NO: 133. In another embodiment of the kit of the present invention, the kit includes nucleic acid molecules comprising nucleotide sequences comprising SEQ ID NO: 134. In another embodiment of the kit of the present invention, the kit includes nucleic acid molecules comprising nucleotide sequences comprising SEQ ID NO: 135. In another embodiment of the kit of the present invention, the kit includes nucleic acid molecules comprising nucleotide sequences selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof. In another embodiment of the kit of the present invention, the kit includes nucleic acid molecules comprising nucleotide sequences comprising SEQ ID NO: 1 in shNA format. In another embodiment of the kit of the present invention, the kit includes nucleic acid molecules comprising nucleotide sequences comprising SEQ ID NO: 2 in shNA format. In another embodiment of the kit of the present invention, the kit includes nucleic acid molecules comprising nucleotide sequences comprising SEQ ID NO: 3 in shNA format. In another embodiment of the kit of the present invention, the kit includes nucleic acid molecules comprising nucleotide sequences comprising SEQ ID NO: 4 in shNA format. In another embodiment of the kit of the present invention, the kit includes nucleic acid molecules comprising nucleotide sequences comprising SEQ ID NO: 5 in shNA format. In another embodiment of the kit of the present invention, the kit includes nucleic acid molecules comprising nucleotide sequences comprising SEQ ID NO: 6 in shNA format. In another embodiment of the kit of the present invention, the kit includes nucleic acid molecules comprising nucleotide sequences comprising SEQ ID NO: 7 in shNA format. In another embodiment of the kit of the present invention, the kit includes nucleic acid molecules comprising nucleotide sequences comprising SEQ ID NO: 8 in shNA format. In another embodiment of the kit of the present invention, the kit includes nucleic acid molecules comprising nucleotide sequences comprising SEQ ID NO: 9 in shNA format. In another embodiment of the kit of the present invention, the kit includes nucleic acid molecules comprising nucleotide sequences comprising SEQ ID NO: 10 in shNA format. In another embodiment of the kit of the present invention, the kit includes nucleic acid molecules comprising nucleotide sequences comprising SEQ ID NO: 11 in shNA format. In another embodiment of the kit of the present invention, the kit includes nucleic acid molecules comprising nucleotide sequences comprising SEQ ID NO: 12 in shNA format. In another embodiment of the kit of the present invention, the kit includes nucleic acid molecules comprising nucleotide sequences comprising SEQ ID NO: 13 in shNA format. In another embodiment of the kit of the present invention, the kit includes nucleic acid molecules comprising nucleotide sequences comprising SEQ ID NO: 14 in shNA format. In another embodiment of the kit of the present invention, the kit includes nucleic acid molecules comprising nucleotide sequences comprising SEQ ID NO: 15 in shNA format. In another embodiment of the kit of the present invention, the kit includes nucleic acid molecules comprising nucleotide sequences comprising SEQ ID NO: 16 in shNA format. In another embodiment of the kit of the present invention, the kit includes nucleic acid molecules comprising nucleotide sequences comprising SEQ ID NO: 17 in shNA format. In another embodiment of the kit of the present invention, the kit includes nucleic acid molecules comprising nucleotide sequences comprising SEQ ID NO: 18 in shNA format. In another embodiment of the kit of the present invention, the kit includes nucleic acid molecules comprising nucleotide sequences comprising SEQ ID NO: 19 in shNA format. In another embodiment of the kit of the present invention, the kit includes nucleic acid molecules comprising nucleotide sequences comprising SEQ ID NO: 20 in shNA format. In another embodiment of the kit of the present invention, the kit includes nucleic acid molecules comprising nucleotide sequences comprising SEQ ID NO: 21 in shNA format. In another embodiment of the kit of the present invention, the kit includes nucleic acid molecules comprising nucleotide sequences comprising SEQ ID NO: 22 in shNA format. In another embodiment of the kit of the present invention, the kit includes nucleic acid molecules comprising nucleotide sequences comprising SEQ ID NO: 23 in shNA format. In another embodiment of the kit of the present invention, the kit includes nucleic acid molecules comprising nucleotide sequences comprising SEQ ID NO: 24 in shNA format. In another embodiment of the kit of the present invention, the kit includes nucleic acid molecules comprising nucleotide sequences comprising SEQ ID NO: 25 in shNA format. In another embodiment of the kit of the present invention, the kit includes nucleic acid molecules comprising nucleotide sequences comprising SEQ ID NO: 26 in shNA format. In another embodiment of the kit of the present invention, the kit includes nucleic acid molecules comprising nucleotide sequences comprising SEQ ID NO: 27 in shNA format. In another embodiment of the kit of the present invention, the kit includes nucleic acid molecules comprising nucleotide sequences comprising SEQ ID NO: 28 in shNA format. In another embodiment of the kit of the present invention, the kit includes nucleic acid molecules comprising nucleotide sequences comprising SEQ ID NO: 29 in shNA format. In another embodiment of the kit of the present invention, the kit includes nucleic acid molecules comprising nucleotide sequences comprising SEQ ID NO: 30 in shNA format. In another embodiment of the kit of the present invention, the kit includes nucleic acid molecules comprising nucleotide sequences comprising SEQ ID NO: 31 in shNA format. In another embodiment of the kit of the present invention, the kit includes nucleic acid molecules comprising nucleotide sequences comprising SEQ ID NO: 32 in shNA format. In another embodiment of the kit of the present invention, the kit includes nucleic acid molecules comprising nucleotide sequences comprising SEQ ID NO: 33 in shNA format. In another embodiment of the kit of the present invention, the kit includes nucleic acid molecules comprising nucleotide sequences comprising SEQ ID NO: 34 in shNA format. In another embodiment of the kit of the present invention, the kit includes nucleic acid molecules comprising nucleotide sequences comprising SEQ ID NO: 35 in shNA format. In another embodiment of the kit of the present invention, the kit includes nucleic acid molecules comprising nucleotide sequences comprising SEQ ID NO: 36 in shNA format. In another embodiment of the kit of the present invention, the kit includes nucleic acid molecules comprising nucleotide sequences comprising SEQ ID NO: 37 in shNA format. In another embodiment of the kit of the present invention, the kit includes nucleic acid molecules comprising nucleotide sequences comprising SEQ ID NO: 38 in shNA format. In another embodiment of the kit of the present invention, the kit includes nucleic acid molecules comprising nucleotide sequences comprising SEQ ID NO: 39 in shNA format. In another embodiment of the kit of the present invention, the kit includes nucleic acid molecules comprising nucleotide sequences comprising SEQ ID NO: 40 in shNA format. In another embodiment of the kit of the present invention, the kit includes nucleic acid molecules comprising nucleotide sequences comprising SEQ ID NO: 41 in shNA format. In another embodiment of the kit of the present invention, the kit includes nucleic acid molecules comprising nucleotide sequences comprising SEQ ID NO: 42 in shNA format. In another embodiment of the kit of the present invention, the kit includes nucleic acid molecules comprising nucleotide sequences comprising SEQ ID NO: 43 in shNA format. In another embodiment of the kit of the present invention, the kit includes nucleic acid molecules comprising nucleotide sequences comprising SEQ ID NO: 44 in shNA format. In another embodiment of the kit of the present invention, the kit includes nucleic acid molecules comprising nucleotide sequences comprising SEQ ID NO: 45 in shNA format. In another embodiment of the kit of the present invention, the kit includes nucleic acid molecules comprising nucleotide sequences comprising SEQ ID NO: 46 in shNA format. In another embodiment of the kit of the present invention, the kit includes nucleic acid molecules comprising nucleotide sequences comprising SEQ ID NO: 47 in shNA format. In another embodiment of the kit of the present invention, the kit includes nucleic acid molecules comprising nucleotide sequences comprising SEQ ID NO: 48 in shNA format. In another embodiment of the kit of the present invention, the kit includes nucleic acid molecules comprising nucleotide sequences comprising SEQ ID NO: 49 in shNA format. In another embodiment of the kit of the present invention, the kit includes nucleic acid molecules comprising nucleotide sequences comprising SEQ ID NO: 50 in shNA format. In another embodiment of the kit of the present invention, the kit includes nucleic acid molecules comprising nucleotide sequences comprising SEQ ID NO: 51 in shNA format. In another embodiment of the kit of the present invention, the kit includes nucleic acid molecules comprising nucleotide sequences comprising SEQ ID NO: 52 in shNA format. In another embodiment of the kit of the present invention, the kit includes nucleic acid molecules comprising nucleotide sequences comprising SEQ ID NO: 53 in shNA format. In another embodiment of the kit of the present invention, the kit includes nucleic acid molecules comprising nucleotide sequences comprising SEQ ID NO: 54 in shNA format. In another embodiment of the kit of the present invention, the kit includes nucleic acid molecules comprising nucleotide sequences comprising SEQ ID NO: 55 in shNA format. In another embodiment of the kit of the present invention, the kit includes nucleic acid molecules comprising nucleotide sequences comprising SEQ ID NO: 56 in shNA format. In another embodiment of the kit of the present invention, the kit includes nucleic acid molecules comprising nucleotide sequences comprising SEQ ID NO: 57 in shNA format. In another embodiment of the kit of the present invention, the kit includes nucleic acid molecules comprising nucleotide sequences comprising SEQ ID NO: 58 in shNA format. In another embodiment of the kit of the present invention, the kit includes nucleic acid molecules comprising nucleotide sequences comprising SEQ ID NO: 59 in shNA format. In another embodiment of the kit of the present invention, the kit includes nucleic acid molecules comprising nucleotide sequences comprising SEQ ID NO: 60 in shNA format. In another embodiment of the kit of the present invention, the kit includes nucleic acid molecules comprising nucleotide sequences comprising SEQ ID NO: 61 in shNA format. In another embodiment of the kit of the present invention, the kit includes nucleic acid molecules comprising nucleotide sequences comprising SEQ ID NO: 62 in shNA format. In another embodiment of the kit of the present invention, the kit includes nucleic acid molecules comprising nucleotide sequences comprising SEQ ID NO: 63 in shNA format. In another embodiment of the kit of the present invention, the kit includes nucleic acid molecules comprising nucleotide sequences comprising SEQ ID NO: 64 in shNA format. In another embodiment of the kit of the present invention, the kit includes nucleic acid molecules comprising nucleotide sequences comprising SEQ ID NO: 65 in shNA format. In another embodiment of the kit of the present invention, the kit includes nucleic acid molecules comprising nucleotide sequences comprising SEQ ID NO: 66 in shNA format. In another embodiment of the kit of the present invention, the kit includes nucleic acid molecules comprising nucleotide sequences comprising SEQ ID NO: 67 in shNA format. In another embodiment of the kit of the present invention, the kit includes nucleic acid molecules comprising nucleotide sequences comprising SEQ ID NO: 68 in shNA format. In another embodiment of the kit of the present invention, the kit includes nucleic acid molecules comprising nucleotide sequences comprising SEQ ID NO: 69 in shNA format. In another embodiment of the kit of the present invention, the kit includes nucleic acid molecules comprising nucleotide sequences comprising SEQ ID NO: 70 in shNA format. In another embodiment of the kit of the present invention, the kit includes nucleic acid molecules comprising nucleotide sequences comprising SEQ ID NO: 71 in shNA format. In another embodiment of the kit of the present invention, the kit includes nucleic acid molecules comprising nucleotide sequences comprising SEQ ID NO: 72 in shNA format. In another embodiment of the kit of the present invention, the kit includes nucleic acid molecules comprising nucleotide sequences comprising SEQ ID NO: 73 in shNA format. In another embodiment of the kit of the present invention, the kit includes nucleic acid molecules comprising nucleotide sequences comprising SEQ ID NO: 74 in shNA format. In another embodiment of the kit of the present invention, the kit includes nucleic acid molecules comprising nucleotide sequences comprising SEQ ID NO: 75 in shNA format. In another embodiment of the kit of the present invention, the kit includes nucleic acid molecules comprising nucleotide sequences comprising SEQ ID NO: 76 in shNA format. In another embodiment of the kit of the present invention, the kit includes nucleic acid molecules comprising nucleotide sequences comprising SEQ ID NO: 77 in shNA format. In another embodiment of the kit of the present invention, the kit includes nucleic acid molecules comprising nucleotide sequences comprising SEQ ID NO: 78 in shNA format. In another embodiment of the kit of the present invention, the kit includes nucleic acid molecules comprising nucleotide sequences comprising SEQ ID NO: 79 in shNA format. In another embodiment of the kit of the present invention, the kit includes nucleic acid molecules comprising nucleotide sequences comprising SEQ ID NO: 80 in shNA format. In another embodiment of the kit of the present invention, the kit includes nucleic acid molecules comprising nucleotide sequences comprising SEQ ID NO: 81 in shNA format. In another embodiment of the kit of the present invention, the kit includes nucleic acid molecules comprising nucleotide sequences comprising SEQ ID NO: 82 in shNA format. In another embodiment of the kit of the present invention, the kit includes nucleic acid molecules comprising nucleotide sequences comprising SEQ ID NO: 83 in shNA format. In another embodiment of the kit of the present invention, the kit includes nucleic acid molecules comprising nucleotide sequences comprising SEQ ID NO: 84 in shNA format. In another embodiment of the kit of the present invention, the kit includes nucleic acid molecules comprising nucleotide sequences comprising SEQ ID NO: 85 in shNA format. In another embodiment of the kit of the present invention, the kit includes nucleic acid molecules comprising nucleotide sequences comprising SEQ ID NO: 86 in shNA format. In another embodiment of the kit of the present invention, the kit includes nucleic acid molecules comprising nucleotide sequences comprising SEQ ID NO: 87 in shNA format. In another embodiment of the kit of the present invention, the kit includes nucleic acid molecules comprising nucleotide sequences comprising SEQ ID NO: 88 in shNA format. In another embodiment of the kit of the present invention, the kit includes nucleic acid molecules comprising nucleotide sequences comprising SEQ ID NO: 89 in shNA format. In another embodiment of the kit of the present invention, the kit includes nucleic acid molecules comprising nucleotide sequences comprising SEQ ID NO: 90 in shNA format. In another embodiment of the kit of the present invention, the kit includes nucleic acid molecules comprising nucleotide sequences comprising SEQ ID NO: 91 in shNA format. In another embodiment of the kit of the present invention, the kit includes nucleic acid molecules comprising nucleotide sequences comprising SEQ ID NO: 92 in shNA format. In another embodiment of the kit of the present invention, the kit includes nucleic acid molecules comprising nucleotide sequences comprising SEQ ID NO: 93 in shNA format. In another embodiment of the kit of the present invention, the kit includes nucleic acid molecules comprising nucleotide sequences comprising SEQ ID NO: 94 in shNA format. In another embodiment of the kit of the present invention, the kit includes nucleic acid molecules comprising nucleotide sequences comprising SEQ ID NO: 95 in shNA format. In another embodiment of the kit of the present invention, the kit includes nucleic acid molecules comprising nucleotide sequences comprising SEQ ID NO: 96 in shNA format. In another embodiment of the kit of the present invention, the kit includes nucleic acid molecules comprising nucleotide sequences comprising SEQ ID NO: 97 in shNA format. In another embodiment of the kit of the present invention, the kit includes nucleic acid molecules comprising nucleotide sequences comprising SEQ ID NO: 98 in shNA format. In another embodiment of the kit of the present invention, the kit includes nucleic acid molecules comprising nucleotide sequences comprising SEQ ID NO: 99 in shNA format. In another embodiment of the kit of the present invention, the kit includes nucleic acid molecules comprising nucleotide sequences comprising SEQ ID NO: 100 in shNA format. In another embodiment of the kit of the present invention, the kit includes nucleic acid molecules comprising nucleotide sequences comprising SEQ ID NO: 101 in shNA format. In another embodiment of the kit of the present invention, the kit includes nucleic acid molecules comprising nucleotide sequences comprising SEQ ID NO: 102 in shNA format. In another embodiment of the kit of the present invention, the kit includes nucleic acid molecules comprising nucleotide sequences comprising SEQ ID NO: 103 in shNA format. In another embodiment of the kit of the present invention, the kit includes nucleic acid molecules comprising nucleotide sequences comprising SEQ ID NO: 104 in shNA format. In another embodiment of the kit of the present invention, the kit includes nucleic acid molecules comprising nucleotide sequences comprising SEQ ID NO: 105 in shNA format. In another embodiment of the kit of the present invention, the kit includes nucleic acid molecules comprising nucleotide sequences comprising SEQ ID NO: 106 in shNA format. In another embodiment of the kit of the present invention, the kit includes nucleic acid molecules comprising nucleotide sequences comprising SEQ ID NO: 107 in shNA format. In another embodiment of the kit of the present invention, the kit includes nucleic acid molecules comprising nucleotide sequences comprising SEQ ID NO: 108 in shNA format. In another embodiment of the kit of the present invention, the kit includes nucleic acid molecules comprising nucleotide sequences comprising SEQ ID NO: 109 in shNA format. In another embodiment of the kit of the present invention, the kit includes nucleic acid molecules comprising nucleotide sequences comprising SEQ ID NO: 110 in shNA format. In another embodiment of the kit of the present invention, the kit includes nucleic acid molecules comprising nucleotide sequences comprising SEQ ID NO: 114 in shNA format. In another embodiment of the kit of the present invention, the kit includes nucleic acid molecules comprising nucleotide sequences comprising SEQ ID NO: 115 in shNA format. In another embodiment of the kit of the present invention, the kit includes nucleic acid molecules comprising nucleotide sequences comprising SEQ ID NO: 116 in shNA format. In another embodiment of the kit of the present invention, the kit includes nucleic acid molecules comprising nucleotide sequences comprising SEQ ID NO: 117 in shNA format. In another embodiment of the kit of the present invention, the kit includes nucleic acid molecules comprising nucleotide sequences comprising SEQ ID NO: 118 in shNA format. In another embodiment of the kit of the present invention, the kit includes nucleic acid molecules comprising nucleotide sequences comprising SEQ ID NO: 119 in shNA format. In another embodiment of the kit of the present invention, the kit includes nucleic acid molecules comprising nucleotide sequences comprising SEQ ID NO: 120 in shNA format. In another embodiment of the kit of the present invention, the kit includes nucleic acid molecules comprising nucleotide sequences comprising SEQ ID NO: 121 in shNA format. In another embodiment of the kit of the present invention, the kit includes nucleic acid molecules comprising nucleotide sequences comprising SEQ ID NO: 122 in shNA format. In another embodiment of the kit of the present invention, the kit includes nucleic acid molecules comprising nucleotide sequences comprising SEQ ID NO: 123 in shNA format. In another embodiment of the kit of the present invention, the kit includes nucleic acid molecules comprising nucleotide sequences comprising SEQ ID NO: 124 in shNA format. In another embodiment of the kit of the present invention, the kit includes nucleic acid molecules comprising nucleotide sequences comprising SEQ ID NO: 125 in shNA format. In another embodiment of the kit of the present invention, the kit includes nucleic acid molecules comprising nucleotide sequences comprising SEQ ID NO: 126 in shNA format. In another embodiment of the kit of the present invention, the kit includes nucleic acid molecules comprising nucleotide sequences comprising SEQ ID NO: 127 in shNA format. In another embodiment of the kit of the present invention, the kit includes nucleic acid molecules comprising nucleotide sequences comprising SEQ ID NO: 128 in shNA format. In another embodiment of the kit of the present invention, the kit includes nucleic acid molecules comprising nucleotide sequences comprising SEQ ID NO: 129 in shNA format. In another embodiment of the kit of the present invention, the kit includes nucleic acid molecules comprising nucleotide sequences comprising SEQ ID NO: 130 in shNA format. In another embodiment of the kit of the present invention, the kit includes nucleic acid molecules comprising nucleotide sequences comprising SEQ ID NO: 131 in shNA format. In another embodiment of the kit of the present invention, the kit includes nucleic acid molecules comprising nucleotide sequences comprising SEQ ID NO: 132 in shNA format. In another embodiment of the kit of the present invention, the kit includes nucleic acid molecules comprising nucleotide sequences comprising SEQ ID NO: 133 in shNA format. In another embodiment of the kit of the present invention, the kit includes nucleic acid molecules comprising nucleotide sequences comprising SEQ ID NO: 134 in shNA format. In another embodiment of the kit of the present invention, the kit includes nucleic acid molecules comprising nucleotide sequences comprising SEQ ID NO: 135 in shNA format. In another embodiment of the kit of the present invention, the kit includes nucleic acid molecules comprising nucleotide sequences selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; SEQ ID NO: 42; SEQ ID NO: 43; SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53; SEQ ID NO: 54; SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; SEQ ID NO: 72; SEQ ID NO: 73; SEQ ID NO: 74; SEQ ID NO: 75; SEQ ID NO: 76; SEQ ID NO: 77; SEQ ID NO: 78; SEQ ID NO: 79; SEQ ID NO: 80; SEQ ID NO: 81; SEQ ID NO: 82; SEQ ID NO: 83; SEQ ID NO: 84; SEQ ID NO: 85; SEQ ID NO: 86; SEQ ID NO: 87; SEQ ID NO: 88; SEQ ID NO: 89; SEQ ID NO: 90; SEQ ID NO: 91; SEQ ID NO: 92; SEQ ID NO: 93; SEQ ID NO: 94; SEQ ID NO: 95; SEQ ID NO: 96; SEQ ID NO: 97; SEQ ID NO: 98; SEQ ID NO: 99; SEQ ID NO: 100; SEQ ID NO: 101; SEQ ID NO: 102; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 114; SEQ ID NO: 115; SEQ ID NO: 116; SEQ ID NO: 117; SEQ ID NO: 118; SEQ ID NO: 119; SEQ ID NO: 120; SEQ ID NO: 121; SEQ ID NO: 122; SEQ ID NO: 123; SEQ ID NO: 124; SEQ ID NO: 125; SEQ ID NO: 126; SEQ ID NO: 127; SEQ ID NO: 128; SEQ ID NO: 129; SEQ ID NO: 130; SEQ ID NO: 131; SEQ ID NO: 132; SEQ ID NO: 133; SEQ ID NO: 134; SEQ ID NO: 135; and combinations thereof in shNA format.

In another embodiment of the kit of the present invention, the kit comprises a vector comprising an expression cassette. In another embodiment of the kit of the present invention, the vector is a viral vector. In another embodiment of the kit of the present invention, the vector is an adenoviral virus vector. In another embodiment of the kit of the present invention, the vector is a retroviral virus vector (e.g. lentivirus, Rous sarcoma virus, Harvey sarcoma virus, Moloney murine leukemia virus, feline immunodeficiency virus). In another embodiment of the kit of the present invention, the vector is a parvoviral virus vector (e.g. adeno-associated virus (AAV)). In another embodiment of the kit of the present invention, the vector is a picornaviral virus vector (e.g. poliovirus). In another embodiment of the kit of the present invention, the vector is a herpes virus vector (e.g. herpes simplex virus).

BRIEF DESCRIPTION OF THE FIGURES

FIG. 3 depicts a structure and construction of anti-htt (FIG. 3A, SEQ ID NOs: 112 and 148) and control (FIG. 3B, SEQ ID NOs: 113 and 149) shNA sequences.

DETAILED DESCRIPTION OF THE INVENTION

Figure 1:
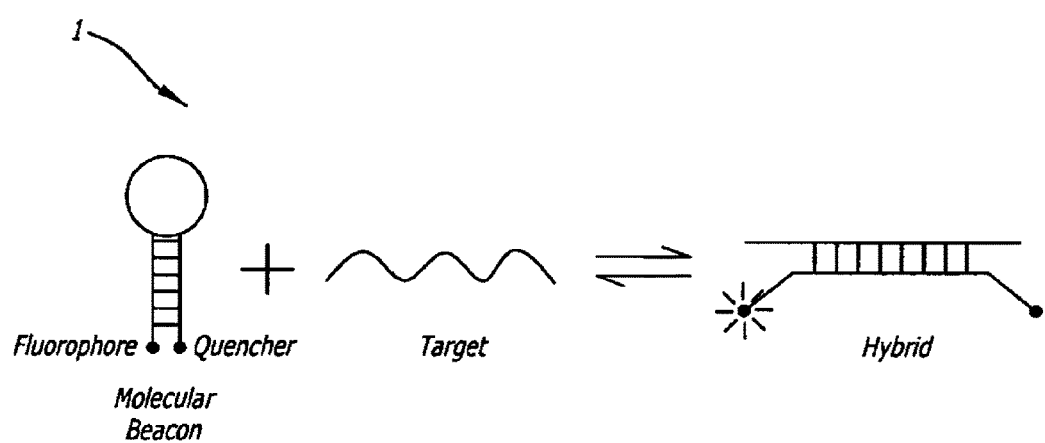
FIG. 1 shows the basic structure and operation principles of molecular beacons.

The terms "nucleic acid" or "nucleic acid molecules" refer to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues. The nucleic acid molecules of the present invention can include any type of nucleic acid molecule capable of mediating RNA interference, such as, without limitation, short interfering nucleic acid (siNA), short hairpin nucleic acid (shNA), short interfering RNA (siRNA), short hairpin RNA (shRNA), micro-RNA (miRNA), and double-stranded RNA (dsRNA). The nucleic acid molecules of the present invention also include DNA sequences that encode for nucleic acid molecules capable of mediating RNA interference, such as, without limitation, siNA, shNA, siRNA, shRNA, miRNA, and dsRNA. Further, the nucleic acid and nucleic acid molecules of the present invention can contain unmodified or modified nucleotides. Modified nucleotides refer to nucleotides which contain a modification in the chemical structure of a nucleotide base, sugar and/or phosphate. Such modifications can be made to improve the stability and/or efficacy of nucleic acid molecules and are described in patents and publications such as U.S. Pat. No. ("USPN") 6,617,438, U.S. Pat. Nos. 5,334,711 ; 5,716,824; and 5,627,053; U.S. Patent Application No. 60/082,404; International Patent Cooperation Treaty Publication Number ("PCTPN") WO 98/13526; PCTPN WO 92/07065; PCTPN WO 03/070897; PCTPN WO 97/26270; PCTPN WO 93/15187; Beigelman et al., 1995, J Biol Chem, 270, 25702-8; Usman and Cedergren, 1992, Trends Biochem Sci 17, 334-9; Usman et al., 1994, Nucleic Acids Symp Ser 31, 163; Burgin et al., 1996, Biochemistry, 35, 14090-7; Perreault et al. Nature, 1990, 344, 565-567; Pieken et al., 1991, Science, 253, 314-7; Karpeisky et al., 1998, Tetrahedron Lett, 39, 1131-4; Earnshaw and Gait, 1998, Biopolymers (Nucleic Acid Sciences), 48, 39-55; Verma and Eckstein, 1998, Annu Rev Biochem, 67, 99-134; Burlina et al., 1997, Bioorg Med Chem, 5, 1999-2010; Limbach et al., 1994, Nucleic Acids Res 22, 2183-96; and Burgin et al., 1996, Biochemistry, 35, 14090-7. Such patents and publications describe general methods and strategies to modify nucleic acid molecules and as such define the state of the art. Thus, those having ordinary skill in the art of molecular biology would readily understand the techniques and methods described in the above-identified references and no further teaching is required. However, the above-cited reference are hereby incorporated by reference herein in their entirety to the extent further teachings are required for a complete and full understanding of the techniques, compositions and methods described herein.

The phrase "expression cassette" as used herein means a nucleic acid sequence capable of directing expression of a particular nucleotide sequence in an appropriate host cell with additional sequences that facilitate appropriate transcription of the nucleic acid sequence of interest. In addition to the nucleotide sequence of interest, the expression cassette can include a promoter operably linked to the nucleotide sequence of interest that also can be operably linked to termination signals. The expression cassette also can include expression enhancers. The expression cassette including the nucleotide sequence of interest can be chimeric. The expression cassette also can be one that is naturally occurring but has been obtained in a recombinant form useful for heterologous expression. The expression of the nucleotide sequence in the expression cassette can be under the control of a constitutive promoter or of a regulatable promoter that initiates transcription only when the host cell is exposed to some particular stimulus. In the case of a multicellular organism, the promoter also can be specific to a particular tissue or organ or stage of development.

The term "promoter" refers to a nucleotide sequence, usually upstream (5) of the nucleotide sequence of interest, which directs and/or controls expression of the nucleotide sequence of interest by providing for recognition by RNA polymerase and other factors required for proper transcription. As used herein, the term "promoter" includes a minimal promoter that is a short DNA sequence and other sequences that serve to specify the site of transcription initiation, to which regulatory elements are added for control of expression. The term "promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. The term "enhancer" refers to a DNA sequence that can stimulate promoter activity and can be an innate element of the promoter or a heterologous element inserted to enhance the level or tissue specificity of a promoter. Enhancers are capable of operating in both orientations (normal or flipped), and are capable of functioning even when moved either upstream or downstream of the promoter. Both enhancers and other upstream promoter elements bind sequence-specific DNA-binding proteins that mediate their effects. Promoters can be derived in their entirety from a native gene, or be composed of different elements derived from different promoters found in nature, or even be comprised of synthetic DNA segments. A promoter also can contain DNA sequences that are involved in the binding of protein factors that control the effectiveness of transcription initiation in response to physiological or developmental conditions. Specific promoters used in accordance with the present invention can include, for example and without limitation pol II promoters (including, without limitation cytomegalovirus ("CMV") promoters, chicken .beta.-actin ("CBA") promoters, Rous sarcoma virus ("RSV") promoters and neuron-specific enolase ("NSE") promoters) and pol III promoters.

The term "vector" is defined to include any virus, as well as any plasmid, cosmid, phage or binary vector in double or single stranded linear or circular form that may or may not be self transmissible or mobilizable, and that can transform eukaryotic host cells either by integration into the cellular genome or by existing extrachromosomally (e.g., autonomous replicating plasmid with an origin of replication).

The gene (IT-15) involved in Huntington's disease ("HD") is located on chromosome 4 at the end of the short arm. This gene encodes for the protein huntingtin ("htt"). The mutation in the HD gene responsible for HD is an unstable expanded CAG trinucleotide repeat within the coding region of the gene. This mutation results in an htt protein with an expanded polyglutamine sequence. While the normal and abnormal functions of normal and mutated hit are not known, the presence of the mutated form of htt has been correlated with the occurrence of HD symptoms. Further, the abnormal htt protein appears to misfold and aggregate in brain cells, such as neurons, due to the presence of the expanded polyglutamine sequence.

Recently, a number of single nucleotide polymorphisms (SNPs) have been identified in the HD gene through the National Center for Biotechnology Information ("NCBI") nucleotide website. These SNPs provide an avenue to use RNAi to preferentially suppress expression of the HD-causing gene allele. Individual identified SNPs were selected with use of the basic local alignment search tool ("BLAST" analysis; NCBI). The selected SNPs included:

TABLE 1

| SEQ ID NO: | Nucleic Acid Sequence Name | Target Gene* | Nucleotide Base Sequence | Position of SNP cDNA of NM_002111.3 |
|---|---|---|---|---|
| 1 | SNP01a T allele | HD | 5'-AGGCCTTCATAGCGAACCT-3' | 1079 |
| 2 | SNP01b C allele | HD | 5'-AGGCCTTCACAGCGAACCT-3' | 1079 |
| 3 | SNP02a G allele | HD | 5'-AAATGTGCTGTTAGGCTTA-3' | 1197 |
| 4 | SNP02b C allele | HD | 5'-AAATGTGCTCTTAGGCTTA-3' | 1197 |
| 5 | SNP03a A allele | HD | 5'-CAATAAAGGAAGCCTTGCC-3' | 3812 |
| 6 | SNP03b C allele | HD | 5'-CAATAAAGGCAGCCTTGCC-3' | 3812 |
| 7 | SNP04a C allele | HD | 5'-AGGGTTTCTCCGCTCAGCC-3' | 4113 |
| 8 | SNP04b T allele | HD | 5'-AGGGTTTCTTCGCTCAGCC-3' | 4113 |
| 9 | SNP05a A allele | HD | 5'-GAGCAGGAGAACGACACCT-3' | 4465 |
| 10 | SNP05b C allele | HD | 5'-GAGCAGGAGCACGACACCT-3' | 4465 |
| 11 | SNP06a C allele | HD | 5'-TAAGAGGAACAAATAAAGC-3' | 4976 |
| 12 | SNP06b T allele | HD | 5'-TAAGAGGAATAAATAAAGC-3' | 4976 |
| 13 | SNP07a C allele | HD | 5'-GGGACAGTACTTCAACGCT-3' | 5471 |
| 14 | SNP07b A allele | HD | 5'-GGGACAGTAATTCAACGCT-3' | 5471 |
| 15 | SNP08a T allele | HD | 5'-TCCCTCATCTACTGTGTGC-3' | 7237 |
| 16 | SNP08b C allele | HD | 5'-TCCCTCATCCACTGTGTGC-3' | 7237 |
| 17 | SNP09a C allele | HD | 5'-CCGCATCAACACACTAGGC-3' | 7674 |
| 18 | SNP09b T allele | HD | 5'-CCGCATCAATACACTAGGC-3' | 7674 |
| 19 | SNP10a C allele | HD | 5'-CTGGTGACGCAGCCCCTCG-3' | 7744 |
| 20 | SNP10b T allele | HD | 5'-CTGGTGACGTAGCCCCTCG-3' | 7744 |

TABLE 1-continued

| SEQ ID NO: | Nucleic Acid Sequence Name | Target Gene* | Nucleotide Base Sequence | Position of SNP cDNA of NM_002111.3 |
|---|---|---|---|---|
| 21 | SNP11a T allele | HD | 5'-AAGCCCATATCACCGGCTG-3' | 9690 |
| 22 | SNP11b C allele | HD | 5'-AAGCCCATACCACCGGCTG-3' | 9690 |

*SNPs bolded.

As will be explained more fully below, testing performed on the SNPs listed in the preceding table demonstrated that of 21 HD patients tested, 9% were heterozygous for SNP02; 33% were heterozygous for SNP04; 14% were heterozygous for SNP07; and 48% were heterozygous for SNP08. None of the 21 patients tested were heterozygous for SNP01 (T on both alleles); SNP03 (C on both alleles); SNP05 (A on both alleles); SNP06 (C on both alleles); SNP09 (all C on both alleles); SNP10 (C on both alleles); and SNP11 (T on both alleles). Of all 21 cell lines from HD patients tested 10 were heterozygous for one or more of the above mentioned SNPs. This data demonstrates that while some patients can be homozygous for all of these 11 SNPs within the HD gene, many are heterozygous for at least one known SNP of the HD genes.

Note that, as will be understood by one of ordinary skill in the art, the nucleic acid molecules of the present invention will include, without limitation, all nucleic acid sequences targeting the SNPs in the preceding table, the reverse complement of these sequences and RNA based sequences including uracils in the place of the listed thymines. In addition, the RNA interfering nucleic acids can also be created by shifting the sequence up- or downstream from the sequences in the preceding table. Furthermore allele specificity of siNA or shNA can also be achieved by creating extra mismatches in the sequence. Non-limiting examples of nucleic acid sequences targeting SNPs in the preceding table (following the respective targeted sequence) include:

TABLE 2

| SEQ ID NO. | Nucleotide Base Sequence |
|---|---|
| 1 | 5' AGGCCTTCATAGCGAACCT 3' |
| 23 | 5' GGCCTTCATAGCGAACCTG 3' |
| 24 | 5' GCCTTCATAGCGAACCTGA 3' |
| 25 | 5' AAGGCCTTCATAGCGAACC 3' |
| 26 | 5' AAAGGCCTTCATAGCGAAC 3' |
| 2 | 5' AGGCCTTCACAGCGAACCT 3' |
| 27 | 5' GGCCTTCACAGCGAACCTG 3' |
| 28 | 5' GCCTTCACAGCGAACCTGA 3' |
| 29 | 5' AAGGCCTTCACAGCGAACC 3' |
| 30 | 5' AAAGGCCTTCACAGCGAAC 3' |
| 3 | 5' AAATGTGCTGTTAGGCTTA 3' |
| 31 | 5' TAAATGTGCTGTTAGGCTT 3' |
| 32 | 5' CTAAATGTGCTGTTAGGCT 3' |
| 33 | 5' AATGTGCTGTTAGGCTTAC 3' |
| 34 | 5' ATGTGCTGTTAGGCTTACT 3' |
| 114 | 5' AAATGTGCTGTGAGGCTTA 3' |
| 115 | 5' GCTACTAAATGTGCTGTTA 3' |
| 4 | 5' AAATGTGCTCTTAGGCTTA 3' |
| 35 | 5' TAAATGTGCTCTTAGGCTT 3' |
| 36 | 5' CTAAATGTGCTCTTAGGCT 3' |
| 37 | 5' AATGTGCTCTTAGGCTTAC 3' |
| 38 | 5' ATGTGCTCTTAGGCTTACT 3' |
| 116 | 5' AAATGTGCTCTGAGGCTTA 3' |
| 117 | 5' GCTACTAAATGTGCTCTTA 3' |
| 5 | 5' TATTTTAGGAAGCCTTGCC 3' |
| 39 | 5' GCAATAAAGGAGCCTTGC 3' |
| 40 | 5' CGCAATAAAGGAAGCCTTG 3' |
| 41 | 5' AATAAAGGAAGCCTTGCCT 3' |
| 42 | 5' ATAAAGGAAGCCTTGCCTT 3' |
| 6 | 5' TATTTTAGGCAGCCTTGCC 3' |
| 43 | 5' GCAATAAAGGCAGCCTTGC 3' |
| 44 | 5' CGCAATAAAGGCAGCCTTG 3' |
| 45 | 5' AATAAAGGCAGCCTTGCCT 3' |
| 46 | 5' ATAAAGGCAGCCTTGCCTT 3' |
| 7 | 5' AGGGTTTCTCCGCTCAGCC 3' |
| 47 | 5' GAGGGTTTCTCCGCTCAGC 3' |
| 48 | 5' GGAGGGTTTCTCCGCTCAG 3' |
| 49 | 5' GGGTTTCTCCGCTCAGCCT 3' |
| 50 | 5' GGTTTCTCCGCTCAGCCTT 3' |
| 118 | 5' GTTTGGAGGGTTTCTCCGC 3' |
| 119 | 5' AGGGTTTCTCCTCTCAGCC 3' |
| 120 | 5' AGGGTTTCTCCACTCAGCC 3' |

TABLE 2-continued

| SEQ ID NO. | Nucleotide Base Sequence |
|---|---|
| 8 | 5' AGGGTTTCTTCGCTCAGCC 3' |
| 51 | 5' GAGGGTTTCTTCGCTCAGC 3' |
| 52 | 5' GGAGGGTTTCTTCGCTCAG 3' |
| 53 | 5' GGGTTTCTTCGCTCAGCCT 3' |
| 54 | 5' GGTTTCTTCGCTCAGCCTT 3' |
| 121 | 5' GTTTGGAGGGTTTCTTCGC 3' |
| 122 | 5' AGGGTTTCTTCTCTCAGCC 3' |
| 123 | 5' AGGGTTTCTTCACTCAGCC 3' |
| 9 | 5' GAGCAGGAGAACGACACCT 3' |
| 55 | 5' GGAGCAGGAGAACGACACC 3' |
| 56 | 5' CGGAGCAGGAGAACGACAC 3' |
| 57 | 5' AGCAGGAGAACGACACCTC 3' |
| 58 | 5' GCAGGAGAACGACACCTCG 3' |
| 10 | 5' GAGCAGGAGCACGACACCT 3' |
| 59 | 5' GGAGCAGGAGCACGACACC 3' |
| 60 | 5' CGGAGCAGGAGCACGACAC 3' |
| 61 | 5' AGCAGGAGCACGACACCTC 3' |
| 62 | 5' GCAGGAGCACGACACCTCG 3' |
| 11 | 5' TAAGAGGAACAAATAAAGC 3' |
| 63 | 5' TTAAGAGGAACAAATAAAG 3' |
| 64 | 5' ATTAAGAGGAACAAATAAA 3' |
| 65 | 5' AAGAGGAACAAATAAAGCT 3' |
| 66 | 5' AGAGGAACAAATAAAGCTG 3' |
| 12 | 5' TAAGAGGAATAAATAAAGC 3' |
| 67 | 5' TTAAGAGGAATAAATAAAG 3' |
| 68 | 5' ATTAAGAGGAATAAATAAA 3' |
| 69 | 5' AAGAGGAATAAATAAAGCT 3' |
| 70 | 5' AGAGGAATAAATAAAGCTG 3' |
| 13 | 5' GGGACAGTACTTCAACGCT 3' |
| 71 | 5' GGACAGTACTTCAACGCTA 3' |
| 72 | 5' GACAGTACTTCAACGCTAG 3' |
| 73 | 5' GGGGACAGTACTTCAACGC 3' |
| 74 | 5' TGGGGACAGTACTTCAACG 3' |
| 124 | 5' GGACAGTACATCAACGCTA 3' |
| 125 | 5' GAGATGGGGACAGTACTTC 3' |
| 126 | 5' GGGGACAGTACTTAAACGC 3' |
| 14 | 5' GGGACAGTAATTCAACGCT 3' |
| 75 | 5' GGACAGTAATTCAACGCTA 3' |
| 76 | 5' GACAGTAATTCAACGCTAG 3' |
| 77 | 5' GGGGACAGTAATTCAACGC 3' |
| 78 | 5' TGGGGACAGTAATTCAACG 3' |
| 127 | 5' GGACAGTAAGTCAACGCTA 3' |
| 128 | 5' GAGATGGGGACAGTAATTC 3' |
| 129 | 5' GGGGACAGTAATTAAACGC 3' |
| 15 | 5' TCCCTCATCTACTGTGTGC 3' |
| 79 | 5' CTCCCTCATCTACTGTGTG 3' |
| 80 | 5' GCTCCCTCATCTACTGTGT 3' |
| 81 | 5' CCCTCATCTACTGTGTGCA 3' |
| 82 | 5' CCTCATCTACTGTGTGCAC 3' |
| 130 | 5' GCCTGCTCCCTCATCTACT 3' |
| 131 | 5' TCCCTCATCTACTGGGTGC 3' |
| 132 | 5' TCCCTCATCTACGGTGTGC 3' |
| 16 | 5' TCCCTCATCCACTGTGTGC 3' |
| 83 | 5' CTCCCTCATCCACTGTGTG 3' |
| 84 | 5' GCTCCCTCATCCACTGTGT 3' |
| 85 | 5' CCCTCATCCACTGTGTGCA 3' |
| 86 | 5' CCTCATCCACTGTGTGCAC 3' |
| 133 | 5' GCCTGCTCCCTCATCCACT 3' |
| 134 | 5' TCCCTCATCCACTGGGTGC 3' |
| 135 | 5' TCCCTCATCCACGGTGTGC 3' |
| 17 | 5'-CCGCATCAACACACTAGGT-3' |
| 87 | 5' ACCGCATCAACACACTAGG 3' |
| 88 | 5' TACCGCATCAACACACTAG 3' |
| 89 | 5' CGCATCAACACACTAGGCT 3' |
| 90 | 5' GCATCAACACACTAGGCTG 3' |
| 18 | 5'-CCGCATCAATACACTAGGT-3' |
| 91 | 5' ACCGCATCAATACACTAGG 3' |
| 92 | 5' TACCGCATCAATACACTAG 3' |
| 93 | 5' CGCATCAATACACTAGGCT 3' |
| 94 | 5' GCATCAATACACTAGGCTG 3' |
| 19 | 5'-CTGGTGACGCAGCCCCTCG-3' |
| 95 | 5' CCTGGTGACGCAGCCCCTC 3' |
| 96 | 5' TCCTGGTGACGCAGCCCCT 3' |
| 97 | 5' TGGTGACGCAGCCCCTCGT 3' |
| 98 | 5' GGTGACGCAGCCCCTCGTG 3' |
| 20 | 5'-CTGGTGACGTAGCCCCTCG-3' |
| 99 | 5' CCTGGTGACGTAGCCCCTC 3' |
| 100 | 5' TCCTGGTGACGTAGCCCCT 3' |

TABLE 2-continued

| SEQ ID NO. | Nucleotide Base Sequence |
|---|---|
| 101 | 5' TGGTGACGTAGCCCCTCGT 3' |
| 102 | 5' GGTGACGTAGCCCCTCGTG 3' |
| 21 | 5'-AAGCCCATATCACCGGCTG-3' |
| 103 | 5' GAAGCCCATATCACCGGCT 3' |
| 104 | 5' GGAAGCCCATATCACCGGC 3' |
| 105 | 5' AGCCCATATCACCGGCTGC 3' |
| 106 | 5' GCCCATATCACCGGCTGCT 3' |
| 22 | 5'-AAGCCCATACCACCGGCTG-3' |
| 107 | 5' GAAGCCCATACCACCGGCT 3' |
| 108 | 5' GGAAGCCCATACCACCGGC 3' |
| 109 | 5' AGCCCATACCACCGGCTGC 3' |
| 110 | 5' GCCCATACCACCGGCTGCT 3' |

* extra mismatches underlined

Again, and as will be understood by one of skill in the art, the nucleic acid molecules of the present invention include the sequences in the preceding table, the reverse complement of these sequences and RNA based sequences including uracils in the place of the listed thymines. Thus, the sequences in the preceding table can be considered target sequences as well as sequences included in the nucleic acid molecules of the present invention.

To identify SNPs present in only one allele of an individual's HD genes (in one embodiment a given HD patient's), in one method, the sequences in the preceding tables, among others, can be formatted into molecular beacons. Molecular beacons are single-stranded nucleic acid molecules with stem and loop structures that fluoresce on hybridization to their perfectly complementary targets. As shown in FIG. 1, the loop portion is complementary to a predetermined sequence in a target nucleic acid (in this invention, portions of the HD gene). The stem is formed by the binding of complementary arm sequences on each side of the loop sequence. A fluorophore moiety is covalently linked to the end of one arm and a quenching moiety is linked to the end of the other arm. When molecular beacons are free in solution, the stem keeps the two moieties of the molecular beacon in close proximity to each other, so that fluorescence is quenched. When molecular beacons hybridize to their perfectly complementary targets, however, they undergo a conformational change. The conformational change causes the fluorophore and the quencher to separate allowing the fluorophore to fluoresce. At temperatures between the dissociation temperature of perfectly complementary hybrids and mismatched hybrids, perfectly complementary targets can be distinguished from mismatched targets by higher fluorescence. By using different colors of fluorescence on different molecular beacon sequences, this technique can be used to detect multiple SNPs within HD genes in a given sample. This technique, which is described in, for example, Mhlanga & Malmberg, 2001, Methods, 25, 463-471, which is hereby incorporated by reference, also can be used for testing the allele-specificity of the siNA molecules of the present invention by using molecular beacon-based real time RT-PCR reactions in which the molecular beacons used specifically target a SNP position on HD gene cDNA.

Primers for PCR using molecular beacons are designed to flank the loop sequence with the molecular beacon sequence approximately 20-30 bases 3' or 5' of the forward or reverse primer, respectively. For real time detection of SNPs, molecular beacons are designed to be complementary to a region of the amplicon where the SNP of interest occurs. The loop region of the molecular beacon generally is designed first and usually contains between approximately 15 and 30 nucleotides. This length gives a melting temperature that is slightly above the annealing temperature of the PCR which causes the molecular beacon/SNP of interest hybrid to be stable during annealing when signal detection takes place. The arm length sequences generally are designed next. These sequences often are approximately 5-7 nucleotides in length. This length allows the stems to melt at about 7-10° C. higher than the optimal annealing temperature of the involved primer set. As stated earlier, the sequences in the preceding tables as well as their reverse complements and corresponding RNA sequences can be formatted into molecular beacons.

To evaluate the effectiveness of nucleic acid sequences at suppressing expression of the mutated HD gene, appropriate cell lines for the studies were initially evaluated. First, fibroblast cells of 21 different HD patient families were purchased from the Coriel cell repository and tested for heterozygosity of the 11 SNPs identified in the first table (SEQ ID NOS. 1-22). Of the 21 different fibroblast cell lines, ten were identified as heterozygous for one or more of the identified SNPs. Specifically, two cell lines (GM02155 and GM04022) were found to be heterozygous (C/G) for SNP 2 (SEQ ID NO. 3 and SEQ ID NO. 4); seven cell lines (GM01061, GM02147, GM02173, GM02191, GM01169, GM04196 and GM09197) were found to be heterozygous (A/G) for SNP 4 (SEQ ID NO. 7 and SEQ ID NO. 8); three cell lines (GM01171, GM02155 and GM04022) were found to be heterozygous (G/T) for SNP 7 (SEQ ID NO. 13 and SEQ ID NO. 14) and 10 cell lines (GM01061, GM01171, GM02147, GM02155, GM02173, GM02191, GM01169, GM04022, GM04196 and GM09197) were found to be heterozygous (A/G) for SNP 8 (SEQ ID NO. 15 and SEQ ID NO. 16). Stated another way, cell lines GM01061, GM02147, GM02173, GM02191, GM01169, GM04196 and GM09197 are heterozygous for SNPs 4 and 8 (SEQ ID NO. 7 and SEQ ID NO. 8 and SEQ ID NO. 15 and SEQ ID NO. 16); cell line GM01171 is heterozygous for SNPs 7 and 8 (SEQ ID NO. 13 and SEQ ID NO. 14 and SEQ ID NO. 15 and SEQ ID NO. 16); and cell lines GM02155 and GM04022 are heterozygous for SNPs 2, 7 and 8 (SEQ ID NO. 3 and SEQ ID NO. 4 and SEQ ID NO. 13 and SEQ ID NO. 14 and SEQ ID NO. 15 and SEQ ID NO. 16). Thus, these cell lines that are heterozygous for the identified SNPs are appropriate cell lines to study the effectiveness of one or more of SEQ ID. NOS: 3, 4, 7, 8, 13-16, 31-38, 47-54, 71-86 and 114-135 at preferentially suppressing one selected HD allele. To study the effectiveness of nucleic acid sequences not identified as heterozygous in the studied cell lines, cell types that do not contain human HD genes can be cotransfected with a plasmid containing gene sequences of interest and a particular sequence directed against a gene sequence of interest (the mutated HD gene). For these studies, as non-limiting examples, appropriate canine or bovine cell lines could be chosen.

Once appropriate cell lines are identified as described above, in vitro transfection or cotransfection assay systems can be used to study the effectiveness of the identified sequences at suppressing expression of the mutated HD gene allele (and subsequent production of an expanded polyglutamine htt protein). In the human cell lines containing SNPs of interest, DNA sequences encoding for a siNA or shNA sequence directed against the mutated HD gene containing a particular SNP can be transfected into the cells through the use of an appropriate plasmid. Specifically, the sequence of interest (or a non-sense scrambled control, such as, in one embodiment, SEQ ID. NO. 111 (TAGCGAC-TAAACACATCAA)) can be subcloned into a plasmid that includes a GFP-Zeocin reporter gene for transfection efficiency normalization. The CMV promoter can direct constitutive expression of the DNA sequence encoding for the chosen siNA, shNA, or control sequence while the EF1 promoter can direct constitutive expression of the GFP-Zeocin reporter gene. The generated recombinant plasmid can be used to facilitate screening of the particular nucleic acid sequence included in the recombinant plasmid by transfection into the appropriately-identified fibroblast cell lines. Forty-eight hours post-transfection, total cellular RNA can be harvested from the cells and used to make cDNA by standard methods. The cDNAs can be analyzed for normal and mutated HD gene as well as reporter (GFP) gene expression levels using real time PCR methods. The data can be normalized for GFP expression levels to control for variation in transfection efficiency. As will be recognized by one of skill in the art, screening also can be accomplished by Northern blot evaluation of transcripts harvested from transfected cells, by measuring siNA-mediated reduction of targeted protein levels and other techniques known to those of skill in the art.

Figure 2:
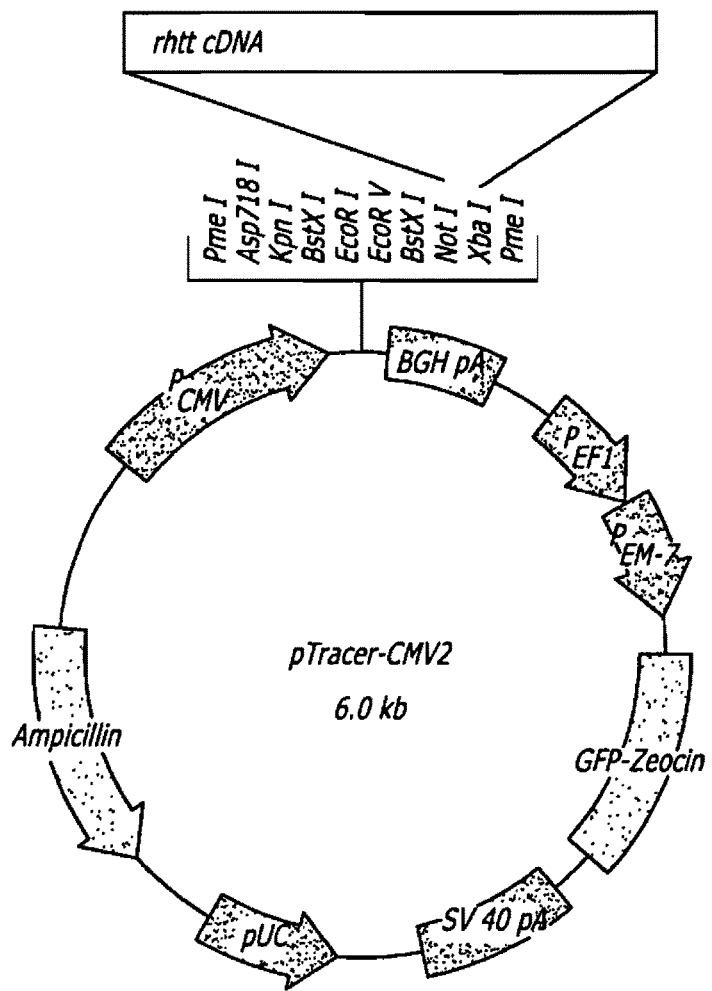
FIG. 2 shows a potential target plasmid for nucleic acid sequence characterization studies.

Alternatively, and referring to FIG. 2, HD gene sequences can be subcloned into pTracer™-CMV2 (Invitrogen, Corp., Carlsbad, Calif.) to generate pTracer-rhtt. This recombinant plasmid also can include a GFP-Zeocin reporter gene for transfection efficiency normalization. The CMV promoter can direct constitutive expression of the target genes (normal and mutated rhtt) while the EF1 promoter can direct constitutive expression of the GFP-Zeocin reporter gene.

The generated recombinant plasmids can be used to facilitate screening of nucleic acid sequences by co-transfection into appropriately-identified cell lines. In one example, the cells can be cultured at 60-70% confluency and can be co-transfected with the appropriate target plasmid and a test nucleic acid sequence (such as a DNA sequence encoding for a chosen siNA or shNA sequence) directed against the mutated HD gene sequence (or a non-sense scrambled control (in one embodiment, SEQ ID NO. 111)). Forty-eight hours post-transfection, total cellular RNA can be harvested from the cells and used to make cDNA by standard methods. The cDNAs can be analyzed for normal and mutated HD gene as well as reporter (GFP) gene expression levels using real time PCR methods. The data can be normalized for GFP expression levels to control for variation in transfection efficiency. Again, as will be recognized by one of ordinary skill in the art, screening also can be accomplished by Northern blot evaluation of transcripts harvested from transfected cells, by measuring siNA-mediated reduction of targeted protein levels and other techniques known to those of skill in the art.

Figure 4:
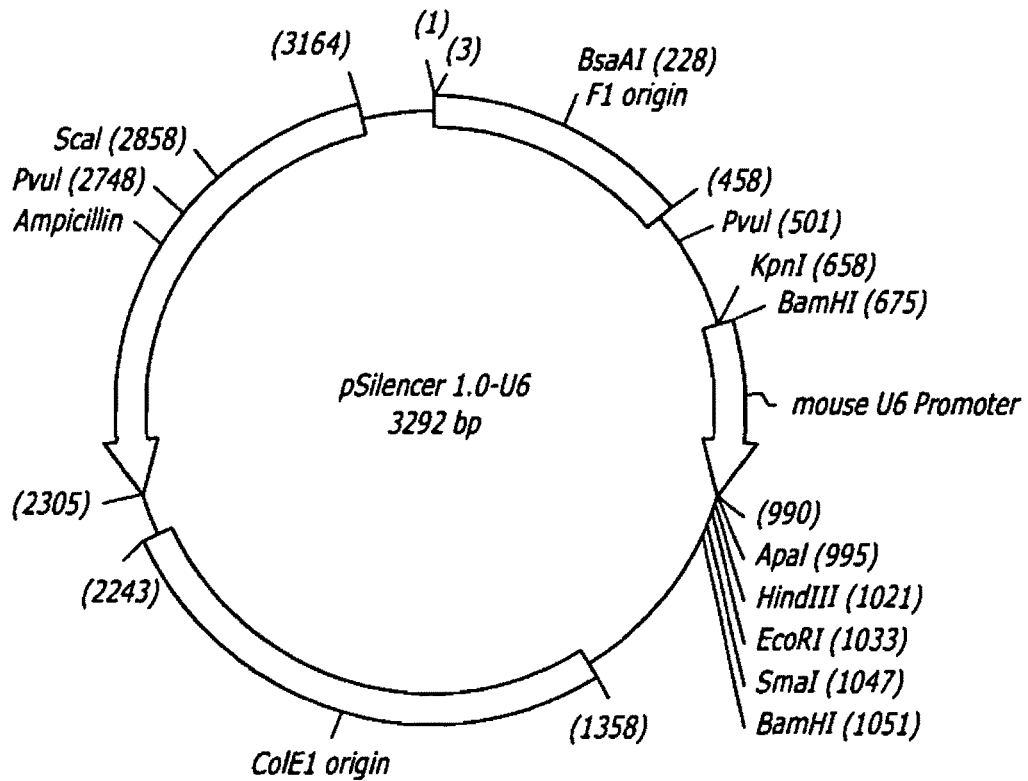
FIG. 4 shows a schematic description of a pSilencer 1.0-U6 plasmid that can be used in the preparation of anti-htt and control shNA sequences.

As suggested earlier, siNA nucleic acid sequences (and DNA sequences that encode for them) can be formatted into short hairpin nucleic acid ("shNA") structures. FIG. 3 shows a formatted structure and construction of an anti-mutated htt shNA sequence (SEQ ID NO: 112; FIG. 3A) and a control shNA sequence (SEQ ID NO: 113; FIG. 3B). The shNA sequences contain original nucleic acid sequences from Table 1 (boxed sequence shown in black), a nine nucleotide loop (underlined), the reverse complement of the boxed nucleic acid sequence (italicized), and a Pol III terminator sequence (TTTTTT (bolded)). Four partially overlapping synthesized oligonucleotides (-A1, -A3, -A2, and -A4 in FIG. 3A and -B1, -B3, B2 and -B4 in FIG. 3B) can be used to assemble the shNAs. In two separate reactions, the ⅓ and ⅔ oligonucleotides for each shNA can be annealed. Referring to FIGS. 3A and 3B, the A1 and B1 oligonucleotides include the boxed sequences. The A2 and B2 oligonucleotides include the underlined nine nucleotide loop, the reverse complement of oligonucleotides A1 and B1 respectively, the bolded Pol III terminator sequence (TTTTTT) and the first G of the EcoRI site depicted in these FIGS. The A3 and B3 oligonucleotides of FIGS. 3A and 3B respectively include the Apal overhang region, the reverse complement of the boxed A1/B1 sequences, and the reverse complement of the underlined nine nucleotide loop sequence. The A4 and B4 oligonucleotides include the reverse complement of the italicized portion of A2 and B2 respectively and the reverse complement (AAAAAA) of the bolded Pol III terminator sequence. Finally, the A4 and B4 oligonucleotides contain the EcoRI overhang region. Apal and EcoRI restriction enzyme-compatible ends are included in the shNA structures for directional subcloning into a murine U6 promoter-containing shuttle vector (pSilencer1.0-U6; Ambion, Inc., Austin, Tex.; FIG. 4). The full-length shNAs (SEQ ID NOS: 112 and 113) then can be cloned into a Apal/EcoRI-digested pSilencer vector using a three-way ligation reaction. The U6 promoter (murine or human) is used for constitutive high level expression of the nucleic acid sequences. In keeping with the present invention, a human H1 promoter can also be used.

While this example provides one embodiment of the nucleic acid sequences of the present invention in shNA format and a method for creating them, other configurations and methods also fall within the scope of the present invention. For example, in one embodiment, the loop structure of the hairpin structure is 4 to 10 nucleotides in length. In another embodiment, the arms of the hairpin structures are less than approximately 30 nucleotides in length. In another embodiment, the arms of the hairpin structure are between 19 and 27 nucleotides in length. Thus, while a specific example is given, this example should not be interpreted to limit the scope of the present invention.

Figure 5:
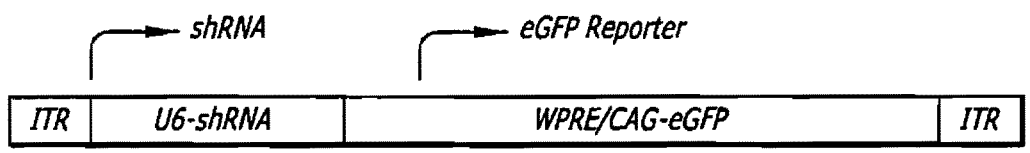
FIG. 5 shows the format of AAV viral constructs.

Next, a method to prepare viral production plasmids is described. This method will be based on the method for producing the nucleic acid sequences in shNA formats described above. As will be understood by one of skill in the art, however, various known modifications of the described technique also fall within the scope of the present invention. First, the BamHI fragment (FIG. 5) containing the shNA expression cassette (murine U6 promoter, shNA sequence, and Pol III terminator sequence) from each of the pSilencer shuttle vectors (htt and control) is recovered, blunted with T4 DNA polymerase, and subcloned into an AAV1/2 expression vector (deprAVE™; GeneDetect.com Ltd, Bradenton, Fla.). As shown in FIG. 5, in the final viral expression vector (used for virus production), the U6 promoter will drive the expression of the shNA and the Woodchuck enhancer/chicken .beta.-actin promoter will drive the expression of the enhanced green fluorescent protein (WPRE/CAG-eGFP). These expression cassettes can be flanked by viral inverted terminal repeats (ITR). The Woodchuck post-transcriptional regulatory element (WPRE) and the presence of a bovine growth hormone (BGH) polyadenlyation sequence ensure high transcription following cellular transduction. In alternative methods of the present invention, the expression cassette additionally contains a polyadenylation signal, such as a synthetic minimal polyadenylation signal.

The siNA sequences and molecules of the present invention can be manipulated to enhance their uptake into the RISC complex. Specifically, manipulating the 5' terminal nucleotide of the guide strand can be highly advantageous. Preferential entry of the guide, or antisense, strand into RISC can be achieved by introducing 5' mismatches in the antisense strand while maintaining perfect base pairing at the 5' terminus of the sense strand. This maximizes entry of the antisense strand into the RISC complex, while also reducing potential off-target inhibition by the sense strand.

Physical methods to introduce nucleic acid molecules and/or their carriers (i.e. vectors) into eukaryotic cells are known in the art. Some of these methods include, without limitation, calcium phosphate or calcium chloride co-precipitation, DEAE-dextran-mediated transfection, cationic lipid-mediated transfection, lipofection, protoplast fusion, particle bombardment, microinjection, liposome fusion, biolistics and other suitable methods found in, for example, Sambrook, et al. (Molecular Cloning: A Laboratory Manual, 2nd, ed, Cold Spring Harbor Laboratory, Cold Spring Harbor Laboratory Press, Cold Spring Harbor, N.Y., 1989), and other laboratory manuals. Further, biological methods to introduce nucleic acid molecules into a cell include the use of viral vectors. For mammalian gene therapy, viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like (see, for example, Boenisch et al., U.S. Pat. No. 5,350,674 and Wilson et al., U.S. Pat. No. 5,585,362 which are hereby incorporated by reference). Embodiments of the present invention also can be delivered through the use of liposomes, polyethyleneimine, by iontophoresis, or by incorporation into other vehicles, such as hydrogels, cyclodextrins, biodegradable nanocapsules, and bioadhesive microspheres. Nucleic acid molecules also can be directly delivered to cells or tissues with or without the aforementioned vehicles. The nucleic acid molecules/vehicle combinations can be locally delivered by catheter and drug pump systems, direct local injection or through the use of polymers and/or drug-eluting stents. In one embodiment of the present invention, nucleic acid molecules can be administered as described in United States published patent application number 20040220132, Treatment of Neurodegenerative Disease Through Intracranial Delivery of siRNA, which is hereby incorporated by reference.

The nucleic acid sequences, molecules, expression cassettes and vectors of the present invention are administered to prevent or treat the symptoms of HD. The amount of these agents administered as well as the timing of their delivery will vary depending on various factors including, for example and without limitation, the composition chosen, the weight, physical condition, and age of the patient, and whether prevention or treatment is desired as well as other factors known to skilled practitioners. Administration of the therapeutic agents can be continuous or intermittent. The administration of the agents of the invention can be essentially continuous over a preselected period of time or can be in a series of spaced doses. Further, both local and systemic administration can be appropriate for use within the present invention. Such factors can be determined by the researcher or treating physician.

EXAMPLE 1

Allele-Specific Suppression of the Huntingtin Gene

The following siRNA's were designed and used in the described study (synthesized by Ambion Inc., Austin, Tex.): TABLE-US-00003 SEQ ID siRNA Sense sequence: position 5465 on the NO:136 363125_C-16 5' GAGAUGGGGA-CAGUACUUCtt 3' Huntington mRNA (NM_002111.3) SEQ ID siRNA Anti-sense sequence: position 5465 on the NO:137 363125_C-16 5' GAAGUACUGUCCCCAUCUCtt 3' Huntington mRNA (NM_002111.3) SEQ ID siRNA Sense sequence: position 5472 on the NO:138 363125_A-9*10 5' GGACAGUAAGUCAACGCUAtt 3' Huntington mRNA (NM_002111.3) SEQ ID siRNA Anti-sense sequence: position 5472 on the NO:139 363125_A-9*10 5' UAGCG-UUGACUUACUGUCCct 3', Huntington mRNA (NM_002111.3)

Cell culture. Human fibroblasts from Huntington patients (GM04022, Coriell Institute) heterozygous for SNP363125 were cultured in Minimum Essential Medium with Earle's salts, L-glutamine, essential and non-essential amino acids, vitamins, and 15% fetal bovine serum (Gibco) at 37° C. and 5% $CO_2$.

Transfection. 4×10 fibroblasts were plated in a 25 $cm^2$ culture flask containing 4.2 ml of growth medium without antibiotics one day before transfection to achieve about 50% confluency at the time of transfection. The cells were transfected with 26 µl siRNA (20 µM) diluted in 500 82 1 Optimem using 26 µl Lipofectamine 2000 transfection reagent diluted in 500 µl Optimem (Invitrogen) or with 2.6 µl siRNA diluted in 50 Optimem using 2.6 µl Lipofectamine 2000 diluted in 50 µl Optimem. The final concentrations of siRNA in the culture dishes were 100 nM and 10 nM respectively. RNA was isolated after 36 hours of incubation.

Semi-quantification. The cells were harvested from the culture flasks with 1 ml of Trypsin-EDTA (0.25% Trypsin, 1 mM EDTA.4Na, Gibco) and the cell numbers were estimated by a cell count using a viability counter (Beckman coulter). Total RNA was isolated from the cells using the RNeasy mini kit (Qiagen) and gDNA was removed using an on column DNase treatment (30 min). After isolation, the quantity and quality of the RNA was analyzed using the Experion automated electrophoresis system (Bio-Rad) and the absence of gDNA was confirmed by PCR. Reverse transcription took place using the iScript cDNA synthesis kit (Bio-Rad). Subsequently, three Real Time PCR's were carried out, one for GAPDH using iQ SYBR Green supermix (Bio-Rad) and one for each allele of SNP363125 using molecular beacons. In all reactions, standard curves were generated by amplifying the following numbers of DNA control molecules (in triple) in a 25 reaction: $1 \times 10^9$, $1 \times 10^8$ . . . to $1 \times 10^2$. The DNA control molecules were chemically synthesized and had the same sequence as the PCR products. Primer sequences used included: GAPDH upper primer SEQ ID NO: 140 (5'-ACTC-CTCCAC CTTTGACGC-3'); GAPDH lower primer SEQ ID NO: 141 (5'-GTTGCTGTAGCCAAA TTCGTT-3') (optimal temperature and product length 56.7° C. and 95 by respectively); molecular beacon 363125 C: SEQ ID NO: 142 (5'-(6-FAM) cgcgatc GATGGGGACAGTA+CTTCMCGCTAGA gatcgcg (BHQ1)-3; Huntington upper primer SEQ ID NO: 143 (5'-AGATATTGTTCTTTCTCGTATTCAGG-3'); Huntington lower primer SEQ ID NO: 144 (5'-TGCTCACT-CATTTCCACCTTC-3') (optimal temperature and product length 59-62° C. and 234 by respectively); molecular beacon 363125_A: SEQ ID NO: 145 (5'-(6 FAM) agtgcgt GGGA-CAGTA+ATTCAACGCTAG acgcact (BHQ1)-3; Huntington upper primer SEQ ID NO: 146 (5'-CCTTCTCTCCG-TATT TAATCTCCTGTA-3'); Huntington lower primer SEQ ID NO: 147 (5'-TCATTTCC ACCTTCAGCTGTTTTGTM-3') (optimal temperature and product length 57° C. and 195 by respectively).

Figure 6:
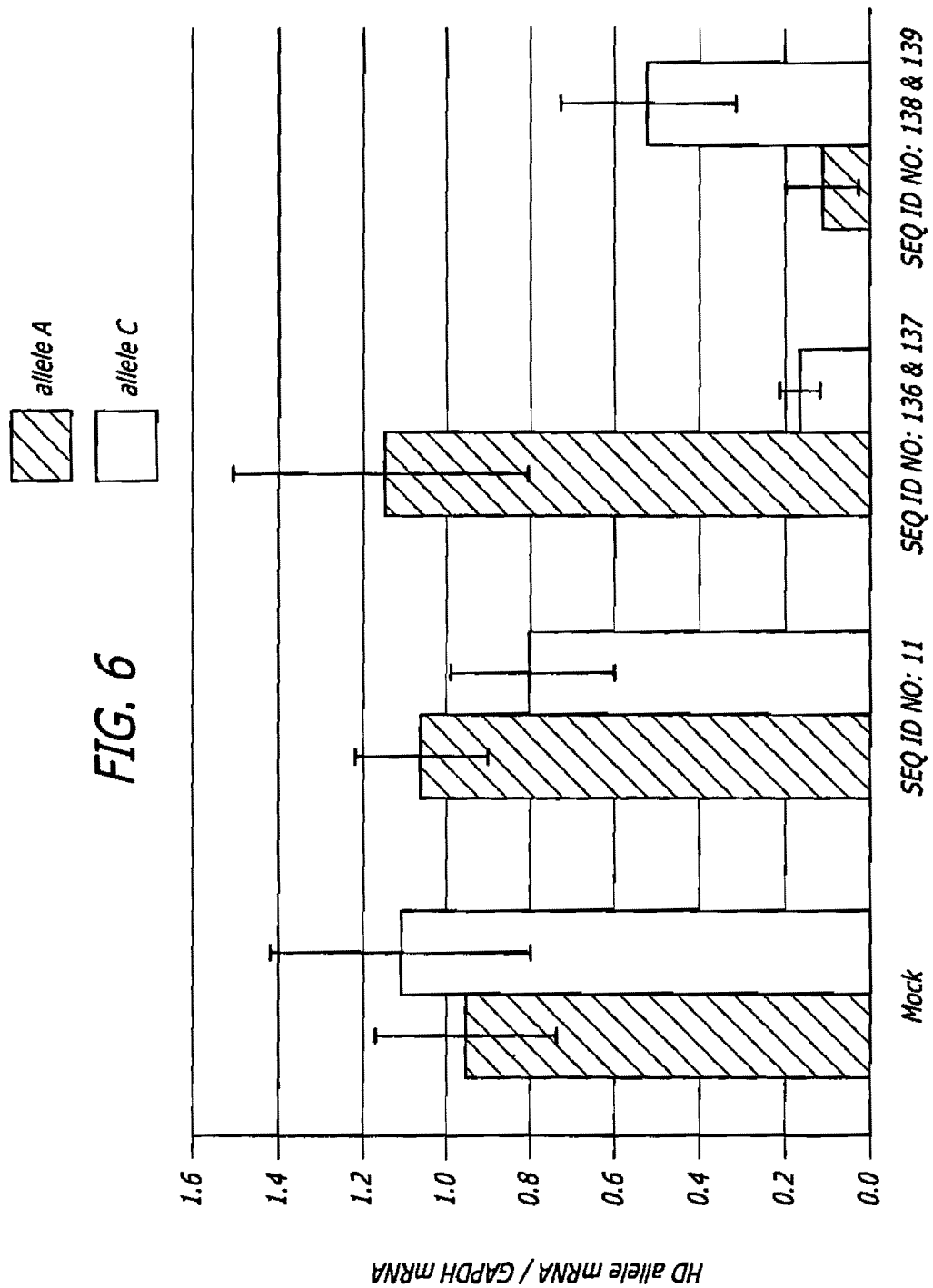
FIG. 6 shows allele-specific suppression of a mutated huntingtin gene.

As shown in FIG. 6, SEQ ID NOs: 136 and 137 suppressed only the C-allele of Huntington mRNA while having little to no effect on the A-allele of Huntington mRNA at SNP363125 (aka SNP07) when applied in vitro to a fibroblast cell line from a Huntington's disease patient heterozygous at this SNP site. More specifically, SEQ ID NOs: 136 and 137 suppressed the corresponding mRNA from the C allele of the Huntington's disease patient by about 83%, while showing little suppression if any of this patient's A-allele. Further siRNA with the SNP at position 9 and a further intentional mis-match at position 10 (SEQ ID NOs: 138 and 139) suppressed the A allele by about 85%, while suppressing the C allele by only about 47%. These results demonstrate the effectiveness of embodiments according to the present invention at allele-specific Huntingtin gene suppression.

EXAMPLE 2

Effectiveness of siNA and shNA Sequences in Treating HD Patients

A double-blind, placebo controlled study is conducted over a 1-year period. A total of 200 subjects, all presenting for treatment of HD are chosen for the study. The patients range in age from 35-65 years old.

An initial assessment of the symptoms of each patient is conducted when the patients initially present for treatment. The treating physician rates the severity of symptoms associated with HD on a 4-point scale (1: mild; 2: moderate; 3: strong; 4: severe). Patients then are screened for the presence of heterozygous SNPs within their HD genes. Patients that are heterozygous for a specific SNP within their HD genes are the 200 chosen for the study.

The 200 subjects chosen for the study are separated evenly into two main groups, treatment and control. The severity of the symptoms between the groups is comparable. No other medications are taken by the patients during the assessment period.

According to group assignment, patients receive intracranial administration of 10 mg of stabilized nucleic acid sequences in an appropriate vector every 7 days. Specifically, in this example, AAV vectors encoding for siNA molecules are delivered through the use of implanted, indwelling, intraparenchymal catheters as described in published U.S. Patent Application No. 2004/0220132. The treatment and control groups each are divided into two subgroups. One subgroup of the treatment group receives a siNA molecule directed against a SNP found in an individual patient's mutated HD gene. The second subgroup of the treatment group receives the same treatment except that the siNA molecules are in shNA formats. The control groups receive control sequences. Half of the control group receives control sequences in siNA formats while the second half receives control sequences in shNA formats.

During the 1 year evaluation period, patients self-evaluate the severity of their HD symptoms using the same 4-point scale (1: mild; 2: moderate; 3: strong; 4: severe) each morning and evening. Patients also note the presence and severity of adverse effects of the drug administration on the 4-point scale. In addition to the initial assessment by the treating physician, patients are evaluated at the end of each week by the treating physician.

A significant improvement in HD symptoms is observed in all of the treated subjects over the controls upon completion of the study. There is no significant difference in the effectiveness of siNA sequences as compared to shNA sequences. This study demonstrates the efficacy of the nucleic acid sequences of the present invention in treating the symptoms of HD. Regarding potential adverse effects, there are no significant differences between the therapeutic groups. Thus, this study demonstrates that the intracranial administration of nucleic acid sequences directed against mutated htt provides an effective treatment for the symptoms of HD. The study also demonstrates that the treatment is well-tolerated by patients.

It is to be understood that the present invention is not limited to the particular embodiments, materials, and examples described herein, as these can vary. For example, the nucleic acid molecules of the present invention can be created in a variety of formats and lengths. Indeed, those skilled in the art will recognize that the most important attribute of the nucleic acid molecules of the present invention is their ability to complementarily bind to the mRNA sequences of interest to reduce the mRNA stability and/or the translation rate of these sequences. The phrase "complementarily bind" as used herein, refers to the abilities of the nucleic acid molecules to form hydrogen bond(s) with mRNA sequences by either traditional Watson-Crick pairing or other non-traditional types.

It also is to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a sequence" or "a shNA" is a reference to one or more sequences or shNAs and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

The invention claimed is:

1. A kit for screening an individual for the heterozygous presence of one or more single nucleotide polymorphisms (SNPs) within said individual's Huntington's disease genes, the kit comprising two pairs of molecular beacons selected from the group consisting of:

(a) a molecular beacon that detects a single polymorphism found in SEQ ID NO: 13, wherein said molecular beacon comprises at least a portion of a reverse complement of SEQ ID NO: 13 and a molecular beacon that detects a single polymorphism found in SEQ ID NO: 14, wherein said molecular beacon comprises at least a portion of a reverse complement of SEQ ID NO: 14;

(b) a molecular beacon that detects a single polymorphism found in SEQ ID NO: 15, wherein said molecular beacon comprises at least a portion of a reverse complement of SEQ ID NO: 15 and a molecular beacon that detects a single polymorphism found in SEQ ID NO: 16, wherein said molecular beacon comprises at least a portion of a reverse complement of SEQ ID NO: 16;

(c) a molecular beacon that detects a single polymorphism found in SEQ ID NO: 3, wherein said molecular beacon comprises at least a portion of a reverse complement of SEQ ID NO: 3; and a molecular beacon that detects a single polymorphism found in SEQ ID NO: 4, wherein said molecular beacon comprises at least a portion of a reverse complement of SEQ ID NO: 4; and (d) a molecular beacon that detects a single polymorphism found in SEQ ID NO: 7, wherein said molecular beacon comprises at least a portion of a reverse complement of SEQ ID NO: 7 and a molecular beacon that detects a single polymorphism found in SEQ ID NO: 8, wherein said molecular beacon comprises at least a portion of a reverse complement of SEQ ID NO: 8, wherein all the molecular beacons that detect a SNP for which said individual is heterozygous are selected from the group.

2. The kit of claim 1, further comprising nucleic acid molecules capable of mediating RNA interference (RNAi) that preferentially suppress the expression of amino acid sequences encoding for mutated huntingtin ("htt") over suppressing the expression of amino acid sequences encoding for normal htt by targeting an area of a Huntington's disease gene that is heterozygous for the presence of one or more single nucleotide polymorphisms.

3. The kit of claim 1 wherein said one or more single nucleotide polymorphisms are selected from the group consisting of SNP8, SNP7 SNP2, and SNP4.

4. A method for screening individuals for the heterozygous presence of one or more SNPs within the individual's Huntingtin genes, comprising probing a nucleic sequence encoding huntingtin of said individual with one or more molecular beacons of kit of claim 1, wherein said one or more SNPs are selected from SNP2, SNP4, SNP7 and SNP8.

5. A kit for screening an individual for the heterozygous presence of one or more single nucleotide polymorphisms (SNPs) within said individual's Huntington's disease genes, the kit comprising:
   a) a molecular beacon that detects a single polymorphism found in SEQ ID NO: 13, wherein said molecular beacon comprises at least a portion of a reverse complement of SEQ ID NO: 13;
   b) a molecular beacon that detects a single polymorphism found in SEQ ID NO: 14, wherein said molecular beacon comprises at least a portion of a reverse complement of SEQ ID NO: 14;
   c) a molecular beacon that detects a single polymorphism found in SEQ ID NO: 15, wherein said molecular beacon comprises at least a portion of a reverse complement of SEQ ID NO: 15;
   d) a molecular beacon that detects a single polymorphism found in SEQ ID NO: 16, wherein said molecular beacon comprises at least a portion of a reverse complement of SEQ ID NO: 16; and
   e) nucleic acid molecules capable of mediating RNAi that preferentially suppress the expression of amino acid sequences encoding for mutated huntingtin ("htt") over suppressing the expression of amino acid sequences encoding for normal htt by targeting an area of a Huntington's disease gene that is heterozygous for the presence of one or more single nucleotide polymorphisms selected from the group consisting of SNP07 and SNP08, wherein all the molecular beacons that detect a SNP for which said individual is heterozygous are selected from the group consisting of a)-d).

6. A method for screening individuals for the heterozygous presence of one or more SNPs within the individual's Huntingtin genes, comprising probing a nucleic sequence encoding huntingtin of said individual with one or more molecular beacons of kit of claim 5, wherein said one or more SNPs are selected from SNP7 and SNP8.

7. The kit of claim 1, wherein the kit comprises said pairs (a) and (b) of molecular beacons.

8. The kit of claim 7, wherein the kit further comprises at least one pair of molecular beacons selected from said pairs (c) and (d).

9. The kit of claim 1, wherein said each SNP detected by each molecular beacon in the kit accounts for 9% or more heterozygous presence in the Huntington's disease gene in a Huntington's disease patient population.

10. The kit of claim 5, wherein said each SNP detected by each molecular beacon in the kit accounts for 9% or more heterozygous presence in the Huntington's disease gene in a Huntington's disease patient population.

* * * * *